US012678519B2

(12) United States Patent
Gu et al.

(10) Patent No.: US 12,678,519 B2
(45) Date of Patent: Jul. 14, 2026

(54) BRAND-NEW SKELETON 99MTC-FAPI DIAGNOSTIC PROBE AND USE THEREOF IN PREPARATION OF DRUG OR REAGENT FOR DIAGNOSING TUMORS

(71) Applicant: NANJING NUOYUAN MEDICAL DEVICES CO., LTD, Nanjing (CN)

(72) Inventors: Yueqing Gu, Nanjing (CN); Yang Luo, Nanjing (CN); Zihan Wu, Nanjing (CN); Qiao Lin, Nanjing (CN); Feng Wang, Nanjing (CN); Pengjun Zhang, Nanjing (CN); Zhihao Han, Nanjing (CN)

(73) Assignee: NANJING NUOYUAN MEDICAL DEVICES CO., LTD, Nanjing (CN)

( * ) Notice: Subject to any disclaimer, the term of this patent is extended or adjusted under 35 U.S.C. 154(b) by 0 days.

(21) Appl. No.: 19/344,588

(22) Filed: Sep. 30, 2025

(65) Prior Publication Data

US 2026/0021212 A1 Jan. 22, 2026

Related U.S. Application Data

(63) Continuation of application No. PCT/CN2024/120541, filed on Sep. 24, 2024.

(30) Foreign Application Priority Data

May 7, 2024 (CN) ......................... 202410553204.1

(51) Int. Cl.
*A61K 51/04* (2006.01)
*C07B 59/00* (2006.01)

(52) U.S. Cl.
CPC ...... *A61K 51/0497* (2013.01); *A61K 51/0459* (2013.01); *C07B 59/002* (2013.01); *A61K 2123/00* (2013.01); *C07B 2200/05* (2013.01)

(58) Field of Classification Search
CPC . C07B 59/002; C07B 2200/05; C07B 59/004; A61K 51/0459; A61K 51/0497; A61K 2123/00; C07D 401/12; C07D 401/14; C07D 513/04
See application file for complete search history.

(56) References Cited

U.S. PATENT DOCUMENTS

| | | | | |
|---|---|---|---|---|
| 2019/0185451 A1* | 6/2019 | Alfaro | .................. | C07D 403/12 |
| 2020/0206216 A1* | 7/2020 | Pujala | .................. | C07D 417/14 |

FOREIGN PATENT DOCUMENTS

| | | | |
|---|---|---|---|
| CN | 103041411 | A | 4/2013 |
| CN | 111991570 | A | 11/2020 |
| CN | 113292538 | A | 8/2021 |
| CN | 113880811 | A | 1/2022 |
| CN | 115260160 | A | 11/2022 |
| CN | 115974962 | A | 4/2023 |
| CN | 116554146 | A | 8/2023 |
| CN | 117105987 | A | 11/2023 |
| CN | 118271393 | A | 7/2024 |

OTHER PUBLICATIONS

Simone Egetenmeyer et al., A 5'-Cap for DNA Probes Binding RNA Target Strands, Chemistry—A European Journal, Sep. 20, 2011, p. 11813-11827, vol. 17, Issue 42.

Xin Gao et al., PDGFRβ targeted innovative imaging probe for pancreatic adenocarcinoma detection, Talanta, Dec. 31, 2023, vol. 255.

Qiao Lin et al., Ultrasensitive near-infrared fluorescence probe activated by nitroreductase for in vivo hypoxia detection, Sensors and Actuators B: Chemical, Nov. 15, 2022, vol. 371.

Xianrui Yin et al., A novel CXCR4-targeted peptide for SPECT/CT imaging in tumor, Sensors and Actuators B: Chemical, Jul. 1, 2024, vol. 410.

Haoran Xu et al., SPECT Imaging of Hepatocellular Carcinoma Detection by the GPC3 Receptor, Mol Pharmaceutics, May 3, 2021, vol. 18.

First Office Action of counterpart Chinese Patent Application No. 202410553204.1 issued on Jun. 5, 2024.

International Search Report of PCT Patent Application No. PCT/CN20Z4/120541 issued on Jan. 9, 2025.

Written Opinion of PCT Patent Application No. PCT/CN2024/120541 issued on Jan. 9, 2025.

* cited by examiner

*Primary Examiner* — Michael G. Hartley
*Assistant Examiner* — Leah H Schlientz

(57) ABSTRACT

The present disclosure discloses a brand-new skeleton 99mTc-FAPI diagnostic probe and use thereof in the preparation of a drug or a reagent for diagnosing tumors, wherein the structural formula of a dimeric compound targeting FAP is shown by following formula. Compared with conventional FAP inhibitor radiopharmaceuticals, technetium-99m-labeled novel skeleton FAP inhibitor dimeric compound has a very high tumor uptake rate, high contrast between tumor and background and good in vivo biodistribution.

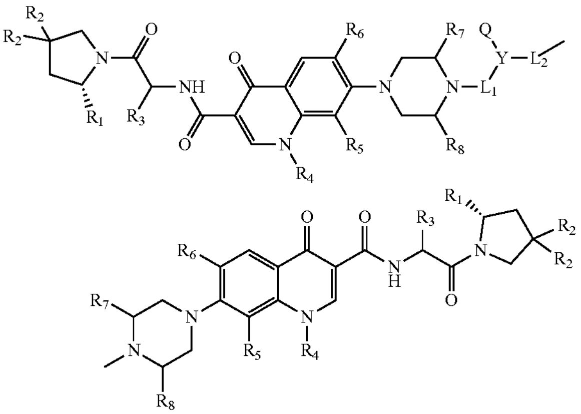

5 Claims, 11 Drawing Sheets

A

B

A

B

BRAND-NEW SKELETON 99MTC-FAPI DIAGNOSTIC PROBE AND USE THEREOF IN PREPARATION OF DRUG OR REAGENT FOR DIAGNOSING TUMORS

CROSS-REFERENCE TO RELATED APPLICATIONS

The present application is a continuation application of PCT application No. PCT/CN2024/120541 filed on Sep. 24, 2024, which claims the benefit of Chinese Patent Application No. 202410553204.1 filed on May 7, 2024. The contents of all of the aforementioned applications are incorporated by reference herein in their entirety.

TECHNICAL FIELD

The present disclosure relates to a brand-new skeleton 99mTc-FAPI diagnostic probe and use thereof in the preparation of a drug or a reagent for diagnosing tumors, belonging to the field of pharmaceutical chemistry.

BACKGROUND ART

Fibroblast activation protein-α (FAP) is a transmembrane serine protease primarily expressed on a surface of tumor-associated fibroblasts, selectively highly expressed in over 90% of epithelial-derived tumors, and highly expressed in liver cancer, colorectal cancer, pancreatic cancer and ovarian cancer, etc., while exhibiting no or relatively low expression in normal tissues. FAP can affect tumor growth through a variety of mechanisms, including proliferation promotion, invasion, angiogenesis, epithelial to mesenchymal transition, stem cell promotion, immune suppression and drug resistance. Given widespread expression of FAP in tumors and impact on tumor growth through a variety of mechanisms, FAP has become an important target for tumor imaging and therapy. Currently, substantial researches indicate that FAPI labeled by diagnostic nuclides as a broad-spectrum tumor imaging agent is superior to 18F-FDG in diagnostic performance. Current diagnostic FAPIs for clinical development are mostly based on 18F, 68Ga, and 64Cu PET probes, and there are relatively few diagnostic FAP probes based on 99mTc-SPECT.

SUMMARY

Objective of the present disclosure: the technical problem to be solved by the present disclosure is to provide a dimeric compound targeting FAP with a relatively high tumor uptake rate and imaging contrast, and a preparation method therefor and use thereof.

Technical solution: in order to solve the above technical problem, the present disclosure provides a dimeric compound targeting FAP, and a pharmaceutically acceptable salt, hydrate, and solvate thereof, and a corresponding technetium-99m radionuclide marker. The compound has a structure as follows:

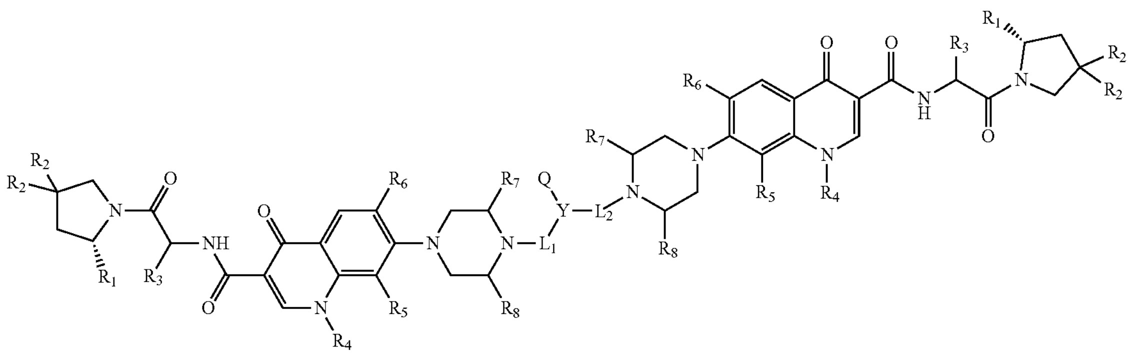

wherein $R_1$ is selected from cyano, aldehydo or chloroacetyl;

$R_2$ is selected from hydrogen, deuterium, fluoro or chloro;

$R_3$ is selected from hydrogen, deuterium, methyl, isopropyl, isobutyl, cyclopropyl or cyclobutyl;

$R_4$ is selected from hydrogen, methyl, ethyl, propyl, cyclopropyl or cyclobutyl;

$R_5$ and $R_6$ are independently selected from hydrogen, methyl, fluoro, chloro, hydroxy or methoxy;

$R_7$ and $R_8$ are the same or different and independently selected from hydrogen, methyl, halogen or carbonyl;

$L_1$ and $L_2$ as linkers are the same or different, and independently selected from, but not limited to, at least one of aliphatic carbon chains, polyethylene glycol chains and amino acid chains with different lengths, and comprise side chains spliced by different reactions, wherein the reactions include at least one of amide condensation reaction, ester condensation reaction, substitution reaction or click chemical reaction;

Y is selected from any one of:

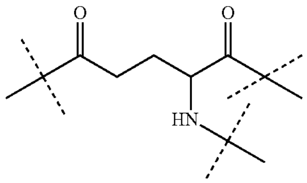

-continued

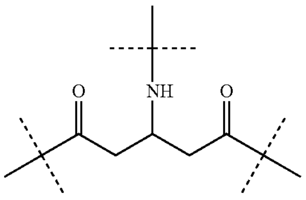

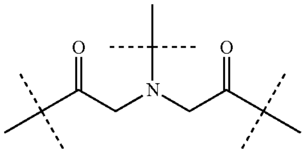

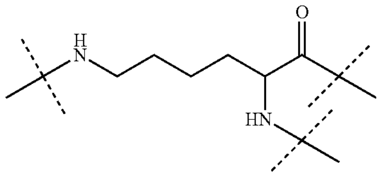

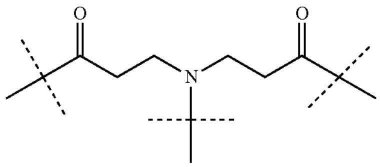

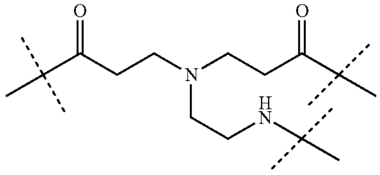

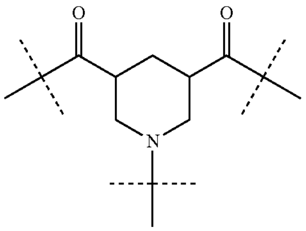

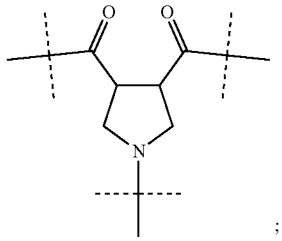

;

and

Q is a hydrogen atom or is used as a nuclide chelating group moiety, and is selected from any group that can be chelate-coordinated with technetium-99mTc.

In a preferred solution of the present disclosure, the $L_1$ and $L_2$ as linkers are independently selected from aliphatic carbon chains, polyethylene glycol chains or amino acid chains with different lengths, and comprise side chains spliced by different reactions, wherein the reactions include at least one of amide condensation reaction, ester condensation reaction, substitution reaction or click chemical reaction.

Herein, $L_1$ and $L_2$ are independently selected from any one of following structures:

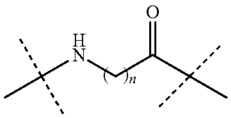

$n$ = 1-20

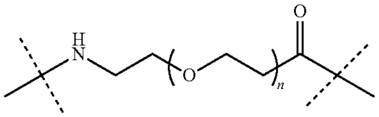

$n$ = 0-10

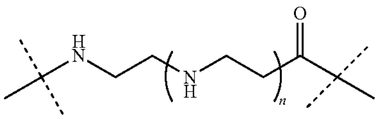

$n$ = 0-10

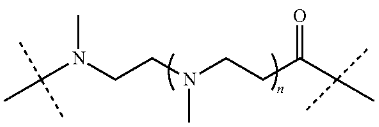

$n$ = 0-10

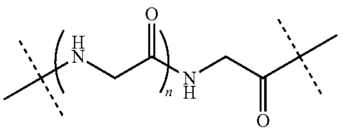

$n$ = 1-10

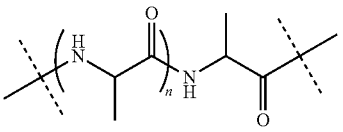

$n$ = 1-10

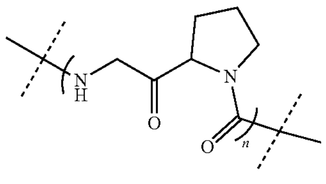

$n$ = 1-10

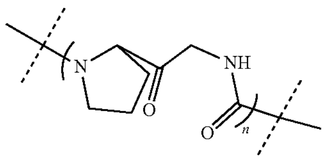

$n$ = 1-10

-continued
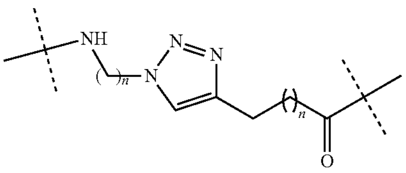
*n* = 1-10
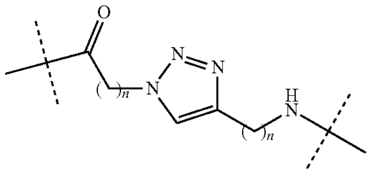
*n* = 1-10
wherein Q is a hydrogen atom or is used as a nuclide chelating group moiety selected from any one of:
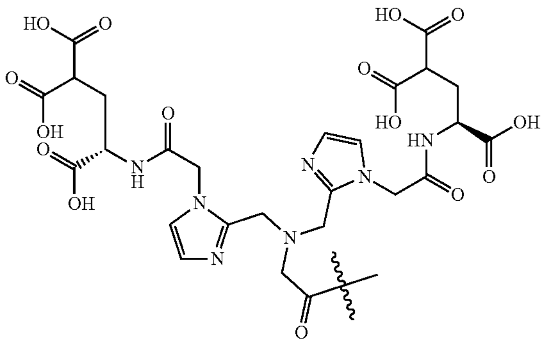
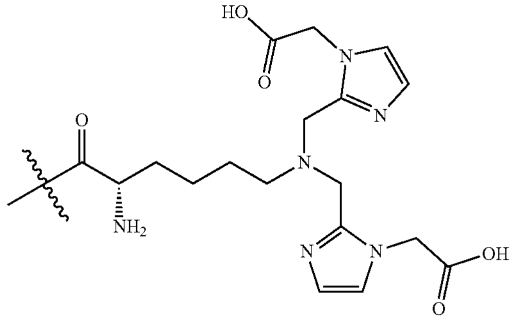
-continued
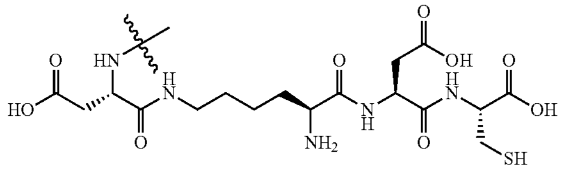
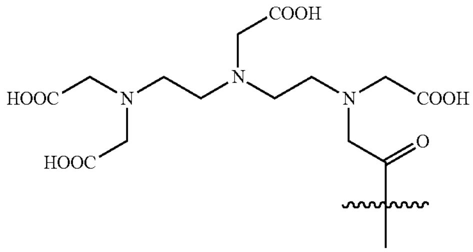
DTPA
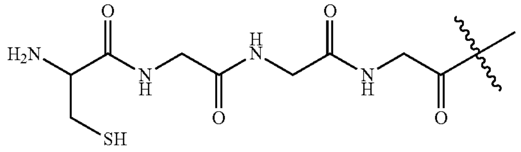
MAG3
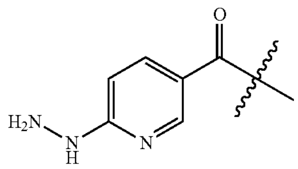
HYNIC
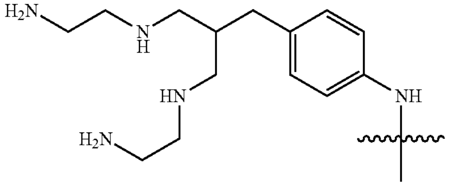
wherein Q is preferably selected to be 6-hydrazinonicotinic acid (HYNIC).

In a preferred solution of the present disclosure, the compound is selected from any one of:
1
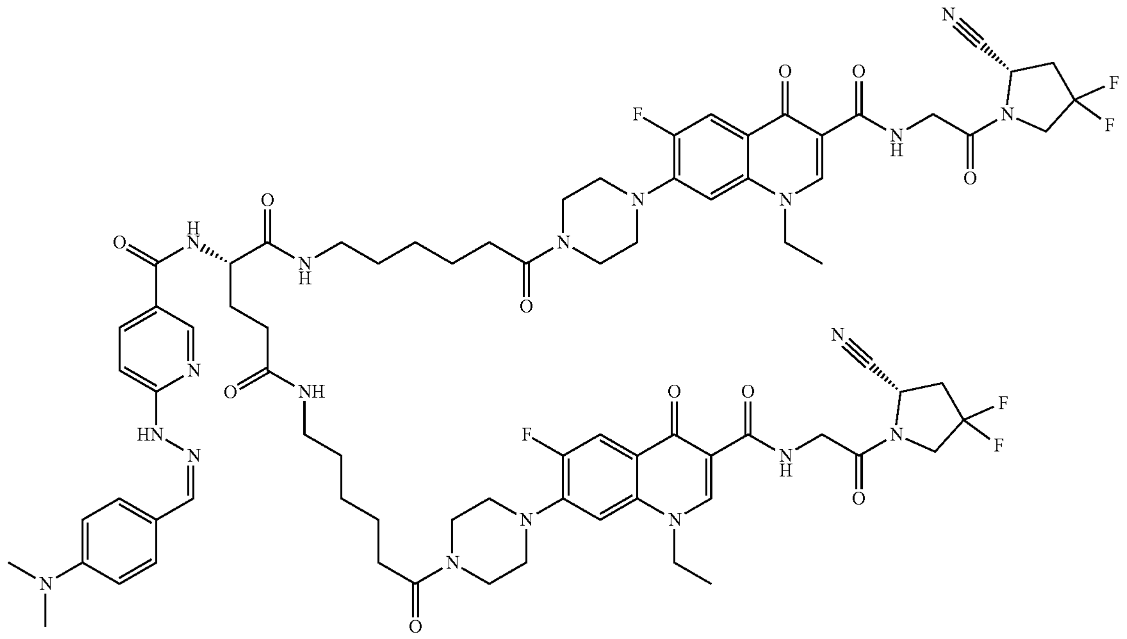
2
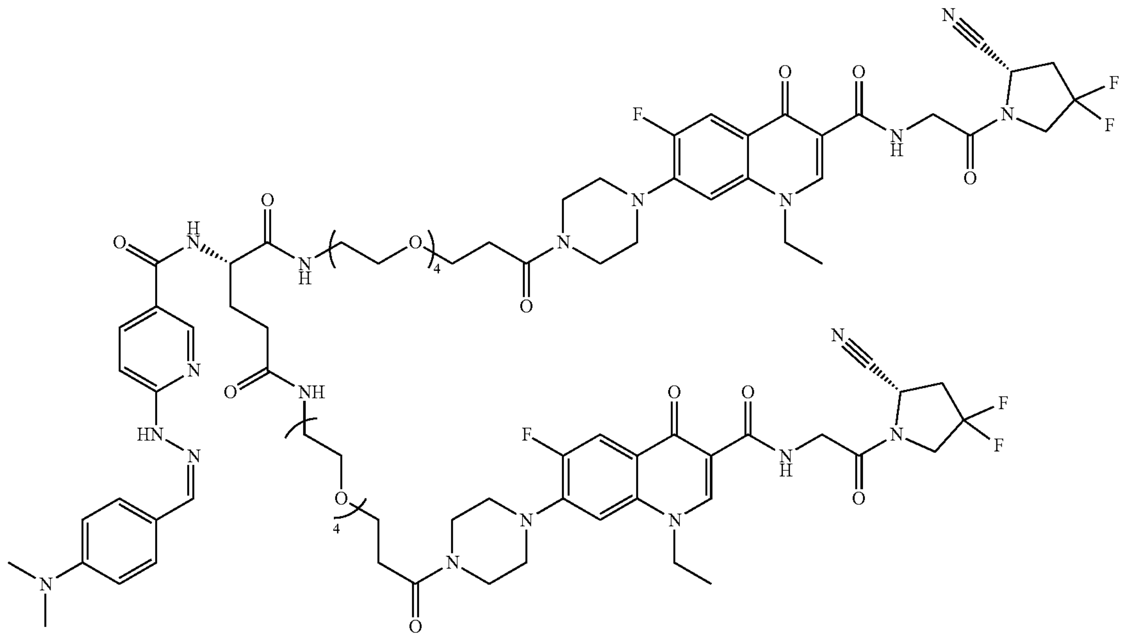

-continued
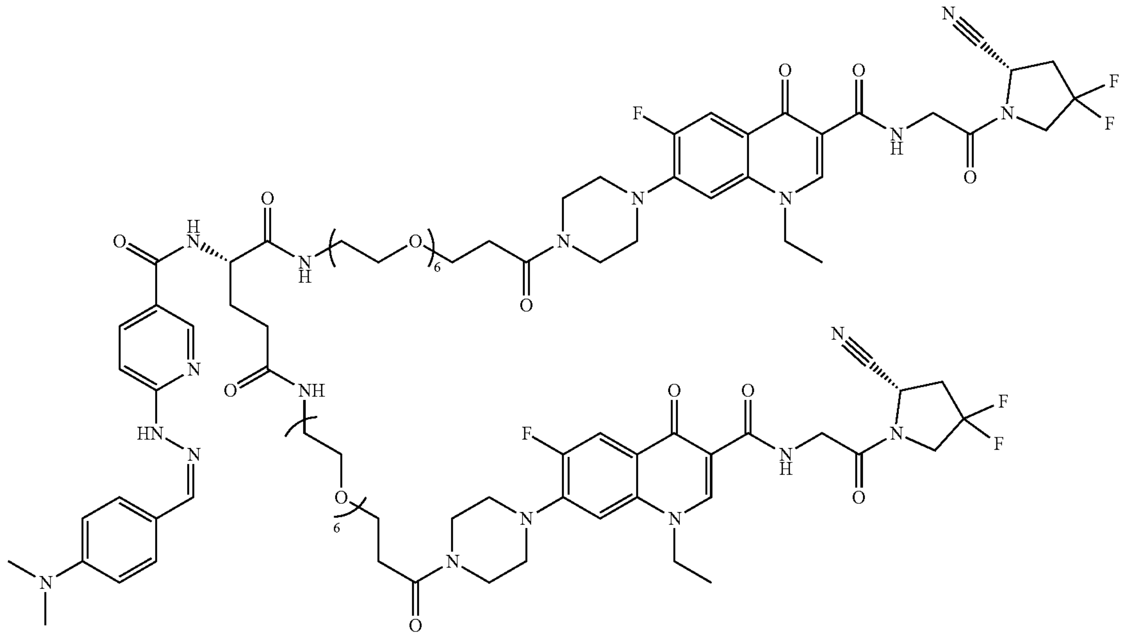
3
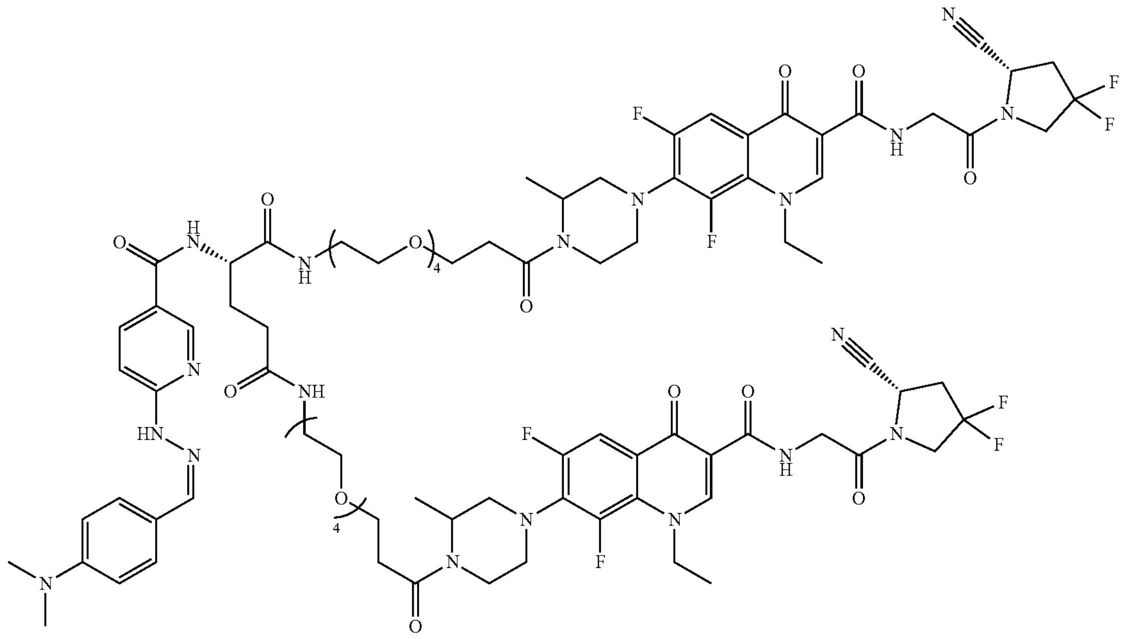
4

-continued
5
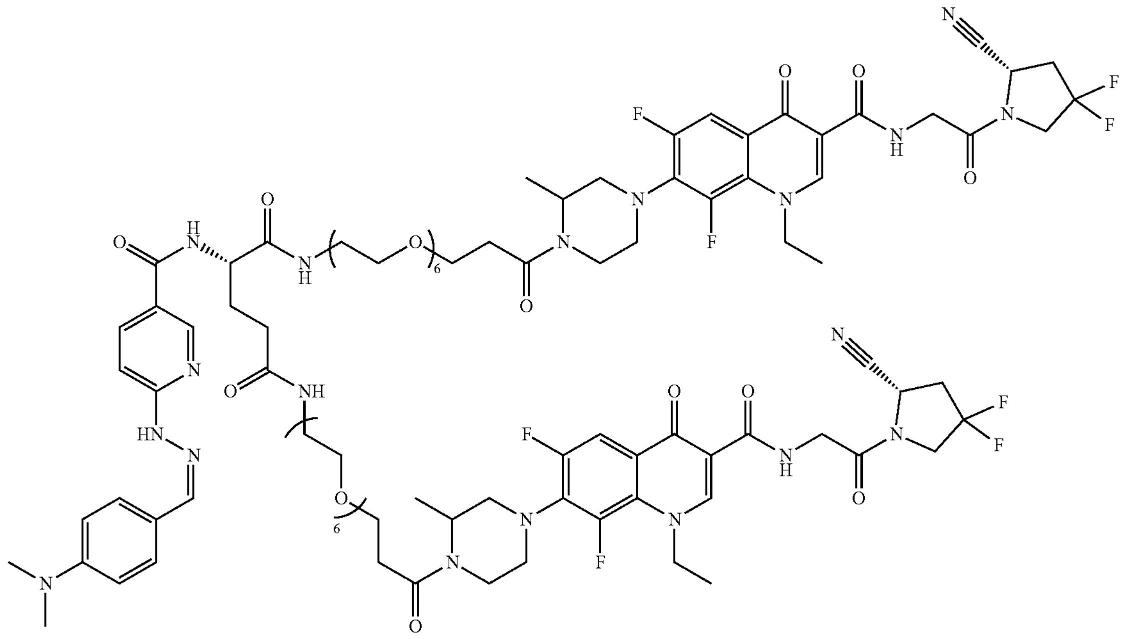
6
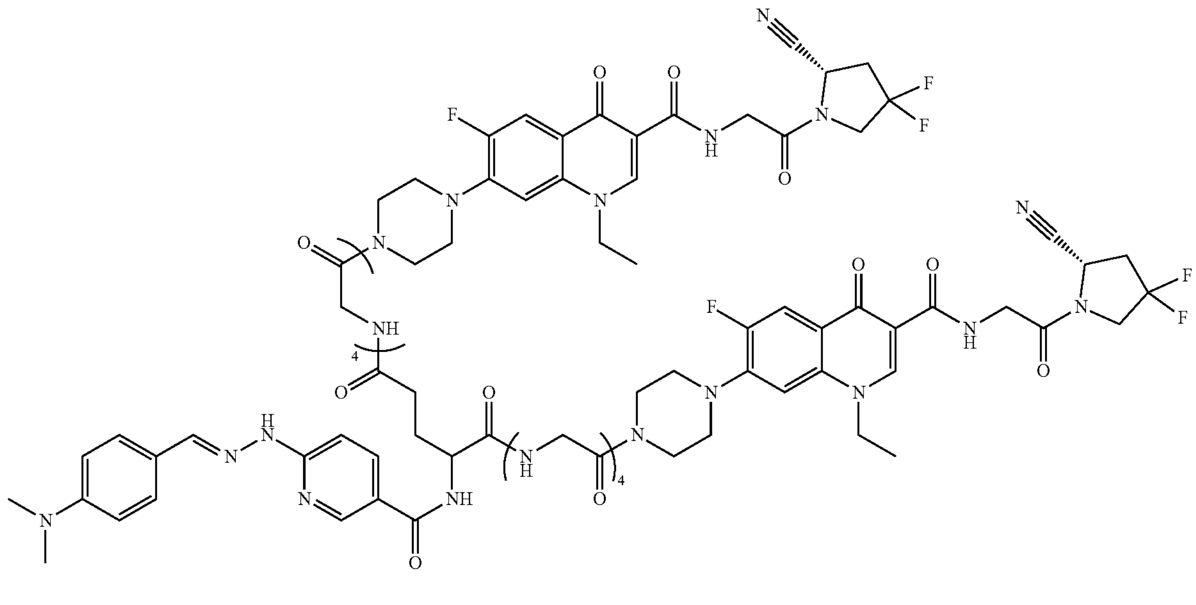

-continued
7
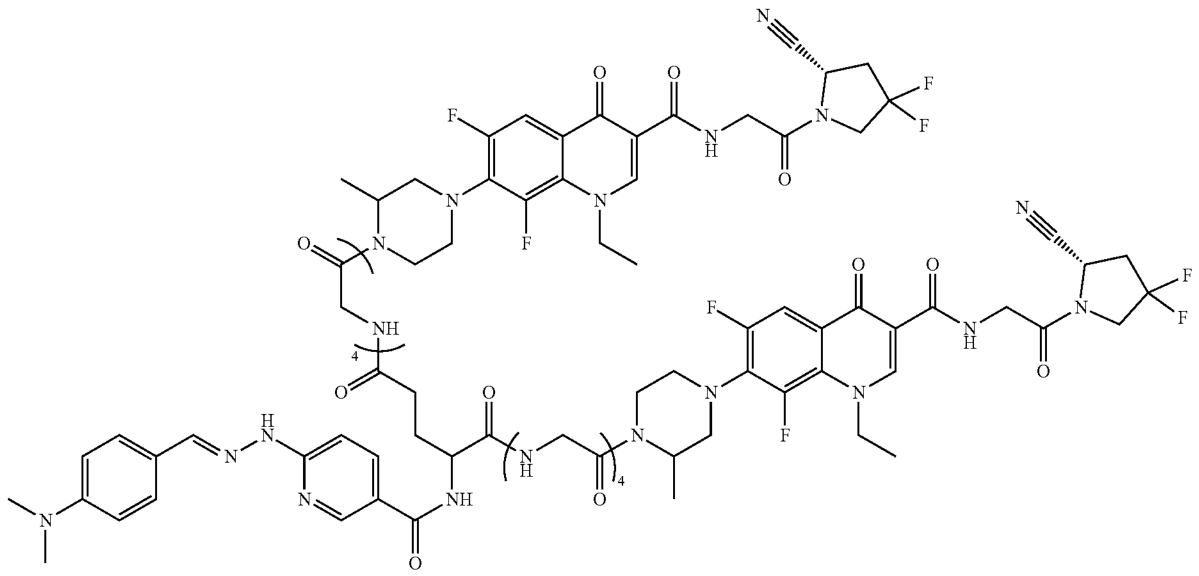
8
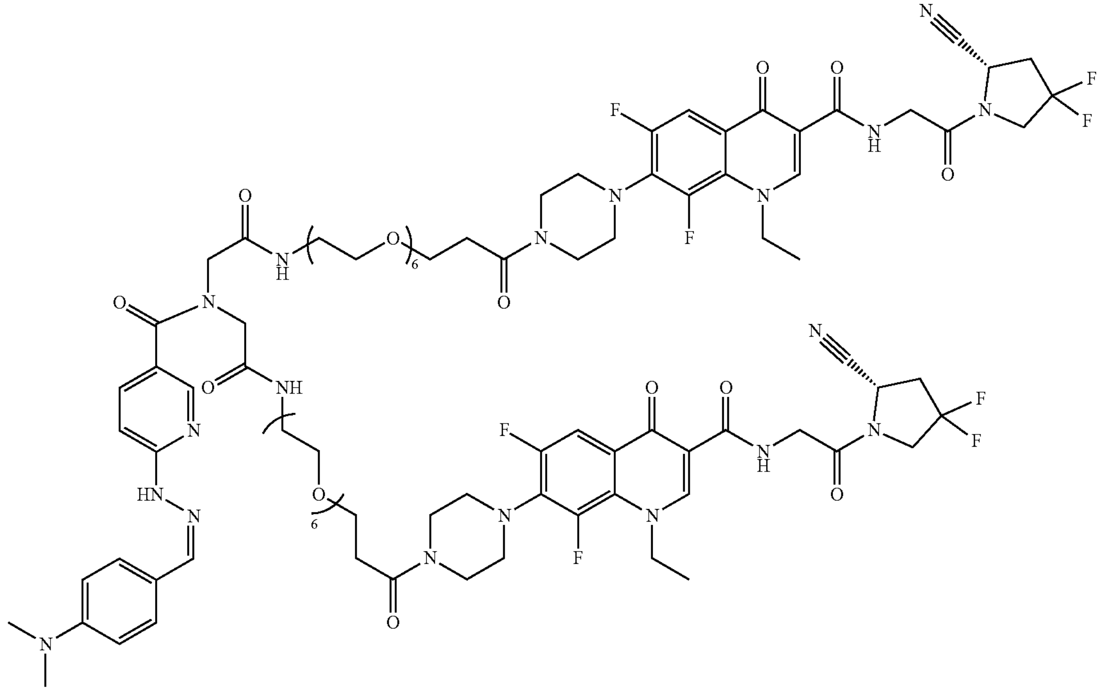

-continued
9
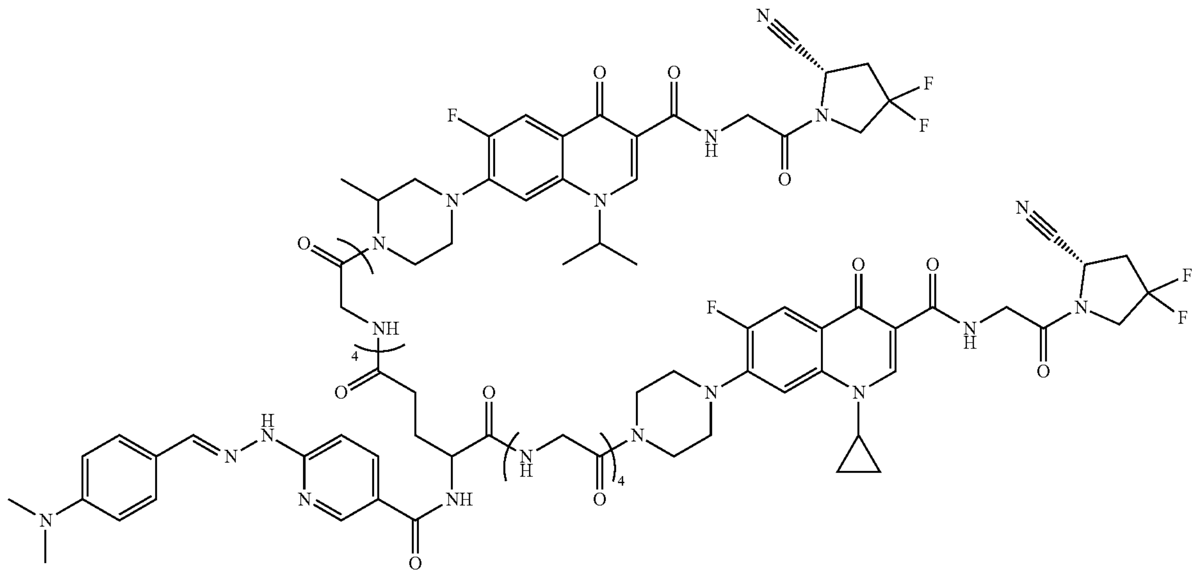
10
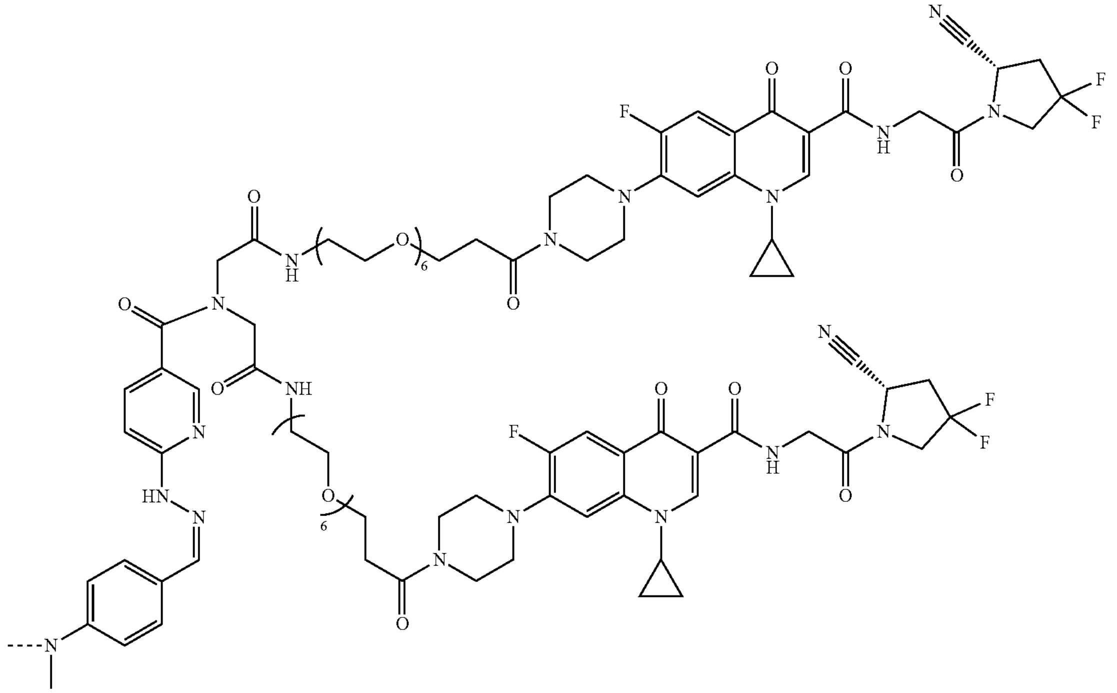

-continued
11
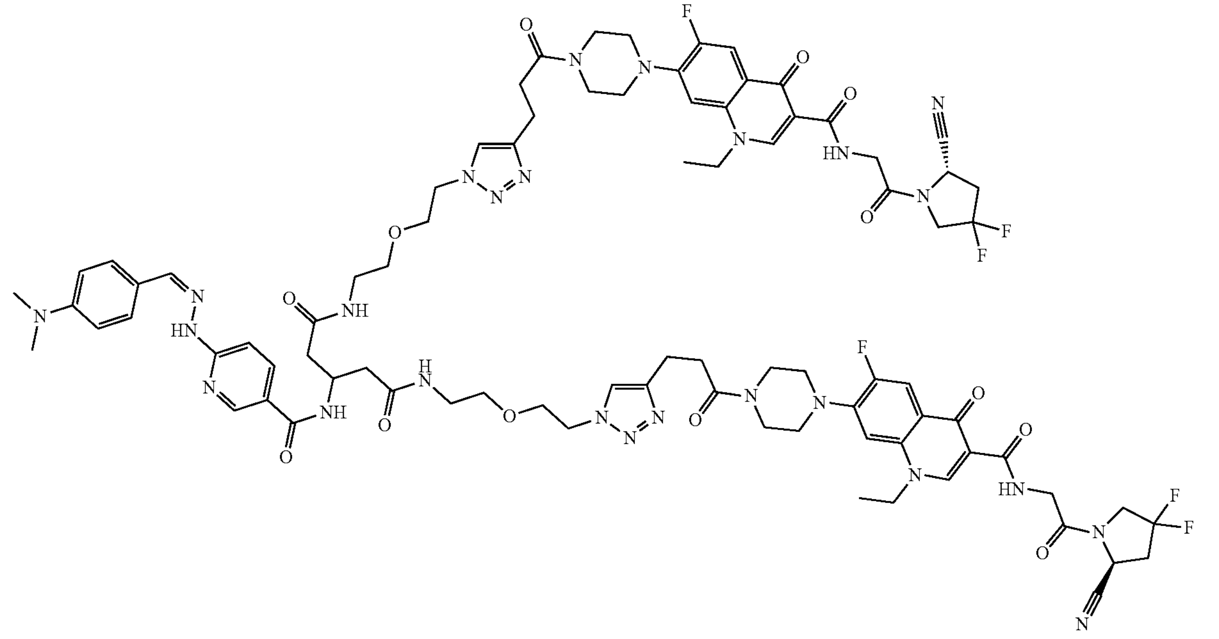
12
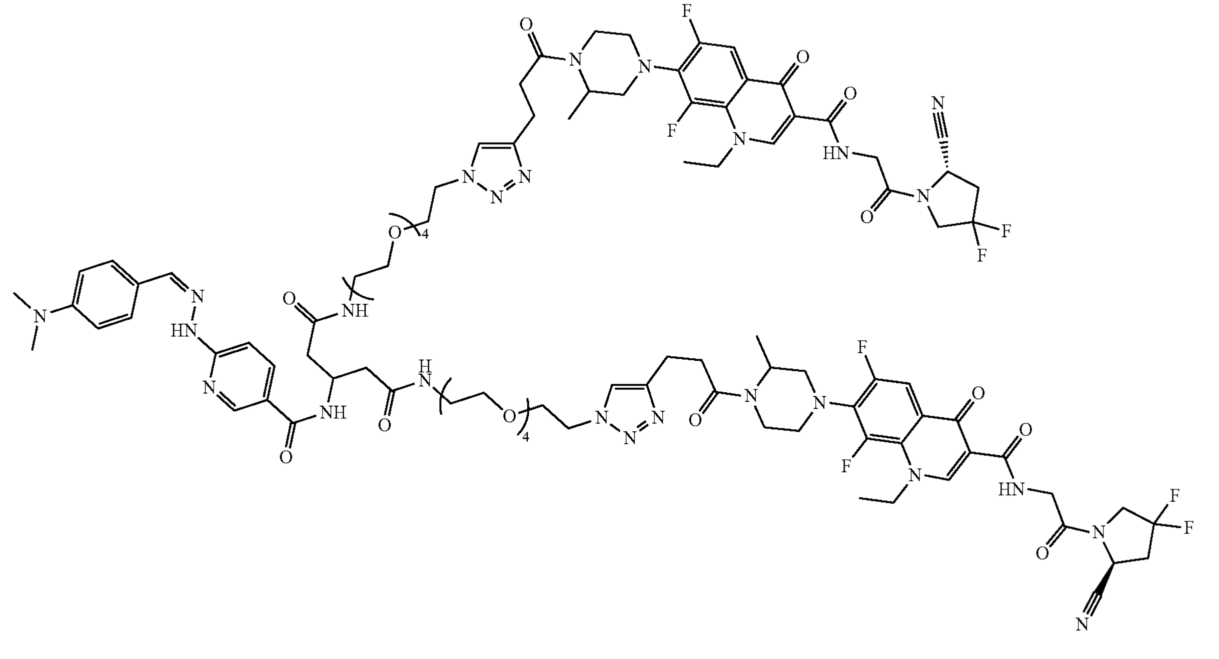

-continued
13
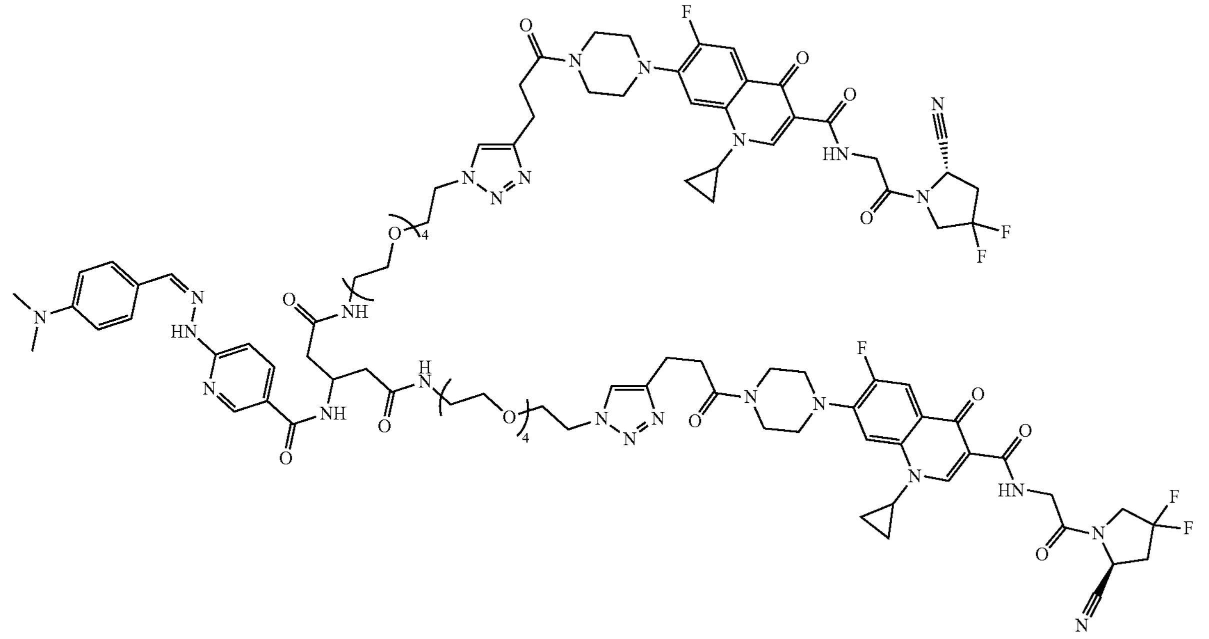
14
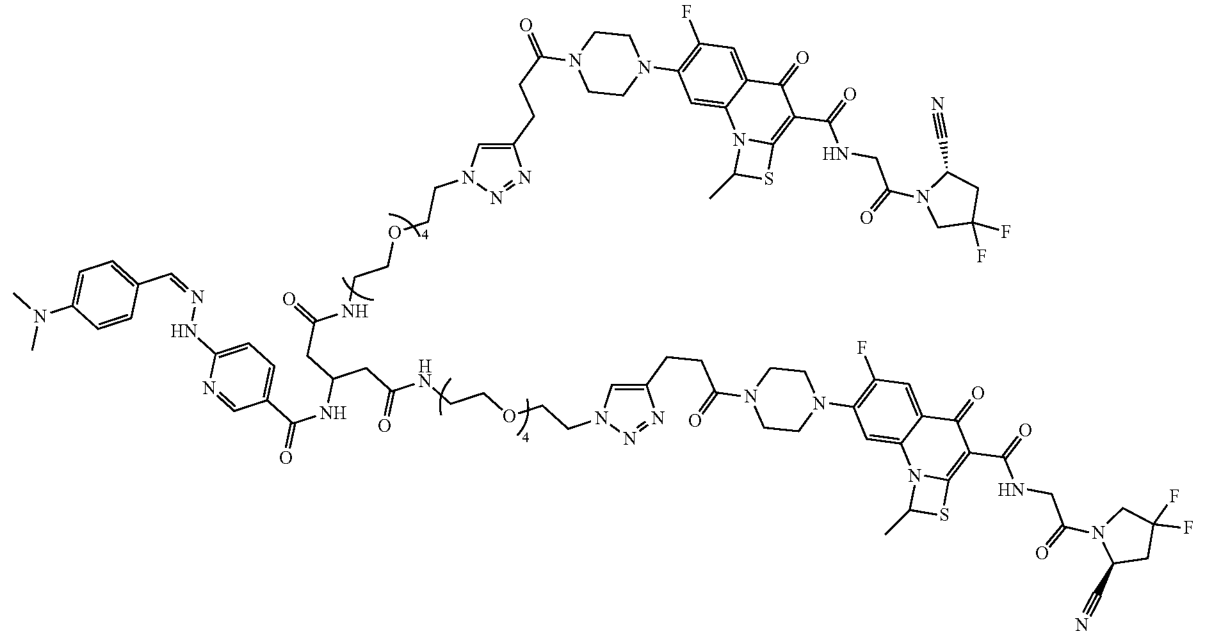

-continued

15

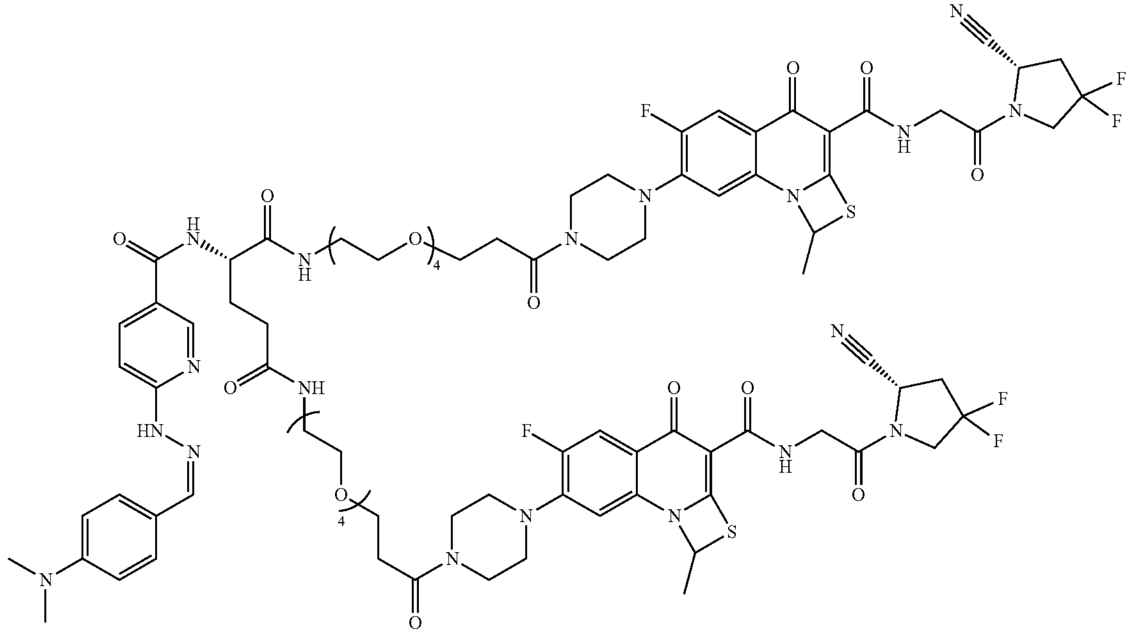

16

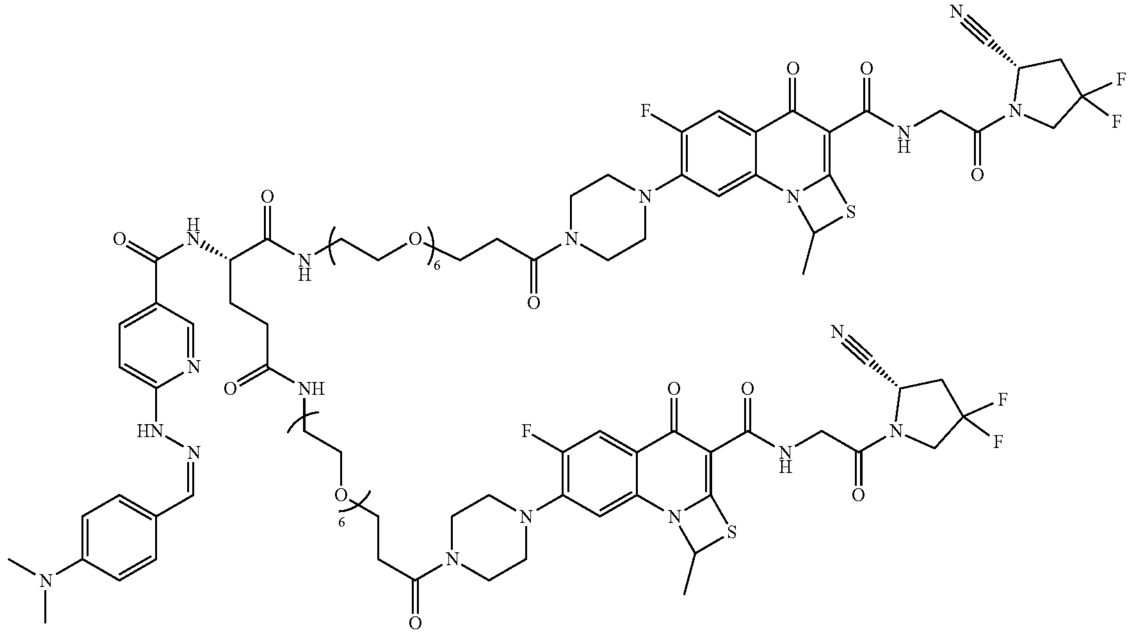

The present disclosure further provides a synthesis method for the preparation of the dimeric compound and a technetium-99m labeling method, comprising:

(1) synthesis of targeting ligand: piperazinyl quinolone is reacted with di-tert-butyl dicarbonate to form a tert-butoxycarbonyl protected intermediate I;

corresponding tert-butoxycarbonyl protected amino acid is reacted with pyrrolidine having different substituents, to form a dipeptide analogue, and tert-butoxycarbonyl is removed with trifluoroacetic acid to yield an intermediate II;

the intermediate I and the intermediate II are subjected to a condensation reaction, when the reaction is completed, a reaction solution is added dropwise into water to precipitate a solid, followed by filtration and drying, and then a tert-butoxycarbonyl protecting agent is removed with trifluoroacetic acid, so as to yield a targeting ligand III;

(2) synthesis of dimer: the targeting ligand is reacted with linkers ($L_1/L_2$) with different protecting groups, followed by a deprotection reaction to yield an intermediate IV;

the intermediate IV is reacted with Y with a protecting agent, followed by deprotection to yield an intermediate V;

the intermediate V is reacted with a ligand Q which can be chelated with technetium-99m to yield a prodrug targeting a fibroblast activation protein; and (3) the radionuclide technetium-99m labeled dimeric compound having a novel skeleton targeting the fibroblast activation protein according to the present disclosure can be prepared by labeling a prodrug compound targeting the fibroblast protein by an existing wet or dry method.

The present disclosure further provides a pharmaceutical composition, comprising the dimeric compound having a novel skeleton (piperazine quinolone) targeting fibroblast activation protein, a dimeric compound capable of being labelled by radionuclide technetium-99m and targeting fibroblast activation protein, a radionuclide technetium-99m labelled dimeric compound targeting fibroblast activation protein, or their pharmaceutically acceptable salts, hydrates, solvates, tautomers, and racemates and any pharmaceutically acceptable carrier and/or excipient composition.

The present disclosure further provides use of the dimeric compound having a novel skeleton (piperazine quinolone) targeting fibroblast activation protein, the dimeric compound capable of being labelled by radionuclide technetium-99m and targeting fibroblast activation protein, the radionuclide technetium-99m labelled dimeric compound targeting fibroblast activation protein, or their pharmaceutically acceptable salts, hydrates, solvates, tautomers, and racemates and any pharmaceutically acceptable carrier and/or excipient composition in the diagnosis or treatment of diseases characterized by FAP positivity.

Herein, the diseases characterized by FAP positivity include tumors with high FAP expression.

Herein, the diseases characterized by over-expression of fibroblast activation protein include, but are not limited to, various malignant tumors (breast cancer, lung cancer, pancreatic cancer, gastric cancer, liver cancer, colorectal cancer, thyroid cancer, etc.) and non-neoplastic diseases (myocardial infarction, rheumatoid arthritis, heart failure, kidney disease, pulmonary fibrosis, tissue remodeling, scarring, etc.).

The present disclosure further provides a kit, comprising a dimeric compound capable of being labelled by radionuclide technetium-99m and targeting fibroblast activation protein, a ligand capable of forming coordination with technetium-99m according to an existing method, a reductant, an additive, a stabilizer and instructions for diagnosing diseases.

Beneficial effects: compared with the prior art, the present disclosure has following significant advantages: 1. the present disclosure develops a brand-new piperazinyl quinolone-based skeleton, and an LAP-targeted probe derived from the brand-new skeleton has higher tumor uptake rate and imaging contrast; and 2. in order to further improve the tumor uptake rate, and optimize in vivo metabolic distribution, the present disclosure balances physicochemical properties of new molecules by screening and optimizing different linkers, and designs a dimer probe based on this type of skeleton. Compared with a monomer probe, this dimer probe has a greatly improved tumor uptake rate, faster tumor targeting and long retention capacity, so that it has quite low physiological uptake in non-targeted organs (liver, lung, kidney, pancreas, intestine, blood pool, thyroid, etc.), and has good pharmacokinetic properties and clinical application prospect.

DETAILED DESCRIPTION OF EMBODIMENTS

Figure 1:
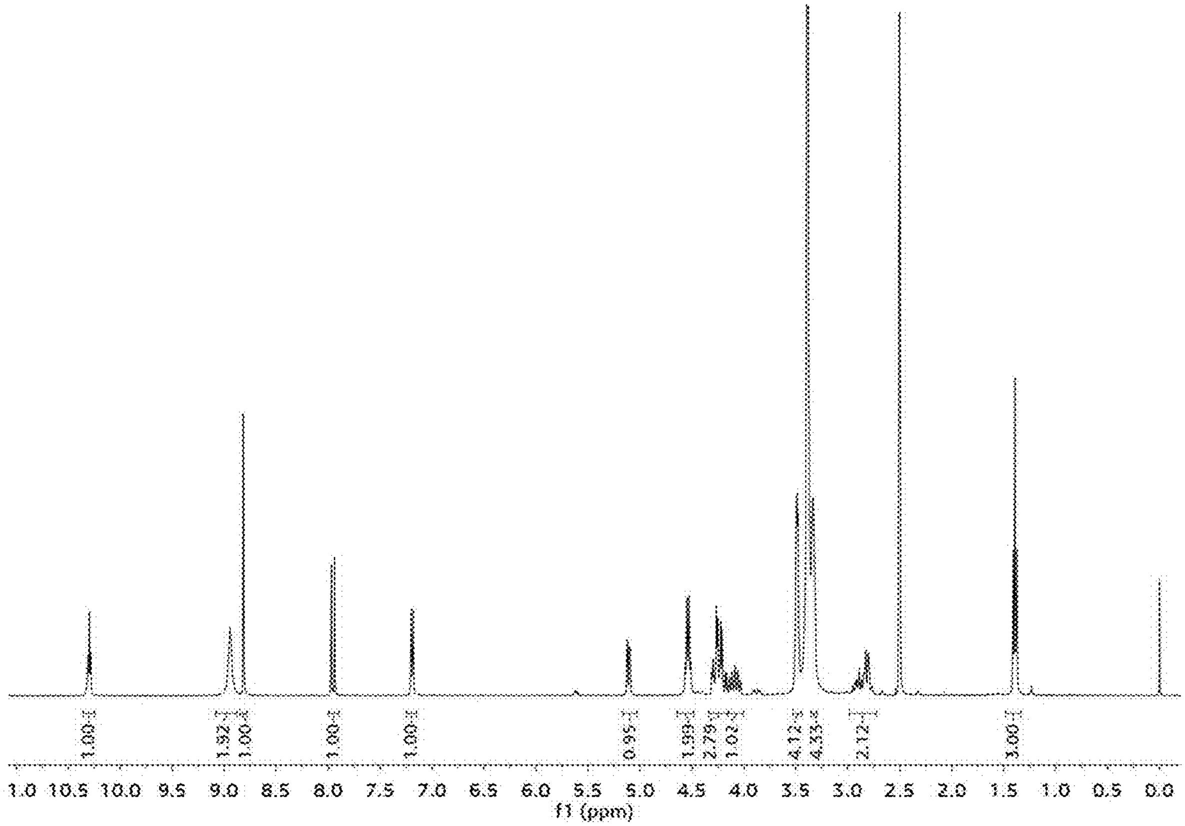
FIG. 1 is a proton nuclear magnetic resonance spectrum of compound a8 in Example 1 of the present disclosure.

Technical solutions of the present disclosure will be further described in conjunction with drawings below.

Synthesis methods in examples of the present disclosure include two parts: synthesis of targeting ligand and synthesis of dimer. Herein, compounds a1, a2, a5, a9, Boc-Glu, HYNIC-NHS, b9, c9, d5, i5, 4-pentynoic acid, k8, k9, and o5 were purchased from Shanghai Bide Pharmatech Co., Ltd; f9 was purchased from Jiangsu Aikon Biopharmaceutical R&D Co., Ltd.; U87MG cells were purchased from Nanjing Nanjing Cobioer Biosciences Co., Ltd.; nude mice (balb/c-nu) were purchased from Nanjing Anuokang Biotech Co., Ltd.; and sodium pertechnetate solution was ordered from Nanjing HTA Co., Ltd.

Example 1 Synthesis of Compound 1

1. Preparation of Targeting Ligand Compound a8:

Synthesis Route:

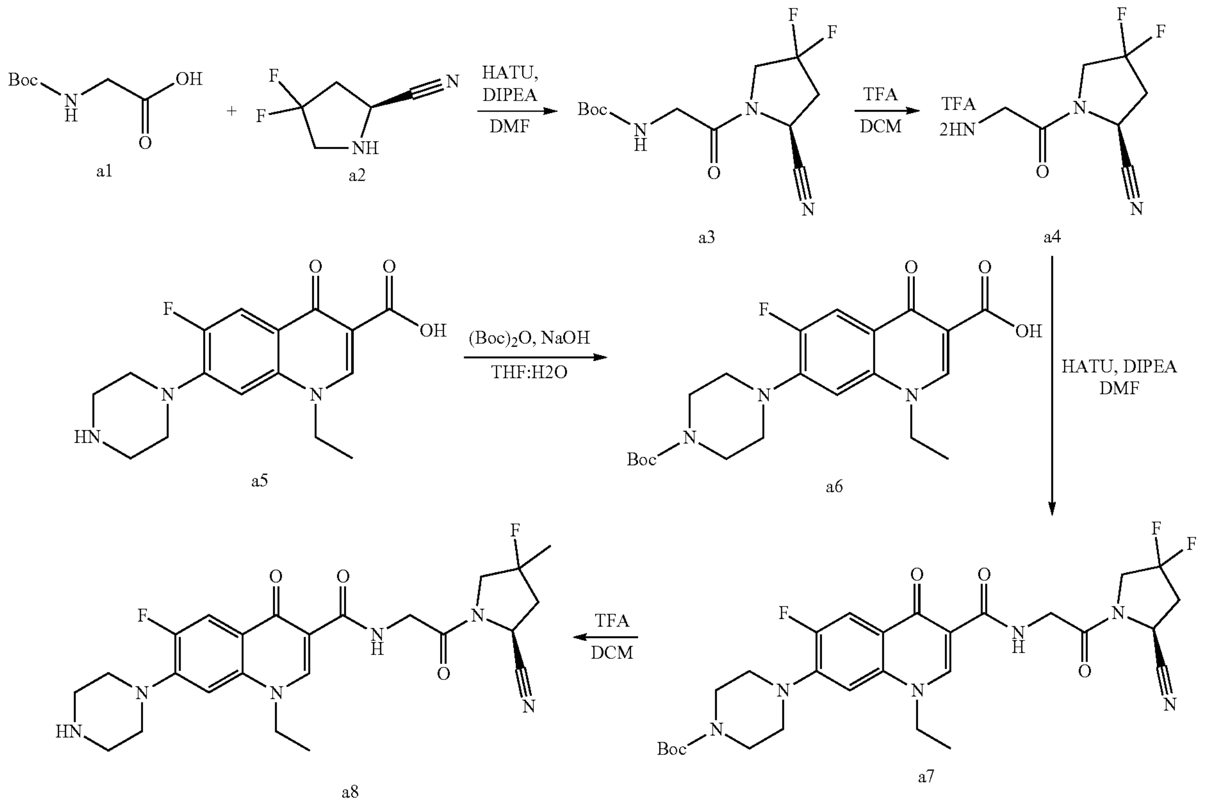

(1) Synthesis of Compound a3:

Dissolving N-Boc glycine a1 (175 mg, 1 mmol) and (S)-4,4-difluoropyrrolidine-2-carbonitrile hydrochloride a2 (132 mg, 1 mmol) in 5 mL of N,N dimethylformamide (DMF), adding 2-(7-Azabenzotriazol-1-yl)-N,N,N',N'-tetramethyluronium hexafluorophosphate (HATU, 418 mg, 1.1 mmol) and N,N-diisopropylethylamine (DIPEA, 521 μL, 3 mmol), reacting at room temperature for 2 h; detecting reaction to be complete by TLC, and concentrating a reaction solution; adding ethyl acetate for dissolution, washing with water and saturated saline in sequence, and drying an organic layer over anhydrous sodium sulfate and concentrating.

(2) Synthesis of Compound a4:

Adding the concentrated a3 to a mixed solution (DCM: TFA=10:1, v/v), reacting at room temperature for 1 h, concentrating a reaction solution, performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze drying to yield compound a4 (171 mg, yield 60%). MS(ESI): 190.20[M+H]$^+$.

(3) Synthesis of Compound a6:

Dissolving 1-ethyl-6-fluoro-1,4-dihydro-4-oxo-7-piperazine-3-quinoline carboxylic acid (a5, 1 g, 3.13 mmol) in 100 mL of mixed solution (tetrahydrofuran:water=1:1, v/v), adding 2 M NaOH (1.75 mL), stirring at room temperature until clear, adding $(Boc)_2O$ (0.75 g, 3.44 mmol), and stirring at room temperature overnight; upon completion of reaction, removing THF by vacuum concentration, adjusting pH1 to 7 with citric acid, precipitating a white solid, performing suction filtration, washing with 30 mL of water 3 times, and drying in vacuum to yield 1.3 g of the white solid, with yield 98%.

(4) Synthesis of Compound a7:

Dissolving a6 (419 mg, 1 mmol) and a4 (287 mg, 1 mmol) in 5 mL of DMF, adding HATU (418 mg, 1.1 mmol) and DIPEA (521 μL, 3 mmol), and reacting at room temperature for 2 h; detecting reaction to be complete by TLC, and concentrating a reaction solution; adding ethyl acetate for dissolution, washing with water and saturated saline in sequence, and drying an organic layer over anhydrous sodium sulfate and performing concentration; loading a sample by a wet method, and performing column chromatography separation and purification, to yield compound a7 (319 mg, yield 54%).

(5) Synthesis of Compound a8:

Adding a7 (590 mg, 1 mmol) to a mixed solution (dichloromethane:trifluoroacetic acid=10:1, v/v), reacting at room temperature for 1 h, concentrating a reaction solution, performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound a8 (490 mg, yield 100%). Proton nuclear magnetic resonance spectrum of compound a8 is as shown in FIG. 1. MS (ESI): 491.35[M+H]$^+$. $^1$H NMR (400 MHz, DMSO-$d_6$) δ 10.30 (t, J=5.2 Hz, 1H), 8.94 (s, 2H), 8.81 (s, 1H), 7.95 (d, J=13.2 Hz, 1H), 7.19 (d, J=7.2 Hz, 1H), 5.11 (dd, J=9.0, 2.9 Hz, 1H), 4.54 (q, J=7.0 Hz, 2H), 4.24 (qd, J=17.8, 5.2 Hz, 3H), 4.09 (dt, J=21.2, 10.3 Hz, 1H), 3.49 (dd, J=6.7, 3.6 Hz, 4H), 3.33 (s, 4H), 2.99-2.73 (m, 2H), 1.40 (t, J=7.1 Hz, 3H). $^{13}$C NMR (101 MHz, DMSO-$d_6$) δ 174.50, 168.61, 164.71, 158.30, 154.10, 151.64, 148.07, 143.84, 136.92, 122.69, 118.24, 112.33, 112.11, 110.71, 106.78, 52.05, 48.90, 47.19, 44.60, 43.22, 41.86, 36.92, 14.94.
2. Synthesis of Dimeric Compound 1:
Synthesis Route:
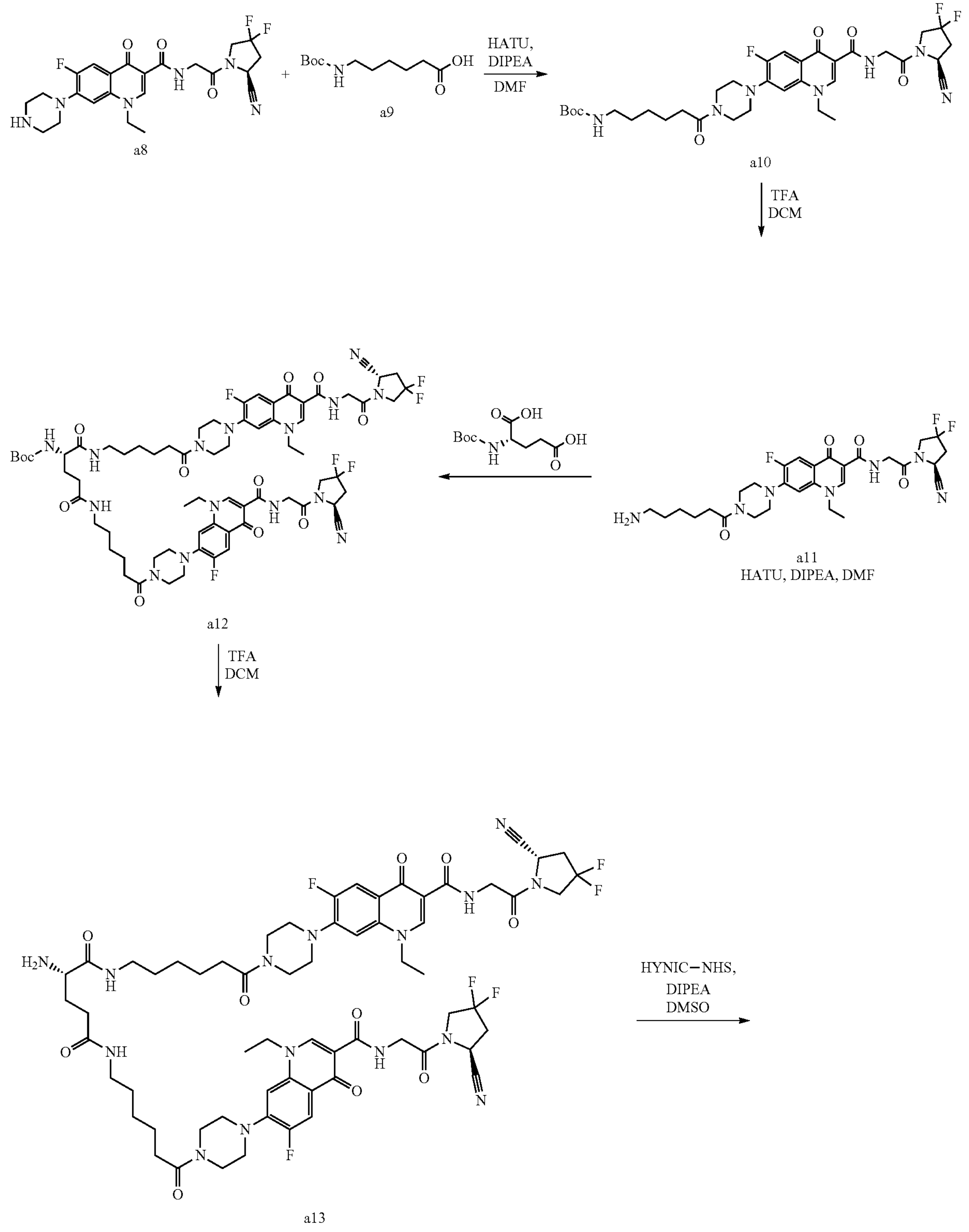
a8 + a9 → a10 → a11 → a12 → a13

-continued

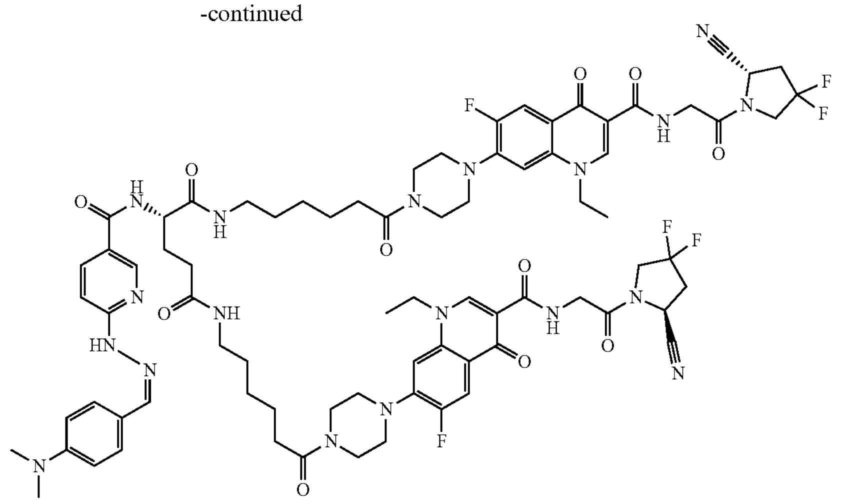

1

(1) Synthesis of Compound a10:

Dissolving a8 (100 mg, 0.2 mmol) and a9 (47 mg, 0.2 mmol) in 2 mL of DMF, adding HATU (83 mg, 0.24 mmol) and DIPEA (104 μL, 0.6 mmol), reacting at room temperature for 2 h; detecting reaction to be complete by TLC, and concentrating a reaction solution; adding ethyl acetate for dissolution, washing with water and saturated saline in sequence, and drying an organic layer over anhydrous sodium sulfate and performing concentration.

Figure 2:
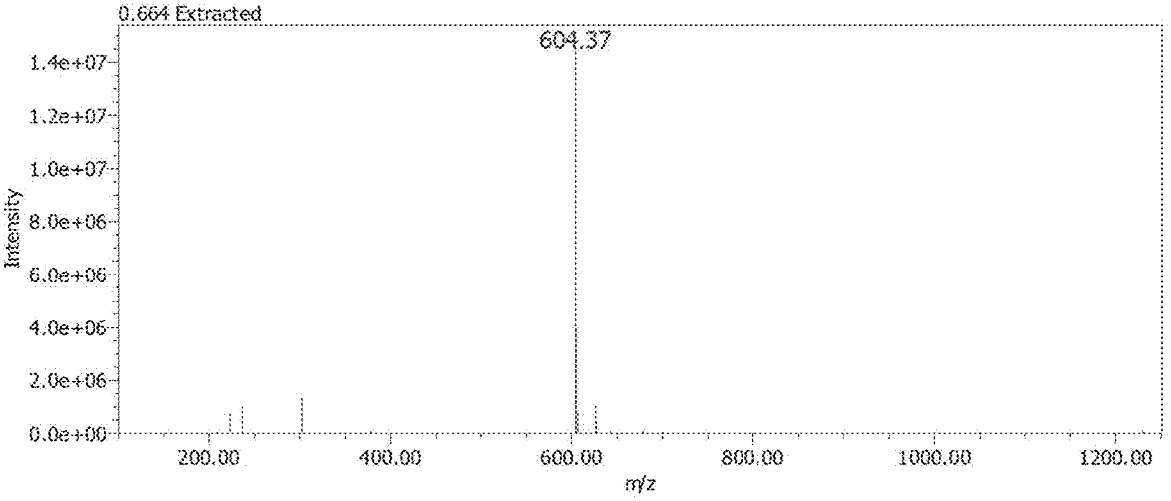
FIG. 2 is a mass spectrum of compound a11 in Example 1 of the present disclosure.

(2) Synthesis of Compound a11:

Adding concentrated a10 to a mixed solution (DCM: TFA=10:1, v/v), reacting at room temperature for 1 h, concentrating a reaction solution, performing separation and purification by C18 reversed phase liquid phase preparative chromatography (10% acetonitrile aqueous solution was increased to 50% in equal proportion, and an acetonitrile content was increased by 1% per minute, at a flow rate of 2 ml/min), and performing freeze-drying to yield compound a11 (96.68 mg, yield 80%). Mass spectrum of compound a11 is as shown in FIG. 2. MS: Ms=604.37.

(3) Synthesis of Compound a12:

Dissolving a11 (60.4 mg, 0.1 mmol) and Boc-Glu (12.35 mg, 0.05 mmol) in 1 mL of DMF, adding HATU (47.5 mg, 0.125 mmol) and DIPEA (52.16 μL, 0.3 mmol), reacting at room temperature for 14 h; loading a sample by a wet method, and performing column chromatography separation and purification (DCM:MeOH=100:2), to yield compound a12 (86.48 mg, yield 61%).

Figure 3:
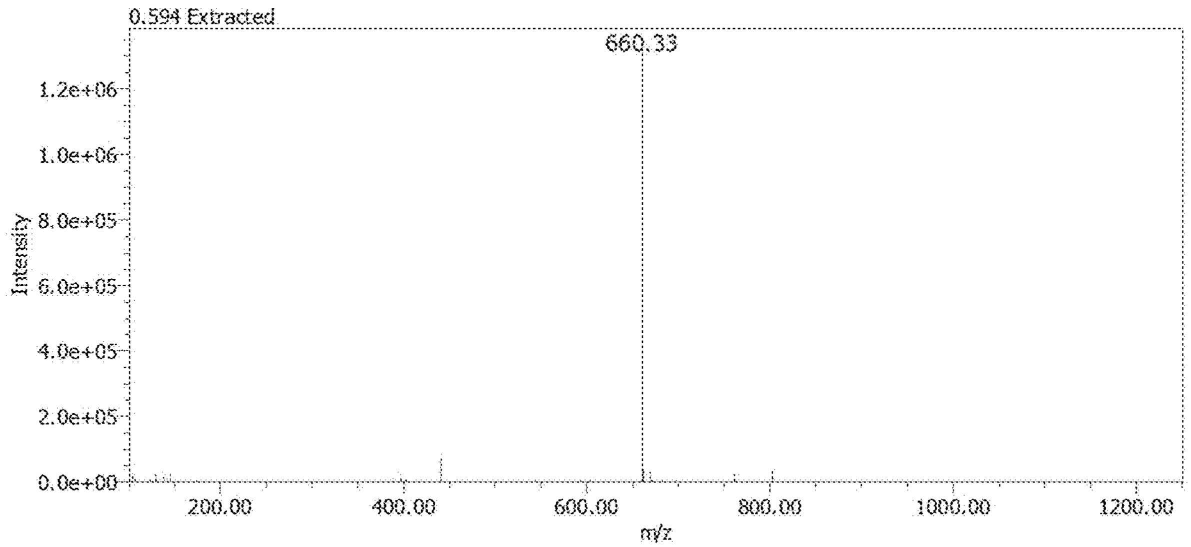
FIG. 3 is a mass spectrum of compound a13 in Example 1 of the present disclosure.

(4) Synthesis of Compound a13:

Adding concentrated a12 to a mixed solution (DCM: TFA=10:1, v/v), reacting at room temperature for 1 h, concentrating a reaction solution, performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound a13 (120.53 mg, yield 85%). Mass spectrum of compound a13 is as shown in FIG. 3. MS: Ms/2=660.3.

Figure 4:
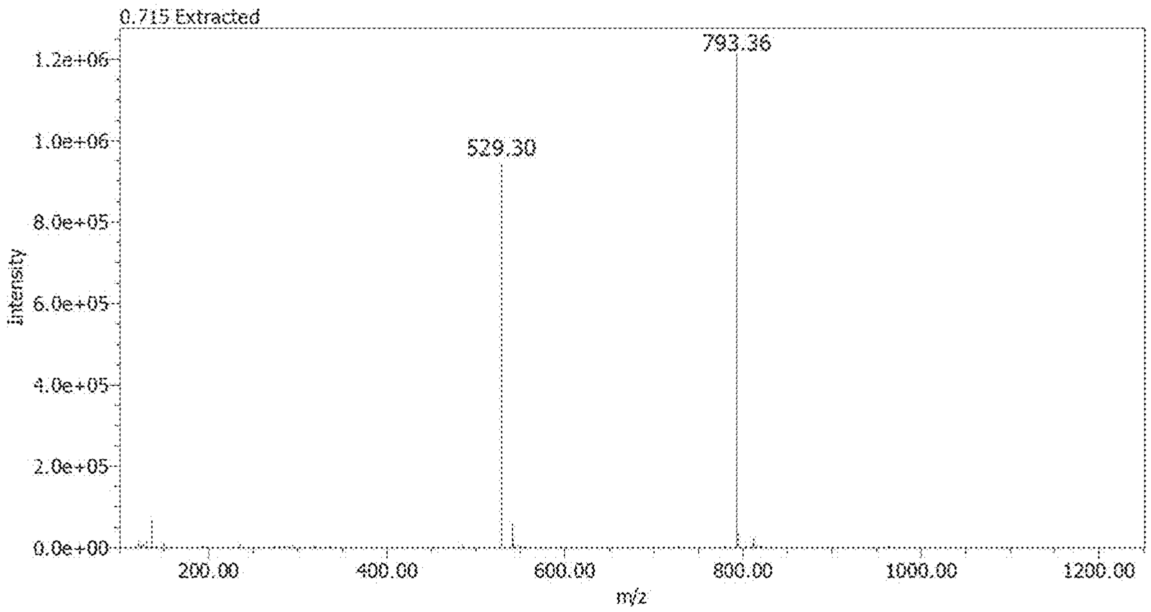
FIG. 4 is a mass spectrum of compound 1 in Example 1 of the present disclosure.

(5) Synthesis of Compound 1:

Dissolving freeze-dried a13 (131.7 mg, 0.1 mmol) and 6-hydrazinonicotinic acid N-hydroxysuccinimide ester hydrochloride (HYNIC-NHS, 7 mg, 0.2 mmol) in 2 mL of dimethyl sulfoxide (DMSO), adding DIPEA (69.54 μL, 0.4 mmol) dropwise, stirring at room temperature overnight; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound 1 (110.9 mg, yield 70%). Mass spectrum of compound 1 is as shown in FIG. 4. MS: Ms/2=793.36.

reacting at room temperature for 2 h, concentrating a reaction solution, performing separation and purification by C18 reversed phase liquid phase preparative chromatography Example 2 Synthesis of Compound 2

Synthesis Route:

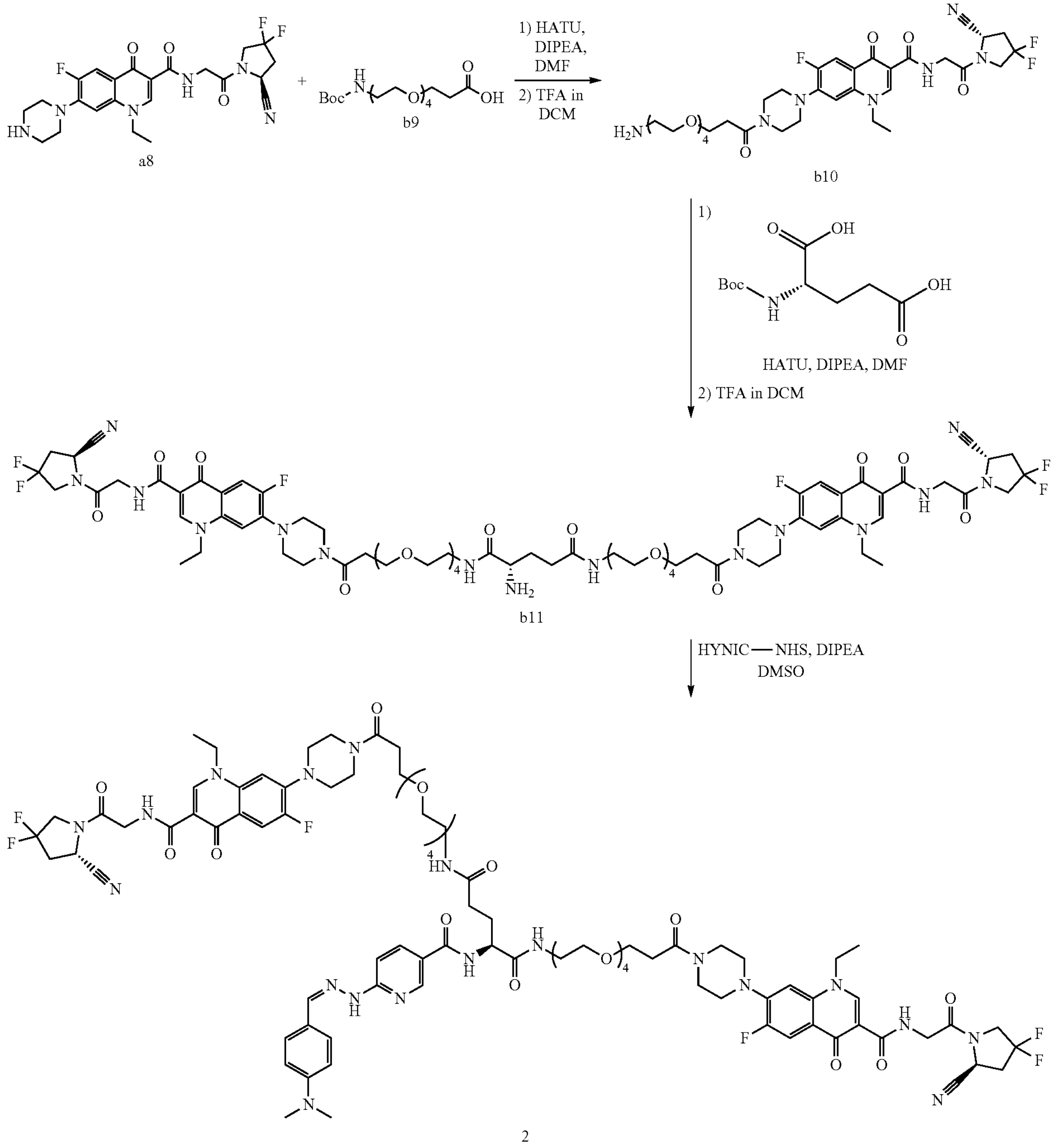

1. Synthesis of Compound b10:

Dissolving a8 (49 mg, 0.1 mmol) and 15-(Boc-amino)-4,7,10,13-tetraoxapentadecanoic acid b9 (36.8 mg, 0.1 mmol) in 1 mL of DMF, adding HATU (45.60 mg, 0.12 mmol) and DIPEA (52.16 μL, 0.3 mmol), and reacting at room temperature for 2 h; detecting reaction to be complete by TLC, and concentrating a reaction solution; adding ethyl acetate for dissolution, washing with water and saturated saline in sequence, and drying an organic layer over anhydrous sodium sulfate and performing concentration; adding concentrated solid to a mixed solution (DCM:TFA=10:1, v/v), (10% acetonitrile aqueous solution was increased to 50% in equal proportion, and an acetonitrile content was increased by 1% per minute, at a flow rate of 2 mL/min), and performing freeze-drying to yield compound b10 (44.4 mg, yield 60%).

2. Synthesis of Compound b11:

Dissolving b10 (159.1 mg, 0.1 mmol) and Boc-Glu (12.4 mg, 0.05 mmol) in 1 mL of DMF, adding HATU (47.5 mg, 0.125 mmol) and DIPEA (52.2 μL, 0.3 mmol), reacting at room temperature overnight; detecting reaction to be complete by TLC, and concentrating a reaction solution; adding ethyl acetate for dissolution, washing with water and saturated saline in sequence, and drying an organic layer over anhydrous sodium sulfate and performing concentration; loading a sample by a dry method, and performing column chromatography separation and purification (DCM: MeOH=100:2), performing concentration to obtain a white solid, adding the white solid to a mixed solution (DCM: TFA=10:1, v/v), reacting at room temperature for 1 h, and concentrating a reaction solution; performing separation and purification by C18 reversed phase liquid phase preparative chromatography, and performing freeze-drying to yield compound b11 (95.5 mg, yield 61%). MS: Ms/2=794.33.

(3) Synthesis of Compound 2:

Dissolving freeze-dried b11 (159.1 mg, 0.1 mmol) and HYNIC-NHS (76 mg, 0.2 mmol) in 2 mL of DMSO, adding DIPEA (69.54 μL, 0.4 mmol) dropwise, stirring at room temperature overnight; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound 2 (157.8 mg, yield 75%). MS: Ms/2=927.91.

Example 3 Synthesis of Compound 3

Synthesis Route:

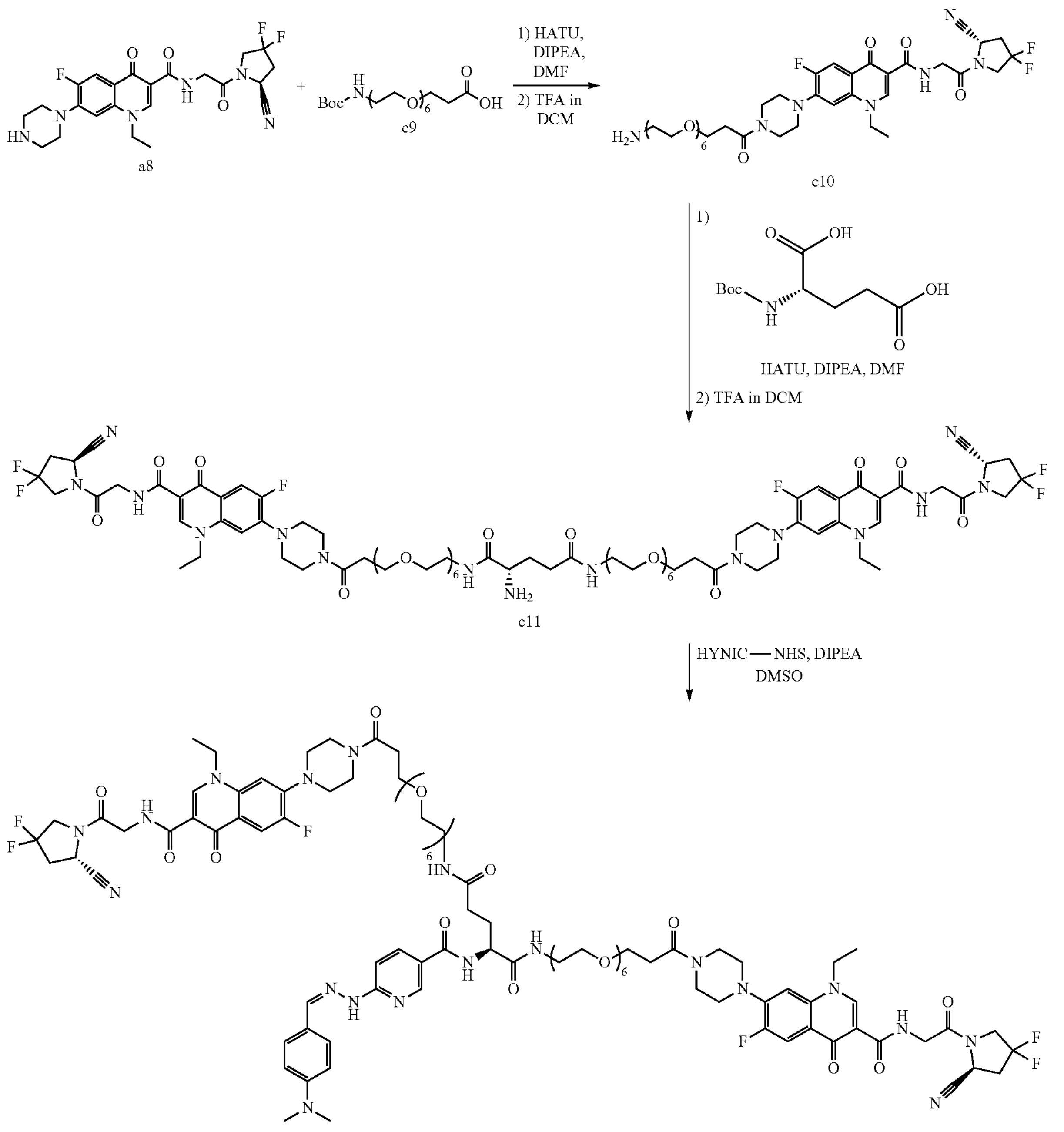

a8 c9 c10 c11

3

1. Synthesis of Compound c10:

Dissolving a8 (49 mg, 0.1 mmol) and c9 (45.8 mg, 0.1 mmol) in 1 mL of DMF, adding HATU (45.60 mg, 0.12 mmol) and DIPEA (52.16 μL, 0.3 mmol), reacting at room temperature for 3 h; detecting reaction to be complete by TLC, and concentrating a reaction solution; adding ethyl acetate for dissolution, washing with water and saturated saline in sequence, and drying an organic layer over anhydrous sodium sulfate and performing concentration; adding a concentrated solid to a mixed solution, reacting at room temperature for 2 h; detecting reaction to be complete by TLC, concentrating a reaction solution, performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound c10 (48.97 mg, yield 59%).

Figure 5:
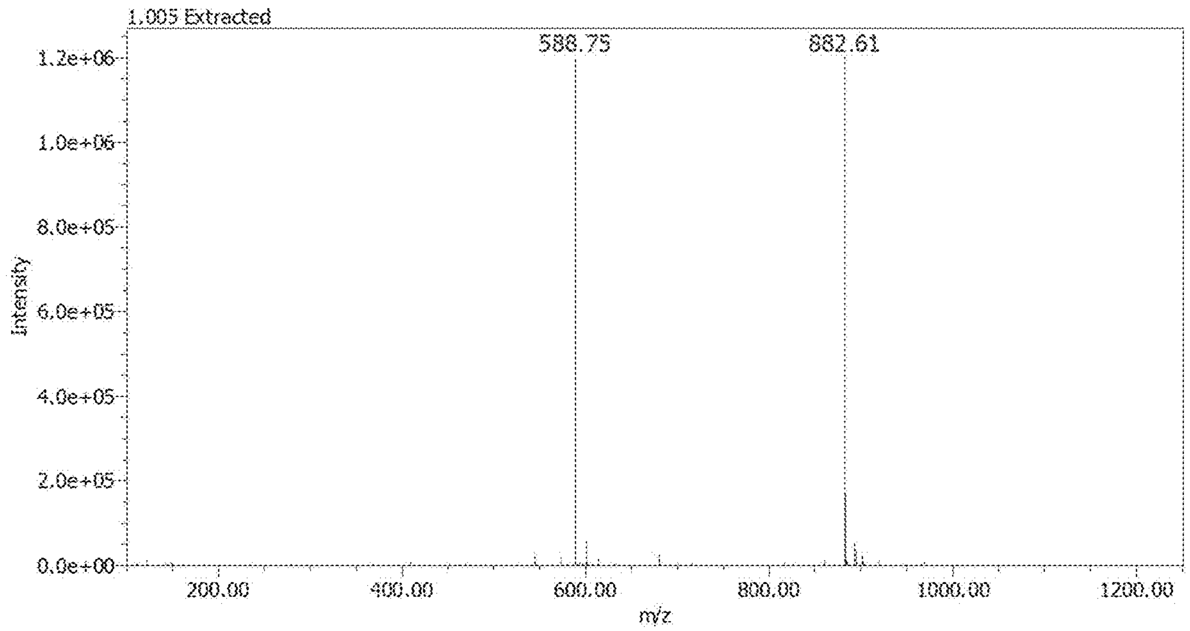
FIG. 5 is a mass spectrum of compound c11 in Example 3 of the present disclosure.

2. Synthesis of Compound c11:

Dissolving c10 (187.1 mg, 0.1 mmol) and Boc-Glu (12.4 mg, 0.05 mmol) in 1 mL of DMF, adding HATU (47.5 mg, 0.125 mmol) and DIPEA (52.2 μL, 0.3 mmol), reacting at room temperature overnight; detecting reaction to be complete by TLC, and concentrating a reaction solution; adding ethyl acetate for dissolution, washing with water and saturated saline in sequence, and drying an organic layer over anhydrous sodium sulfate and performing concentration; loading a sample by a dry method, and performing column chromatography separation and purification (DCM: MeOH=100:2, v/v), performing concentration to yield a white solid, adding the white solid to a mixed solution (DCM:TFA=10:1, v/v), reacting at room temperature for 1.5 h; detecting reaction to be complete by TLC, and concentrating a reaction solution; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze drying to yield compound c11 (112.3 mg, yield 60%). Mass spectrum of compound c11 is as shown in FIG. 5. MS: Ms/2=882.61.

Figure 6:
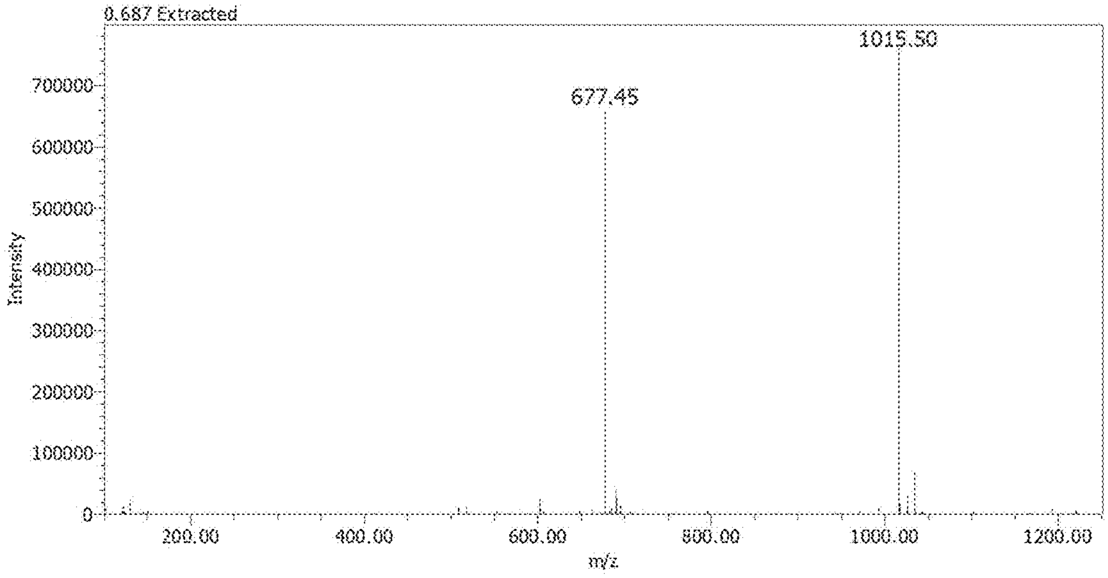
FIG. 6 is a mass spectrum of compound 3 in Example 3 of the present disclosure.

(3) Synthesis of Compound 3:

Dissolving freeze-dried c11 (187.1 mg, 0.1 mmol) and HYNIC-NHS (76 mg, 0.2 mmol) in 2 mL of DMSO, adding DIPEA (69.54 μL, 0.4 mmol) dropwise, stirring at room temperature overnight; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound 3 (158.4 mg, yield 78%). Mass spectrum of compound 3 is as shown in FIG. 6. MS: Ms/2=1015.50.

Example 4 Synthesis of Compound 4

Synthesis Route:

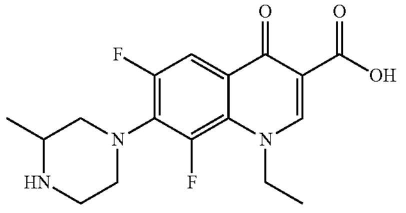

d5

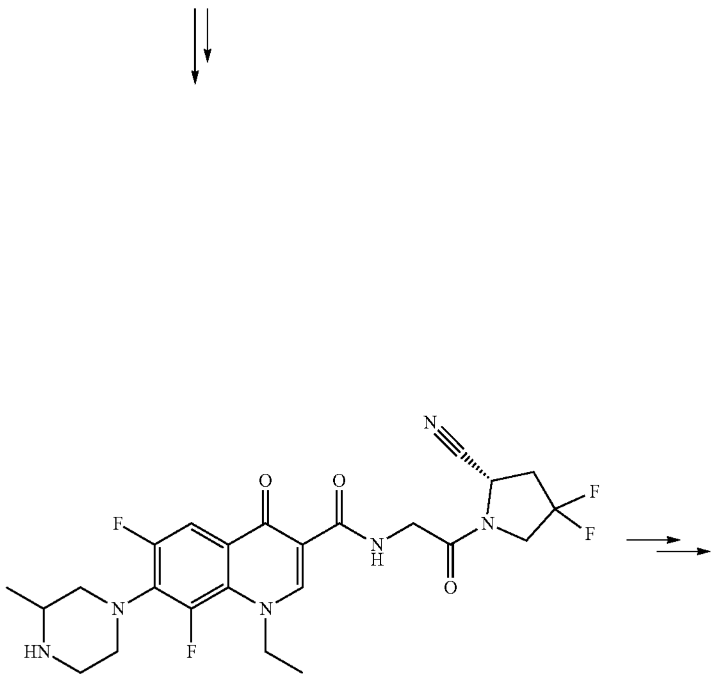

d8

-continued

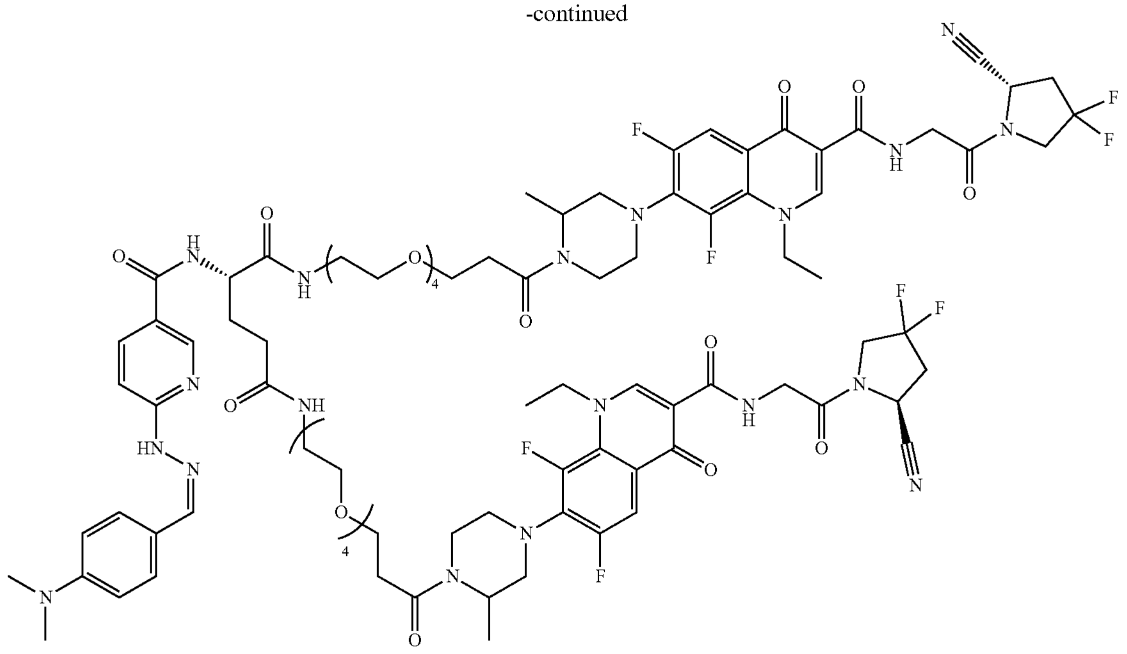

4

Figure 7:
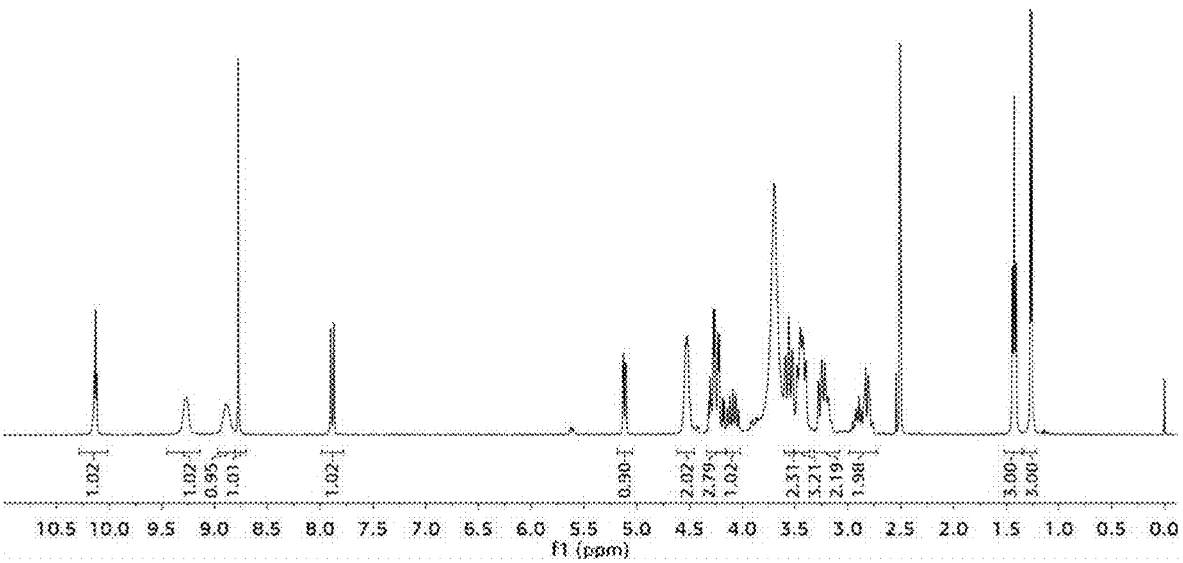
FIG. 7 is a proton nuclear magnetic resonance spectrum of compound d8 in Example 4 of the present disclosure.

1. Compound d8 was synthesized following the synthesis route of a8 in Example 1, wherein d8 can be obtained by replacing a5 with compound d5 in equal mole ratio, while other raw materials and proportions were identical. Proton nuclear magnetic resonance spectrum of compound d8 is as shown in FIG. 7. $^1$H NMR (400 MHz, DMSO-$d_6$) δ 10.13 (t, J=5.1 Hz, 1H), 9.27 (d, J=8.0 Hz, 1H), 8.97-8.81 (m, 1H), 8.77 (s, 1H), 7.89 (d, J=11.0 Hz, 1H), 5.12 (dd, J=9.1, 2.8 Hz, 1H), 4.62-4.45 (m, 2H), 4.25 (qd, J=17.8, 5.2 Hz, 3H), 4.09 (dt, J=21.1, 10.2 Hz, 1H), 3.60-3.51 (m, 2H), 3.50-3.36 (m, 3H), 3.32-3.08 (m, 2H), 2.99-2.72 (m, 2H), 1.43 (t, J=6.8 Hz, 3H). 1.27 (d, J=6.5 Hz, 3H).

2. Synthesis of Compound 4: Compound 4 was synthesized following the synthesis route in Example 2, wherein a8 was replaced with compound d8 in equal mole ratio, while other raw materials and proportions were identical. (Compound 4, MS: Ms/2=959.42)

Example 5 Synthesis of Compound 5

Compound 5 was synthesized following the synthesis route in Example 3, wherein compound 5 can be obtained by replacing a8 with compound d8 in equal mole ratio, while other raw materials and proportions were identical. (Compound 5, MS: Ms/2=1047.47)

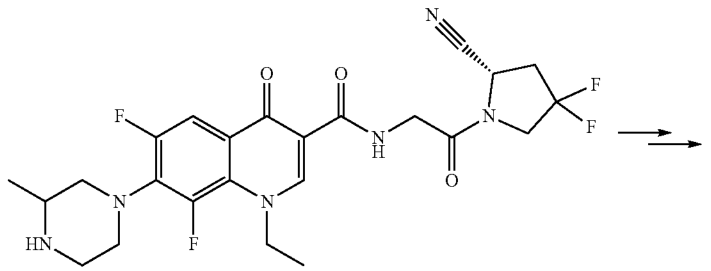

d8

-continued
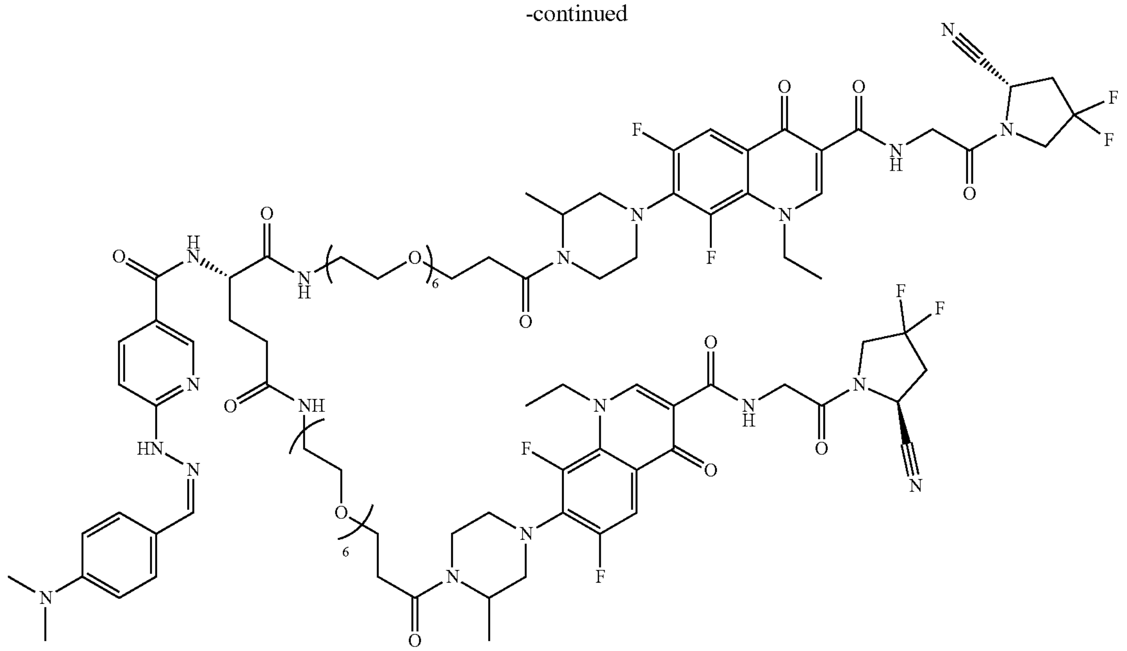
5
Example 6 Synthesis of Compound 6
Synthesis Route:
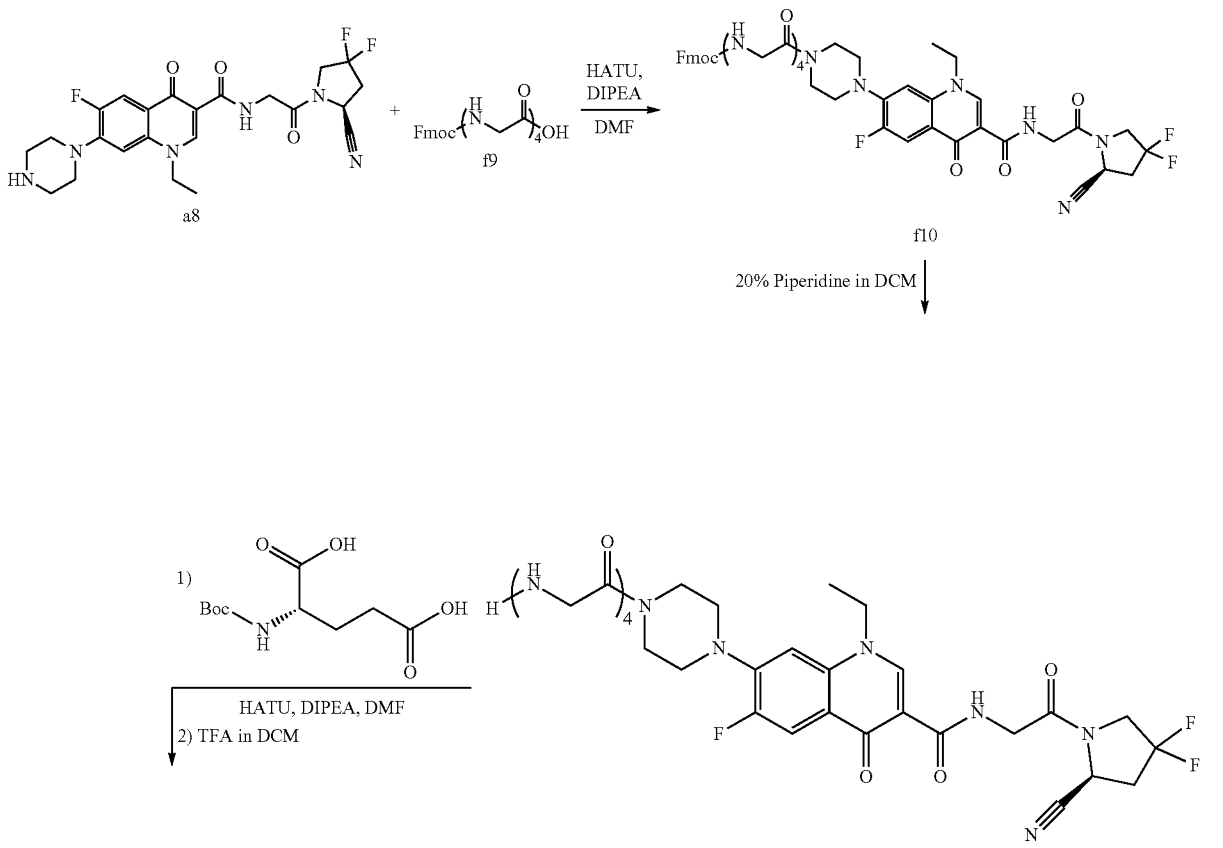
a8
f9
f10
f11

-continued

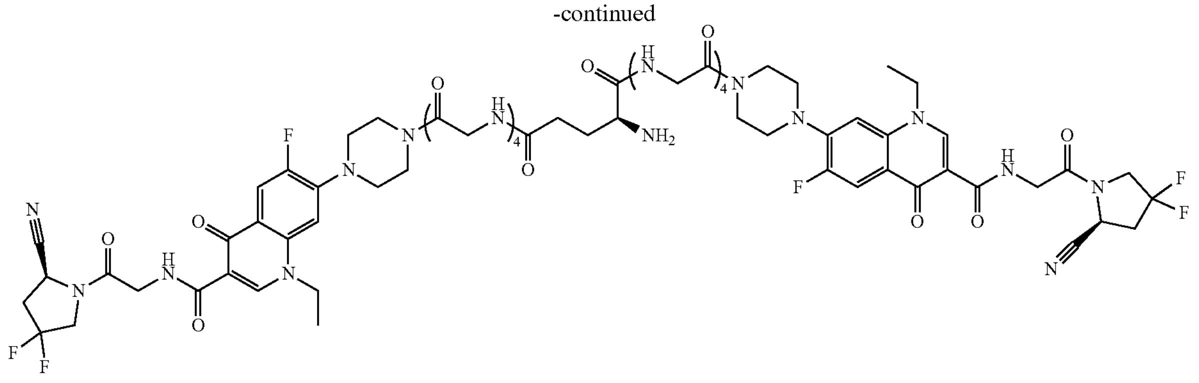

f12

HYNIC—NHS, DIPEA
DMSO

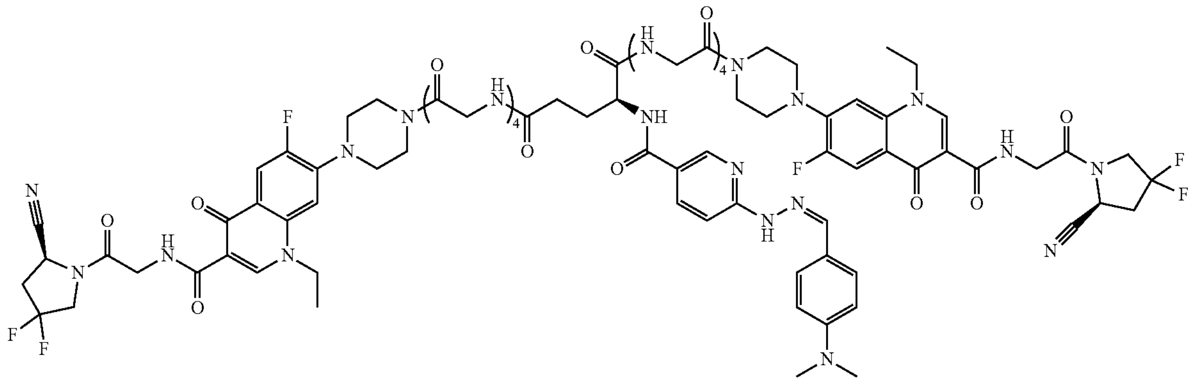

6

1. Synthesis of Compound f10:

Dissolving a8 (49 mg, 0.1 mmol) and f9 (51.48 mg, 0.11 mmol) in 1 mL of DMF, adding HATU (49.4 mg, 0.13 mmol) and DIPEA (52.16 μL, 0.3 mmol), reacting at room temperature for 6 h; detecting reaction to be complete by TLC, adding a reaction solution dropwise to 20 mL of ice water to precipitate a solid, performing suction filtration, and drying under reduced pressure to yield compound f10 (65.8 mg, yield 70%).

Figure 8:
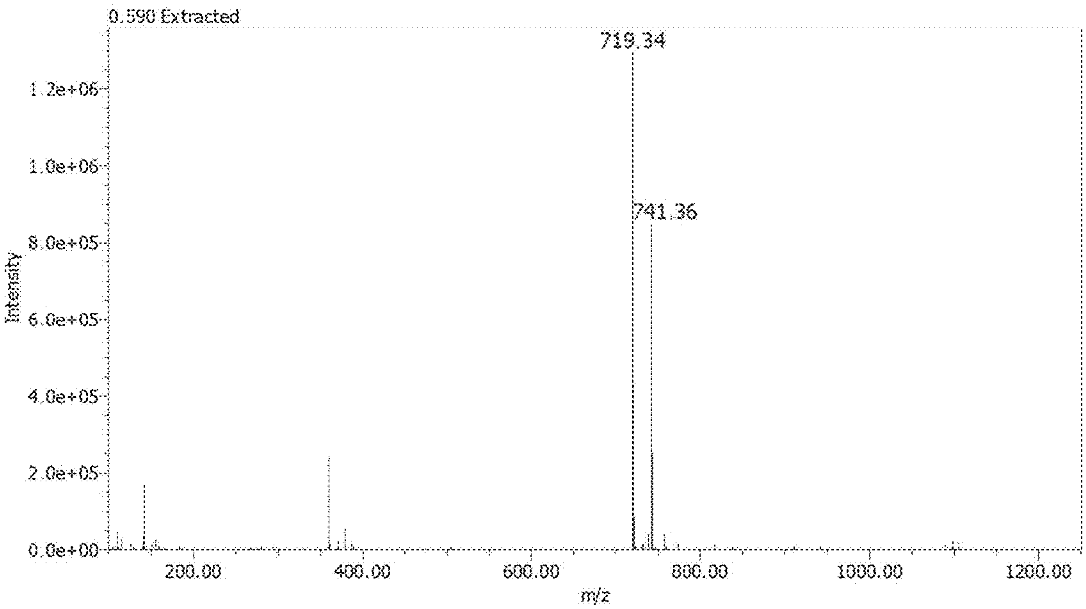
FIG. 8 is a mass spectrum of compound f11 in Example 6 of the present disclosure.

2. Synthesis of Compound f11:

Adding f10 obtained from drying under reduced pressure to 2 mL of mixed solution (piperidine:DCM=1:5, v/v), and reacting at room temperature for 3 h; detecting reaction to be complete by TLC, concentrating a reaction solution to remove piperidine; loading a sample by a dry method, and performing column chromatography separation and purification (DCM:MeOH=100:2), to yield compound f11 (42.69 mg, yield 85%). Mass spectrum of compound f11 is as shown in FIG. 8. MS: Ms=719.34.

Figure 9:
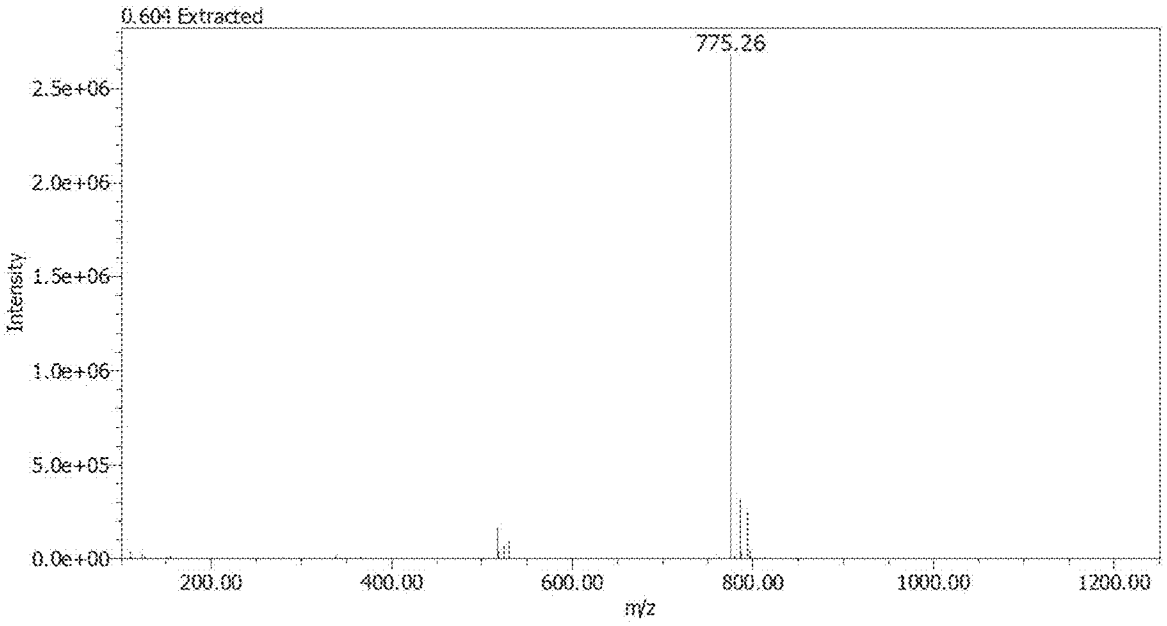
FIG. 9 is a mass spectrum of compound f12 in Example 6 of the present disclosure.

3. Synthesis of Compound f12:

Dissolving f11 (71.7 mg, 0.1 mmol) and Boc-Glu (12.4 mg, 0.05 mmol) in 1 mL of DMF, adding HATU (47.5 mg, 0.125 mmol) and DIPEA (52.2 μL, 0.3 mmol), reacting at room temperature for 14 h; loading a sample by a wet method, and performing column chromatography separation and purification, performing concentration to obtain a white solid, adding the white solid to a mixed solution (DCM: TFA=10:1, v/v), reacting at room temperature for 1 h, and concentrating a reaction solution; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound f12 (94.25 mg, yield 61% C4). Mass spectrum of compound f12 is as shown in FIG. 9. MS: Ms/2=775.26).

Figure 10:
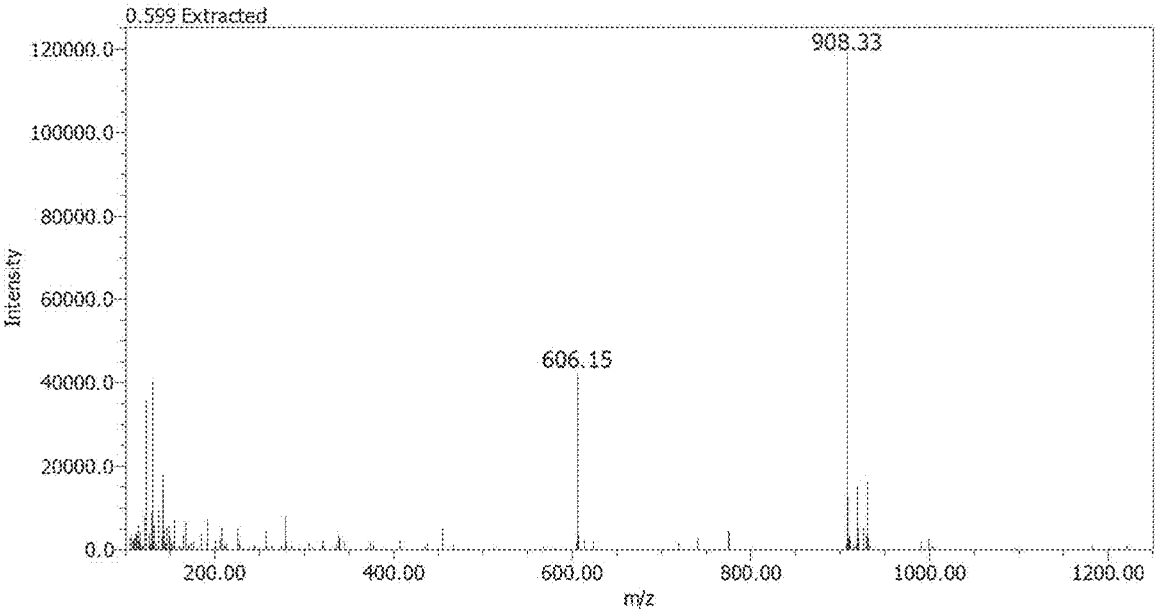
FIG. 10 is a mass spectrum of compound 6 in Example 6 of the present disclosure.

4. Synthesis of Compound 6:

Dissolving freeze-dried f12 (154.5 mg, 0.1 mmol) and HYNIC-NHS (76 mg, 0.2 mmol) in 2 mL of DMSO, adding DIPEA (69.5 μL, 0.4 mmol) dropwise, stirring at room temperature overnight; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound 6 (108.2 mg, yield 70%). Mass spectrum of compound 6 is as shown in FIG. 10. MS: Ms/2=908.33.

Example 7 Synthesis of Compound 7

Compound 7 was synthesized following the synthesis route in Example 6, wherein compound 7 can be obtained by replacing a8 with compound d8 in equal mole ratio, while other raw materials and proportions were identical. (Compound 7, MS: Ms/2=940.84)

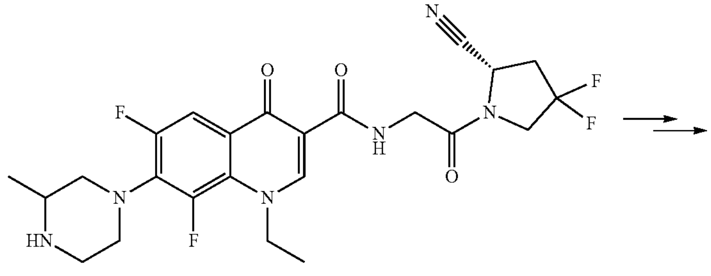
d8
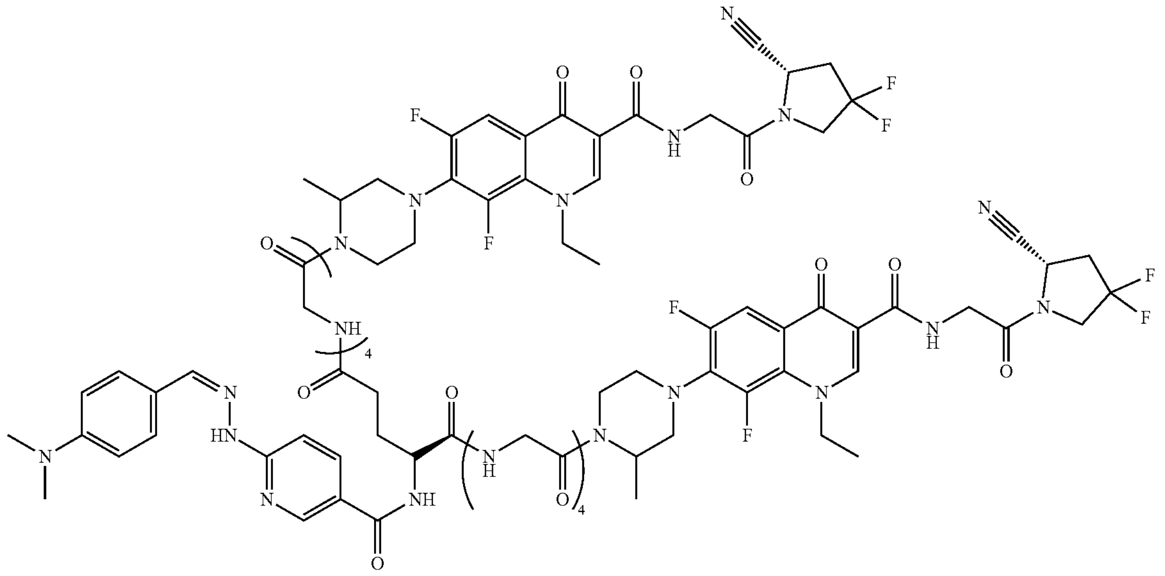
7
Example 8 Synthesis of Compound 8
Compound 8 was synthesized following the synthesis route in Example 3, wherein compound 8 can be obtained by replacing a8 with compound d8 in equal mole ratio, while other raw materials and proportions were identical. (Compound 8, MS: Ms/2=1054.48)
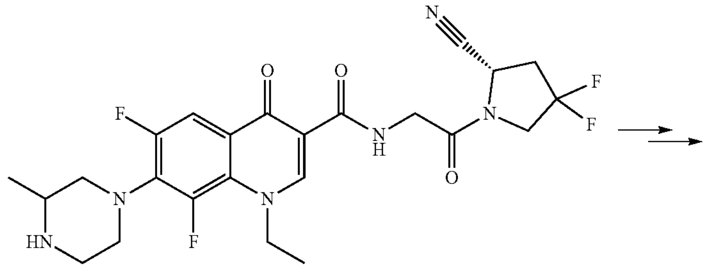
d8

-continued
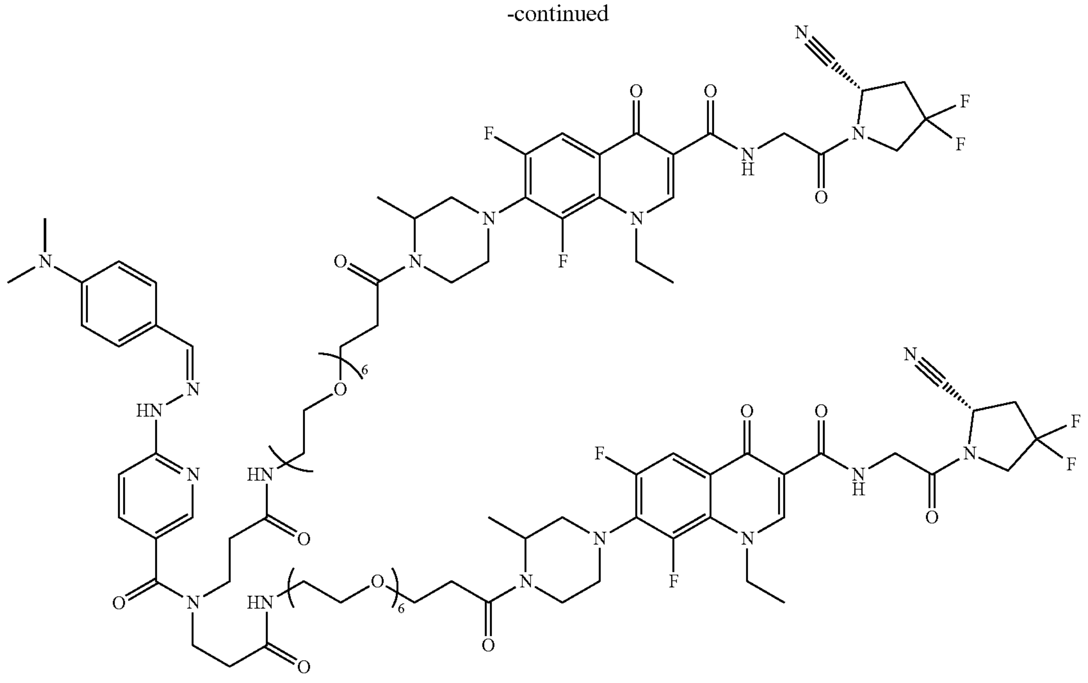
8
Example 9 Synthesis of Compound 9
Synthesis Route:
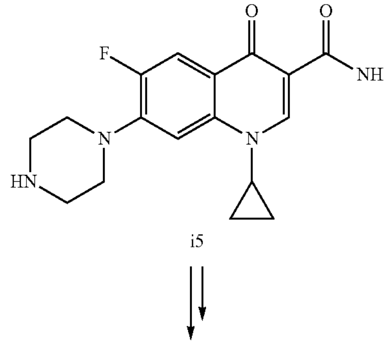
i5
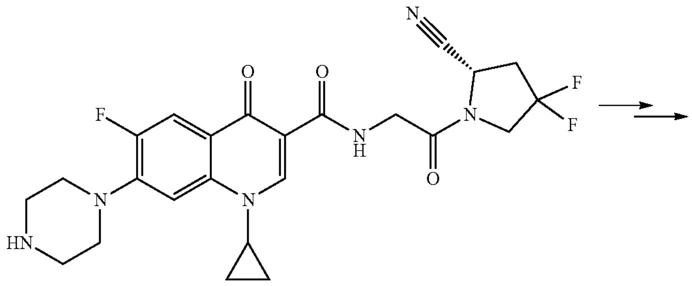
i8

-continued

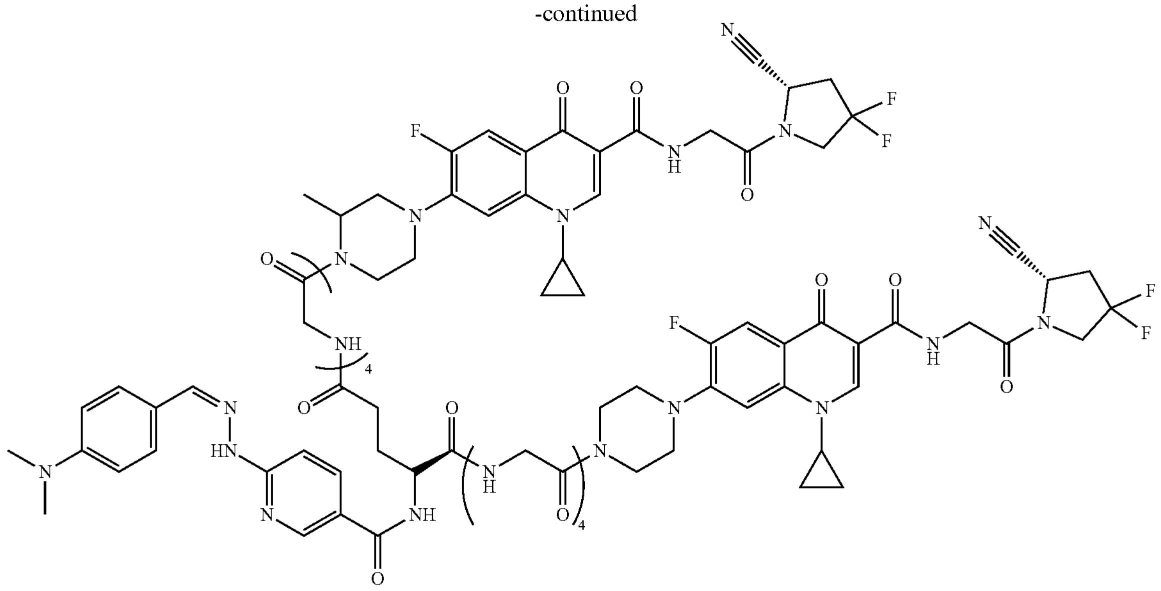

9

Figure 11:
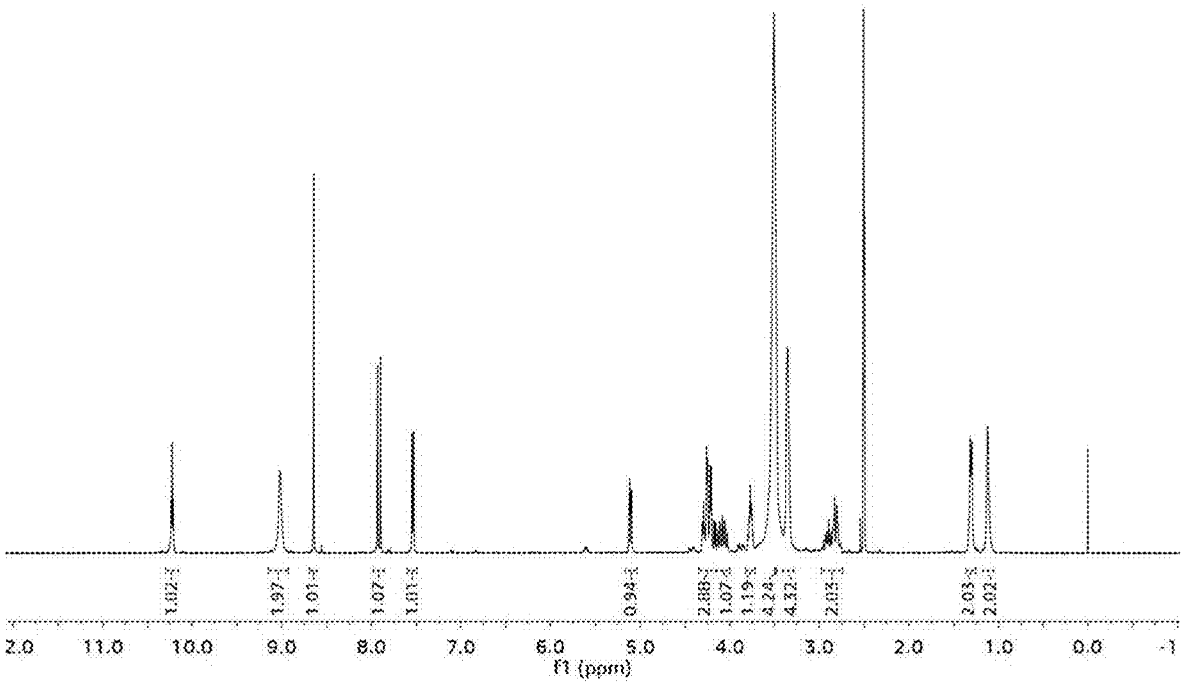
FIG. 11 is a proton nuclear magnetic resonance spectrum of compound i8 in Example 9 of the present disclosure.

Compound 98 was synthesized following the synthesis route in Example a8, wherein i8 can be obtained by replacing a8 with compound i8 in equal mole ratio, while other raw materials and proportions were identical. Proton nuclear magnetic resonance spectrum of compound i8 is as shown in FIG. 11. $^1$H NMR (400 MHz, DMSO-$d_6$) δ 10.22 (t, J=5.2 Hz, 1H), 9.02 (s, 2H), 8.65 (s, 1H), 7.92 (d, J=13.2 Hz, 1H), 7.54 (d, J=7.4 Hz, 1H), 5.11 (dd, J=9.1, 2.8 Hz, 1H), 4.24 (qd, J=17.8, 5.2 Hz, 3H), 4.08 (dt, J=21.2, 10.2 Hz, 1H), 3.77 (tt, J=7.2, 4.1 Hz, 1H), 3.49 (d, J=6.4 Hz, 4H), 3.35 (s, 4H), 2.98-2.74 (m, 2H), 1.31 (d, J=6.5 Hz, 2H), 1.12 (d, J=3.6 Hz, 2H).

Compound 9 was synthesized following the synthesis route in Example 6, wherein 9 can be obtained by replacing a8 with compound i8 in equal mole ratio, while other raw materials and proportions were identical. (Compound 9, MS: Ms/2=920.83)

Example 10 Synthesis of Compound 10

Compound 10 was synthesized following the synthesis route in Example 3, wherein 10 can be obtained by replacing a8 with compound i8 in equal mole ratio, while other raw materials and proportions were identical. (Compound 10, MS: Ms/2=1052.47)

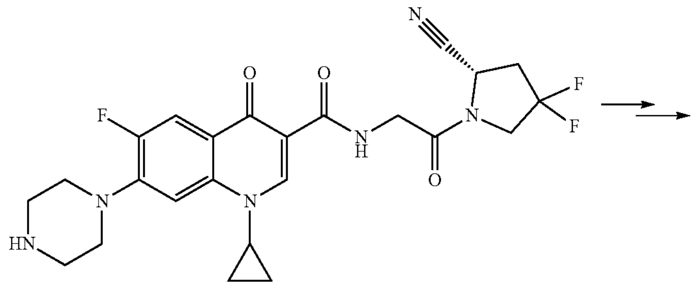

i8

-continued
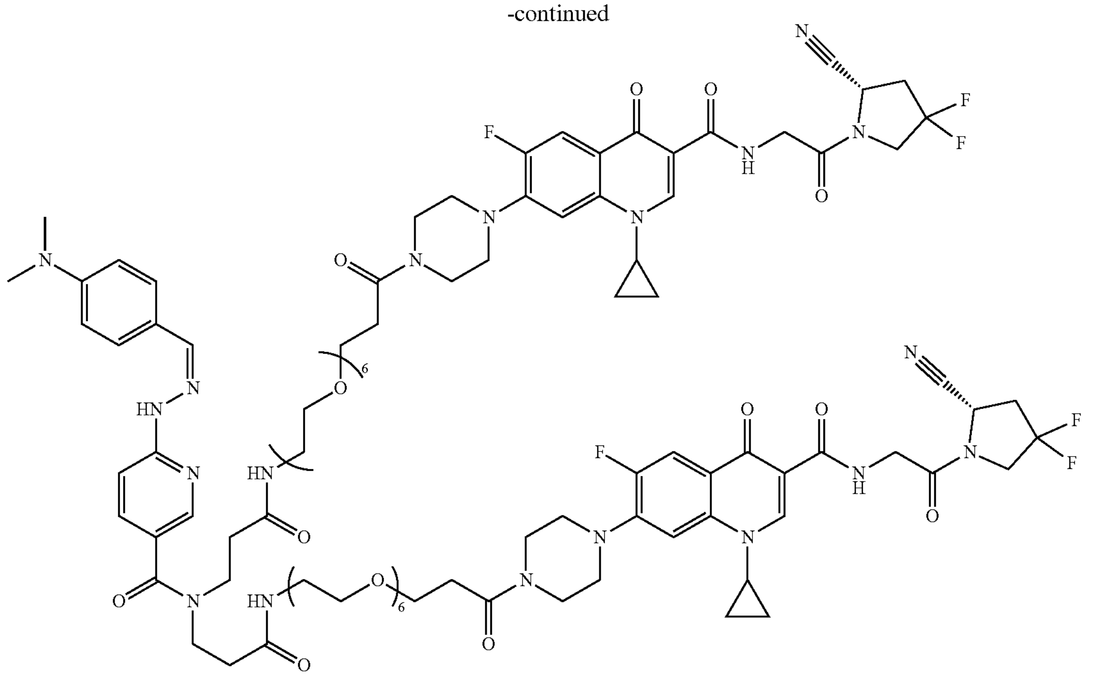
10
Example 11 Synthesis of Compound 11
Synthesis Route:
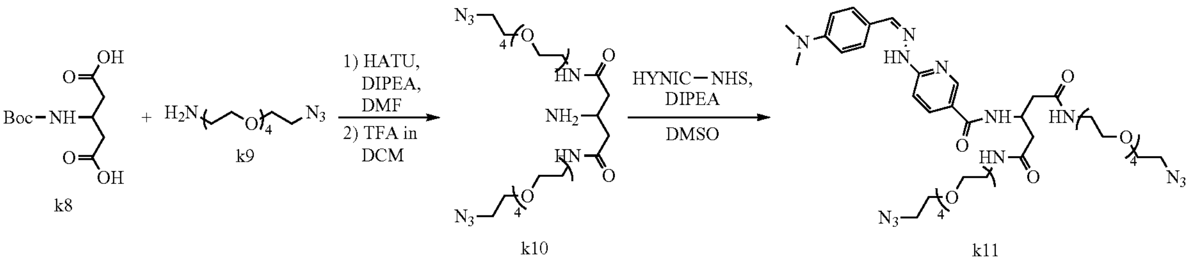
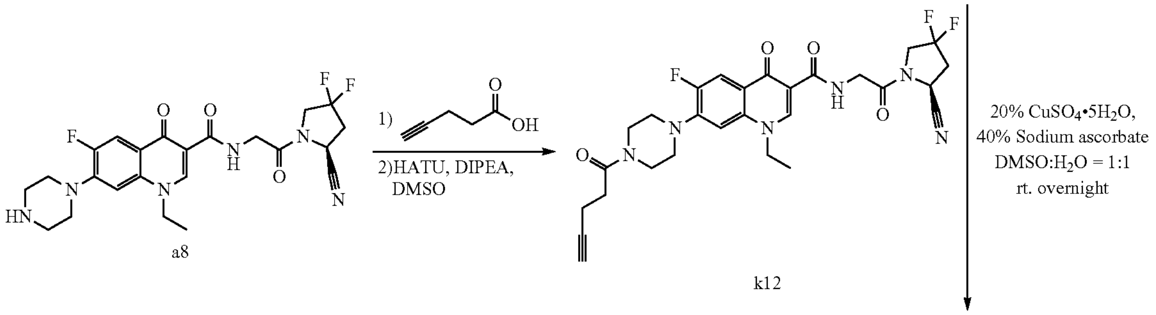

-continued

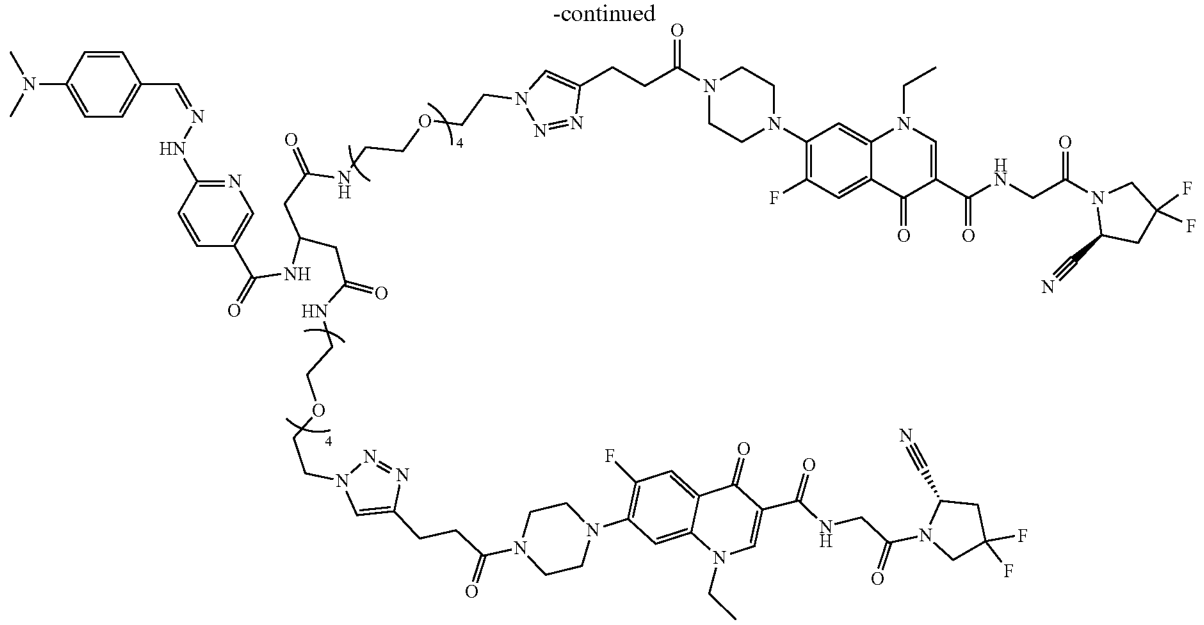

11

1. Synthesis of Compound k10:

Dissolving k8 (24.7 mg, 0.1 mmol) and k9 (52.4 mg, 0.2 mmol) in 1 mL of DMF, adding HATU (45.60 mg, 0.12 mmol) and DIPEA (52.16 μL, 0.3 mmol), reacting at room temperature for 3 h; performing separation and purification by C18 reversed phase liquid phase preparative chromatography, and performing freeze-drying to obtain a solid compound; adding the freeze-dried solid compound to a mixed solution (DCM:TFA=10:1, v/v), reacting at room temperature for 1 h, concentrating a reaction solution, performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound k10 (40.6 mg, yield 64%).

2. Synthesis of Compound k11:

Dissolving freeze-dried k10 (63.5 mg, 0.1 mmol) and HYNIC-NHS (7 mg, 0.2 mmol) in 2 mL of DMSO, adding DIPEA (69.54 μL, 0.4 mmol) dropwise, stirring at room temperature overnight; performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound k11 (63.1 mg, yield 70%).

3. Synthesis of Compound k12:

Dissolving a8 (49.0 mg, 0.1 mmol) and 4-pentynoic acid in 1 mL of DMF, adding HATU (41.8 mg, 0.11 mmol) and DIPEA (52.16 μL, 0.3 mmol), reacting at room temperature for 2 h; detecting reaction to be complete by TLC, and performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min).

Figure 12:
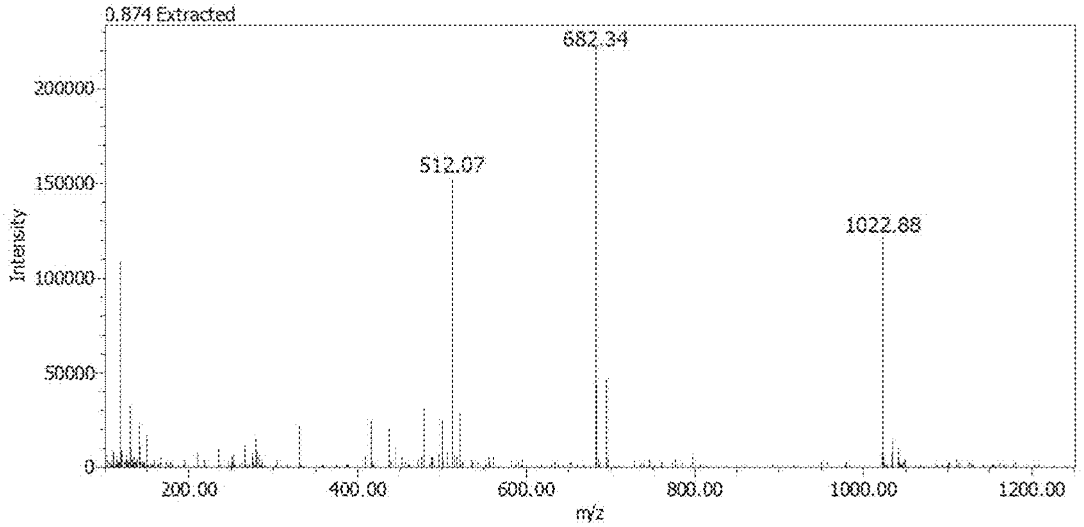
FIG. 12 is a mass spectrum of compound 11 in Example 11 of the present disclosure.

4. Synthesis of Compound 11:

Preparing a $Cu^+$ aqueous solution with $CuSO_4 \cdot 5H_2O$ and sodium ascorbate; dissolving k11 (90.2 mg, 0.1 mmol) and k12 (114 mg, 0.2 mmol) in 1.5 mL of mixed solution (DMSO: H2O=1:1, v/v), adding a catalytic amount of the $Cu^+$ aqueous solution, and reacting at room temperature for 4 h; detecting reaction to be complete by TLC, performing separation and purification by C18 reversed phase liquid phase preparative chromatography (10% acetonitrile aqueous solution was increased to 50% in equal proportion, and an acetonitrile content was increased by 1% per minute, at a flow rate of 2 mL/min), and performing freeze-drying to yield compound 11. Mass spectrum of compound 11 is as shown in FIG. 12. MS: Ms/2=1022.88.

Example 12 Synthesis of Compound 12

Compound 12 was synthesized following the synthesis route in Example 11, wherein 12 can be obtained by replacing a8 with compound d8 in equal mole ratio, while other raw materials and proportions were identical (Compound 12, MS: Ms/2=1054.39)

Structural formula of compound 12 is as follows:

12

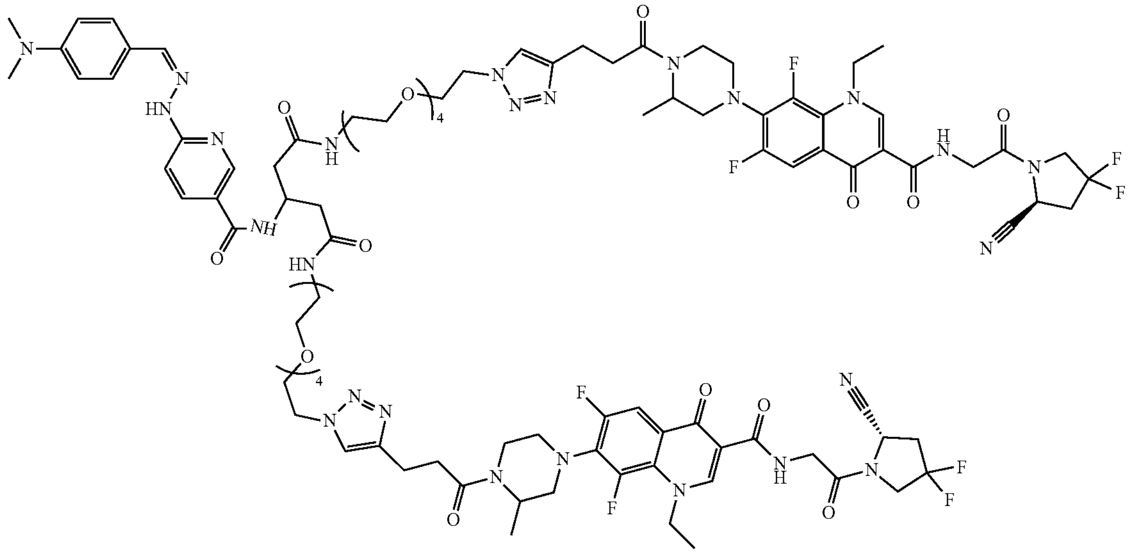

Example 13 Synthesis of Compound 13

Compound 13 was synthesized following the synthesis route in Example 11, wherein 13 can be obtained by replacing a8 with compound i8 in equal mole ratio, while other raw materials and proportions were identical (Compound 13, MS: Ms/2=1034.88)

Structural formula of the compound 13 is as follows:

Example 14 Synthesis of Compound 14

1. Compound o8 was synthesized following the synthesis route in Example a8, wherein o8 can be obtained by replacing a5 with compound o5 in equal mole ratio, while other raw materials and proportions were identical.

2. Compound 14 was synthesized following the synthesis route in Example 11, wherein 14 can be obtained by replac-

13

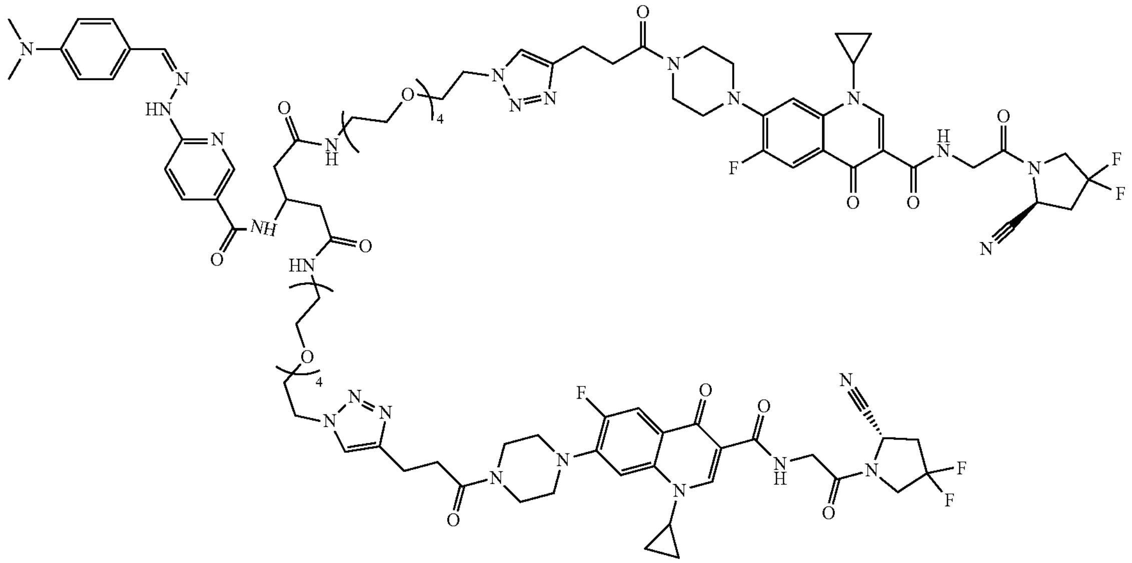

ing a8 with compound o8 in equal mole ratio, while other raw materials and proportions were identical. (Compound 14, MS: Ms/2=1052.33)
Structural formula of the compound 14 is as follows:
14
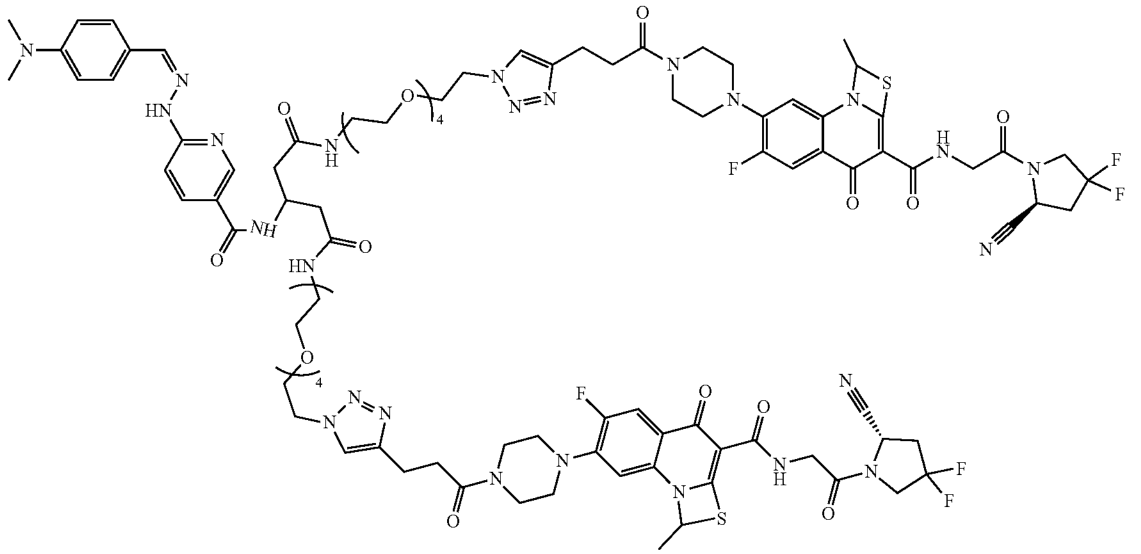
Example 15 Synthesis of Compound 15
Synthesis Route:
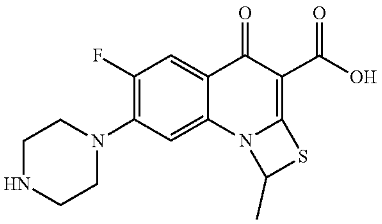
o5
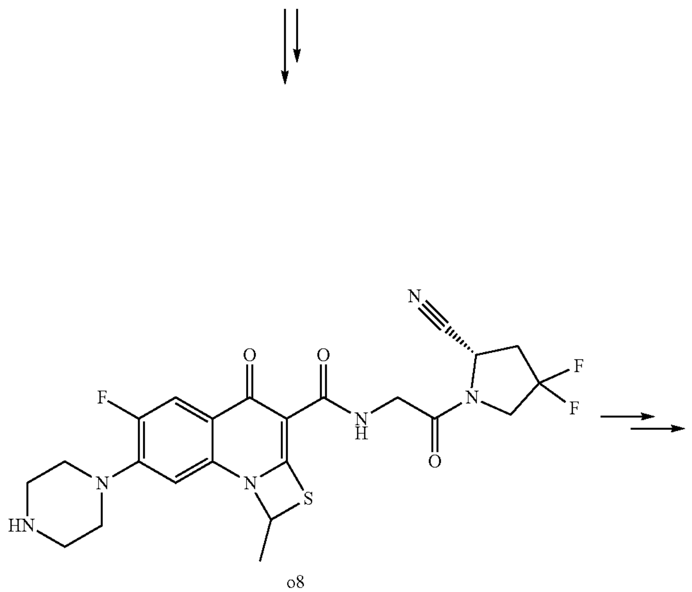
o8

-continued

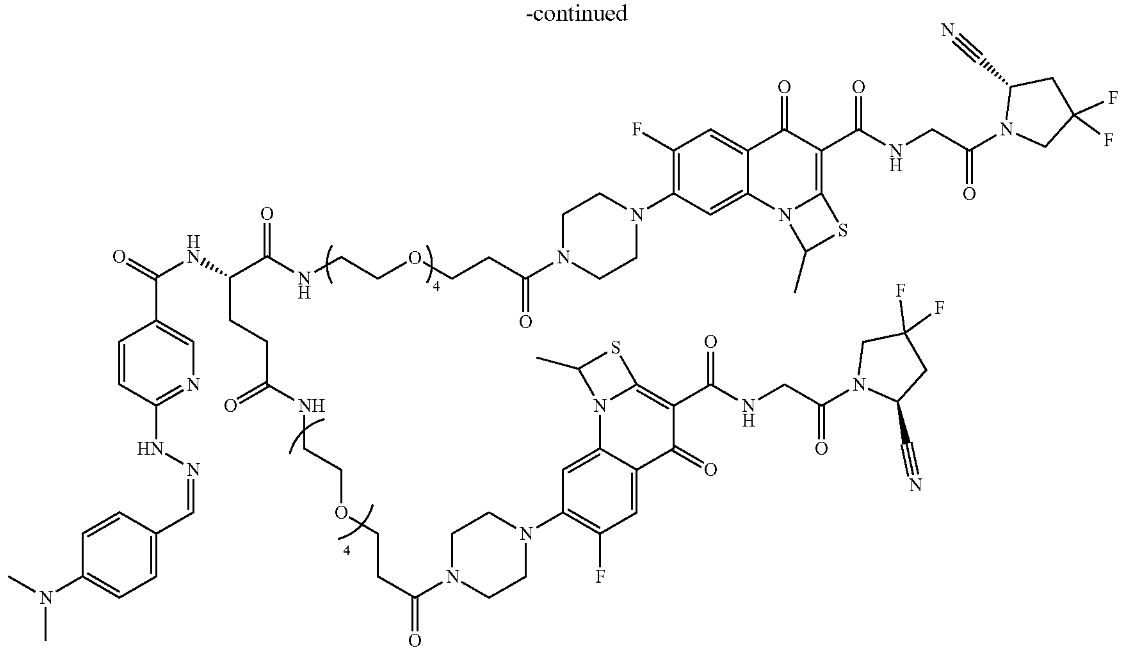

15

1. Compound o8 was synthesized following the synthesis route in Example a8, wherein o8 can be obtained by replacing a5 with compound o5 in equal mole ratio, while other raw materials and proportions were identical.

2. Compound 15 was synthesized following the synthesis route in Example 2, wherein 15 can be obtained by replacing a8 with compound o8 in equal mole ratio, while other raw materials and proportions were identical. (Compound 15, MS: Ms/2=957.37)

Example 16 Synthesis of Compound 16

Synthesis Route:

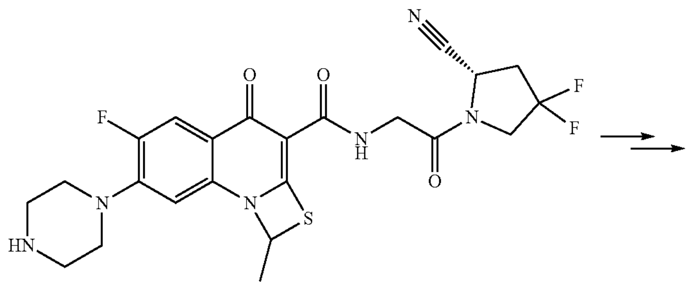

o8

-continued

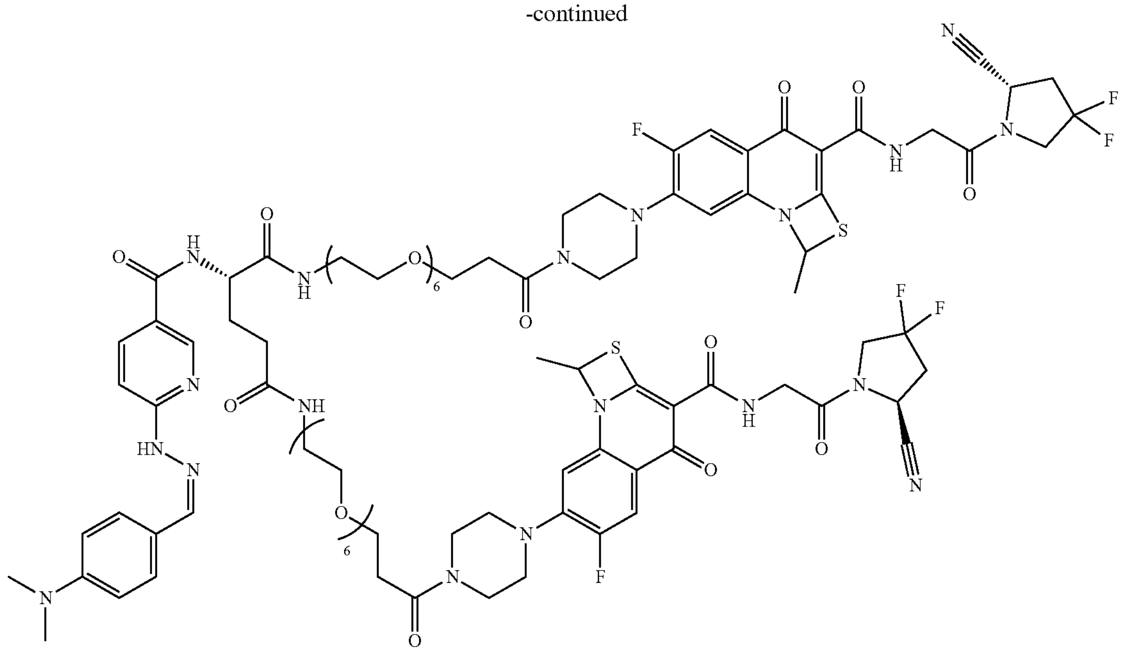

16

Compound 16 was synthesized following the synthesis route in Example 3, wherein 16 can be obtained by replacing a8 with compound o8 in equal mole ratio, while other raw materials and proportions were identical. (Compound 16, MS: Ms/2=1045.42)

Example 17 Preparation of Radioactive 99mTc-Labeled Complex

To a vial, 10 µL of an aqueous solution of triphenylphosphine-3,3',3"-trisulfonic acid trisodium salt (150 mg/mL), 10 µL of an aqueous solution of tricine (200 mg/mL) and 1 L of a DMSO solution of labeled precursor compound 5 or compound 9 (1 mg/mL) were added, and then 2 mCi of sodium pertechnetate eluent was added. The vial was placed into a metal bath, heated and reacted at 100° C. for 20 min, and cooled to room temperature. A C18 cartridge was taken, and activated by elution with 10 mL of anhydrous ethanol and 10 mL of normal saline. Reaction solution was diluted with 2 mL of normal saline, filtered through the C18 cartridge, washed with 5 mL of normal saline, eluted with 75% ethanol, diluted with normal saline, and filtered through a sterile filtration membrane, so as to yield injection 99mTc-5 or 99mTc-9 of 99mTc-labelled complex, respectively.

Example 18 Cell Uptake Experiment

Figure 18:
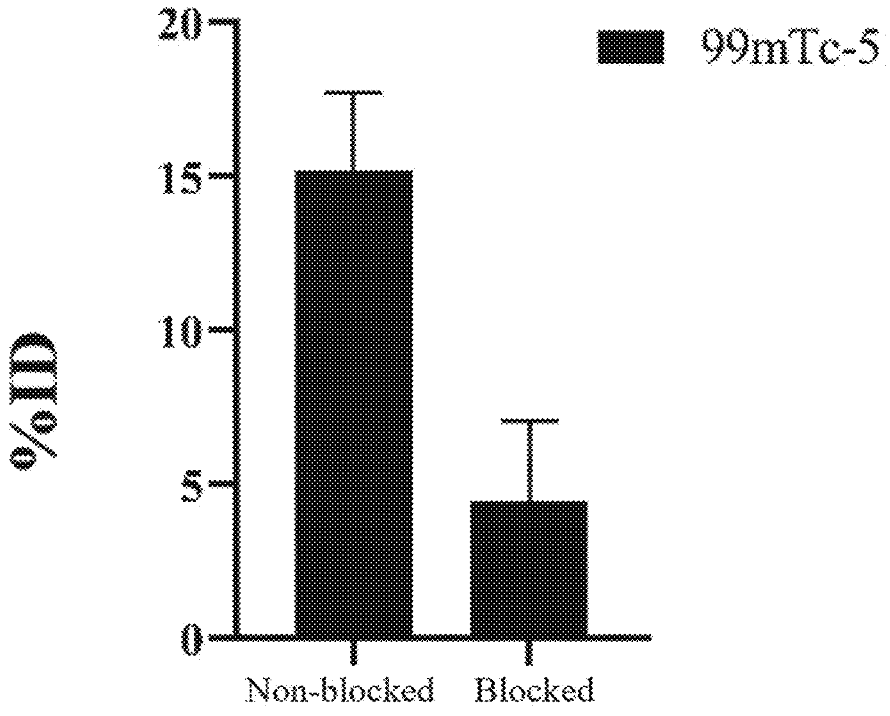
FIG. 18 is a graph of uptake rates of 99mTc-labeled compounds 5 and 9 in U87MG cells in the present disclosure: A: 99mTc-5; and B: 99mTc-9.
Figure 18:
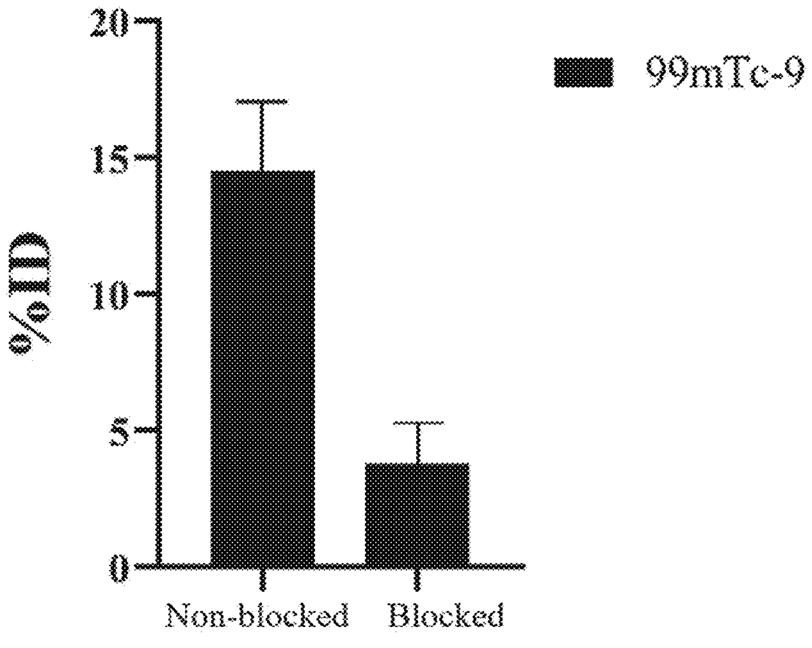

U87MG cells ($1\times10^5$ cells per well) were seeded in 6-well plates. 17.5 kBq of 99mTc-5 or 99mTc-9 was added respectively to each well. After incubation at 4° C. for 1 h, the cells were washed 3 times with cold PBS and collected. Quantity of cell-related radiation was measured using a γ counter, and results were expressed by percentage of total additive amount per $10^5$ cells. In a blocking experiment, U87MG cells were incubated with a 100-fold excess of FAP inhibitor (UAMC1110) for 1 h, followed by adding probe 99mTc-5 or 99mTc-9 respectively for incubation. As shown in FIG. 18, the 99mTc-5 or 99mTc-9 probe had a relatively high tumor cell uptake rate (~15% ID).

Example 19 Animal Imaging Experiment

Figure 13:
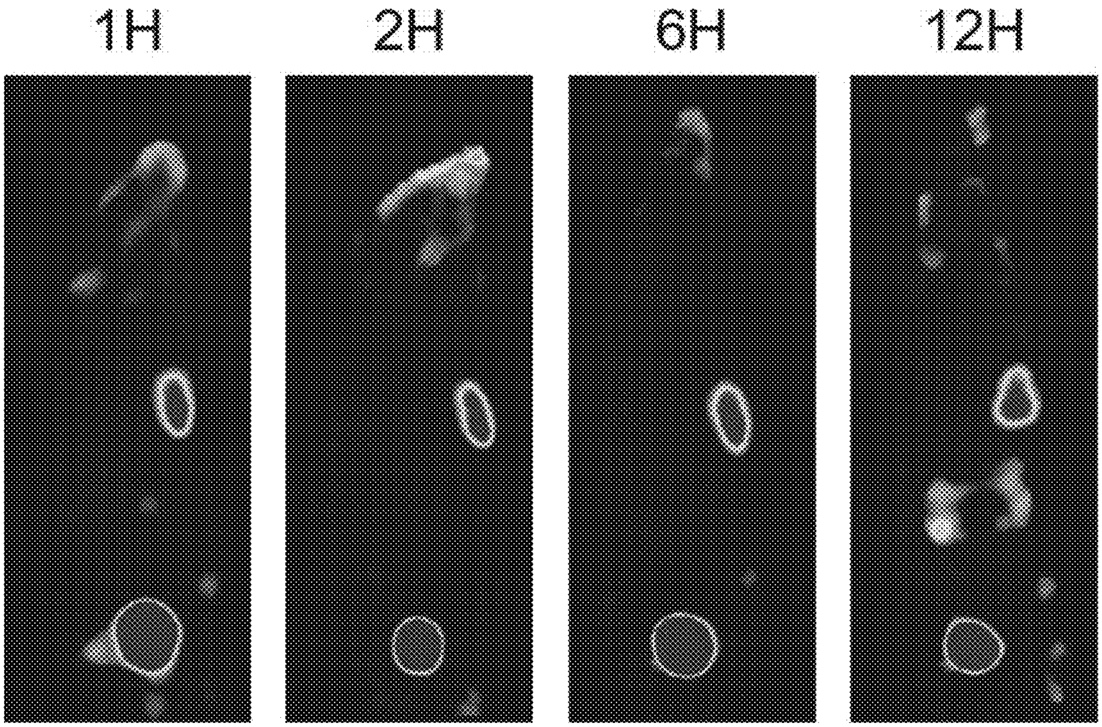
FIG. 13 shows imaging results of 99mTc-labeled compound 5 in U87MG mice in examples of the present disclosure.
Figure 14:
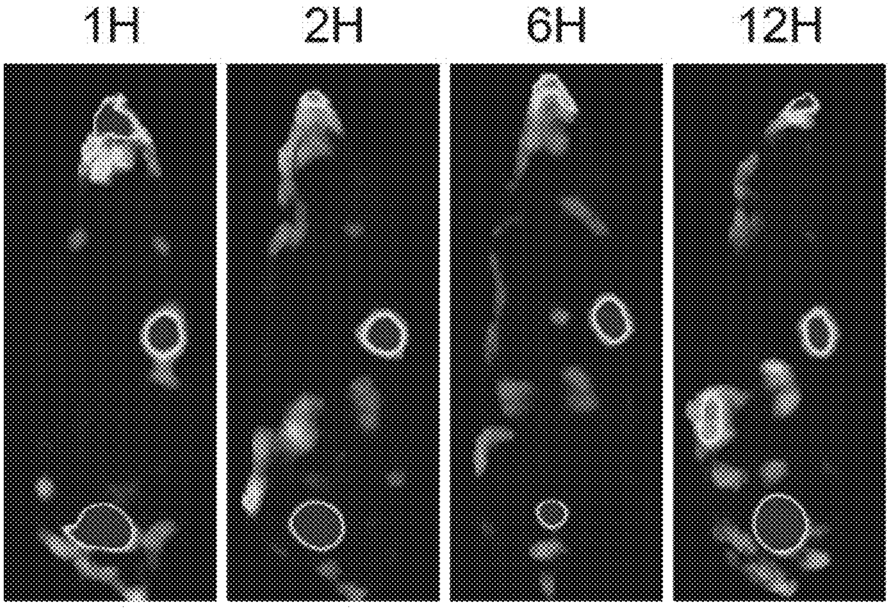
FIG. 14 shows imaging results of 99mTc-labeled compound 9 in U87MG mice in examples of the present disclosure.
Figure 15:
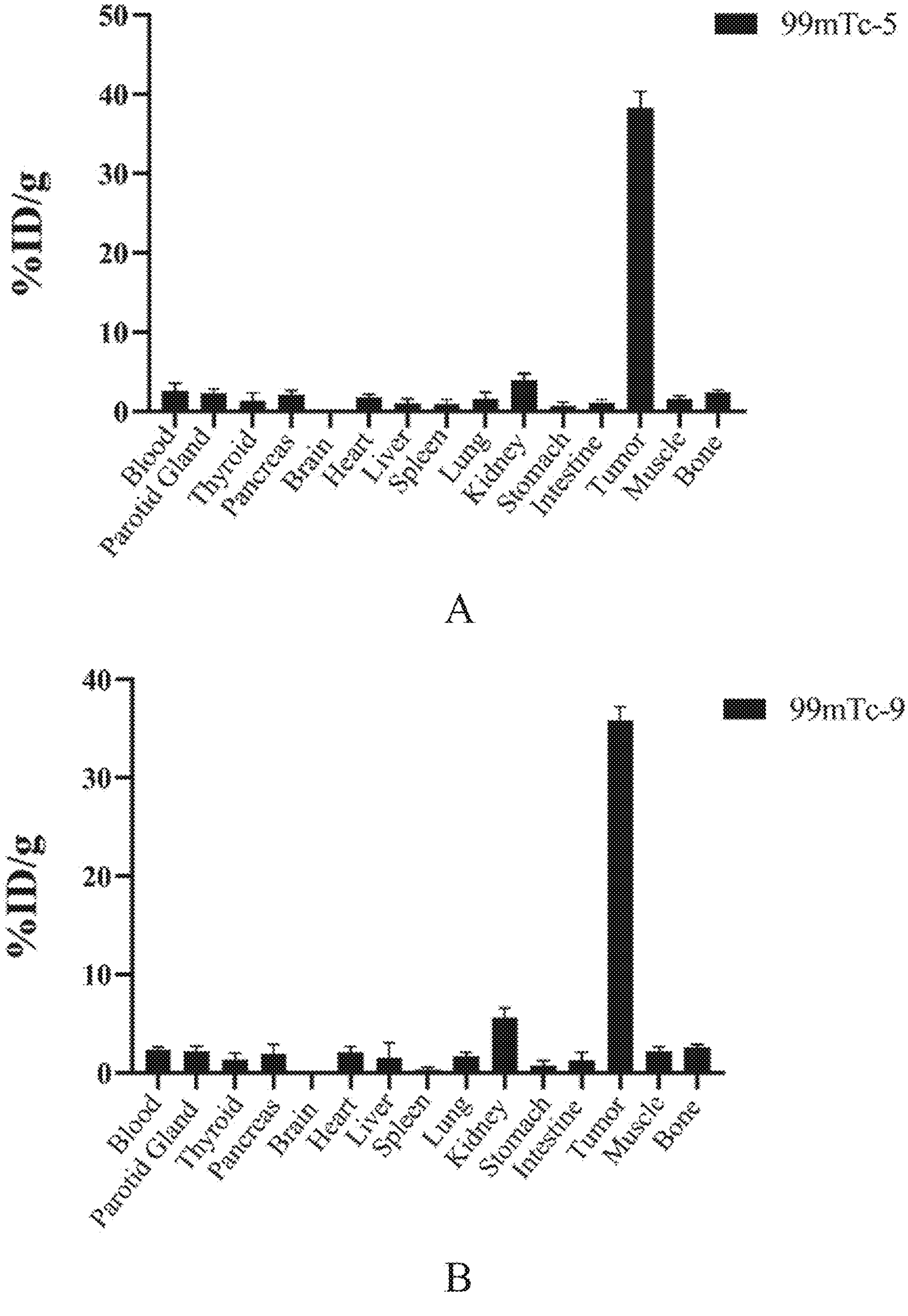
FIG. 15 shows ex vivo distribution statistical graphs of 99mTc-labeled compounds 5 and 9 in tumors and vital organs in U87MG mice at 1 hour after injection in the present disclosure: A: 99mTc-5; and B: 99mTc-9.
Figure 16:
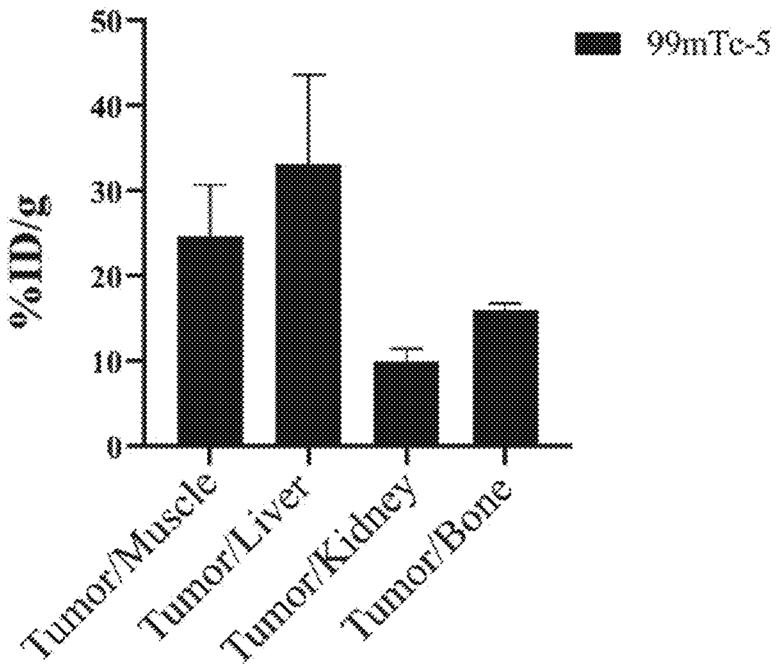
FIG. 16 shows graphs of tumor-to-vital organ uptake rates of 99mTc-labeled compounds 5 and 9 in U87MG mice at 1 hour after injection in the present disclosure: A: 99mTc-5; and B: 99mTc-9.
Figure 16:
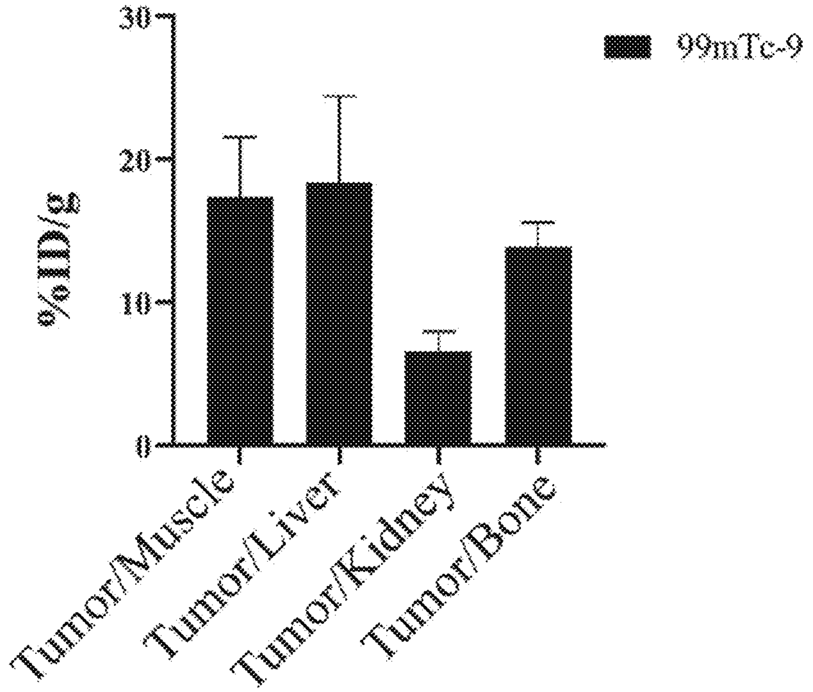
Figure 17:
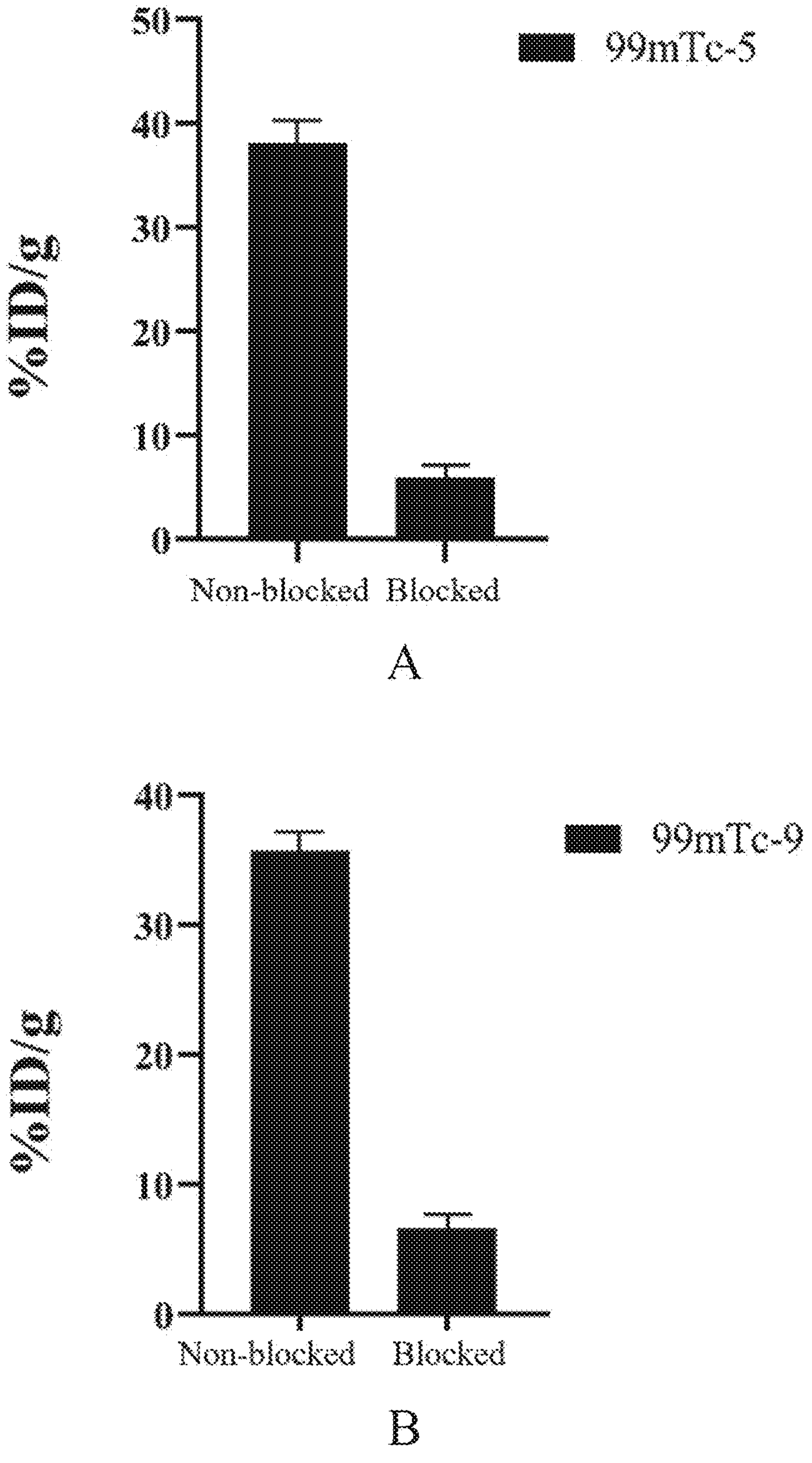
FIG. 17 shows ex vivo distribution statistical graphs of 99mTc-labeled compounds 5 and 9 in U87MG mice after tumor blocking at 1 hour after injection in the present disclosure: A: 99mTc-5; and B: 99mTc-9.

The probe 99mTc-5 or 99mTc-9 was injected into U87MG tumor-bearing mice via tail veins, with each mouse being injected with 300 µCi of technetium-labelled probe. The injected tumor-bearing mice were scanned using Micro-SPECT/CT, and the tumor-bearing mice remained in an anaesthetised state through continuous inhalation of 2% isoflurane. Imaging was performed at time points of 1 h, 2 h, 6 h and 12 h after the injection. As shown in FIGS. 13 and 14, the 99mTc-5/99mTc-9 probes exhibited excellent tumor targeting and long retention capabilities. Biodistribution of 99mTc-5 or 99mTc-9 in vital organs and tumor tissues of the tumor-bearing mice was further evaluated. 1.85 MBq of probe 99mTc-5 or 99mTc-9 was injected into U87MG tumor-bearing mice. At 1 h after injection, isolation and weighing were carried out, and quantities of radiation in various organs were measured using the γ counter. As shown in FIG. 15, the probe 99mTc-5 had the tumor uptake rate of up to 38.1% ID/g at 1 hour, and 99mTc-9 had the tumor uptake rate of up to 35.7% ID/g at 1 hour. As shown in FIG. 16, such probes had excellent imaging contrast. In the blocking experiment, the probe 99mTc-5 or 99mTc-9 and a 100-fold excess of FAP inhibitor (UAMC1110) were co-injected into the U87MG tumor-bearing mice, and ex vivo distribution was performed, for tumor uptake change results. As shown in FIG. 17, the 99mTc-5/99mTc-9 probes exhibited specificity for targeting fibroblast activation protein.

The invention claimed is:

1. A dimeric compound targeting FAP or a pharmaceutically acceptable salt thereof, wherein the dimeric compound targeting FAP has a structure as follows:

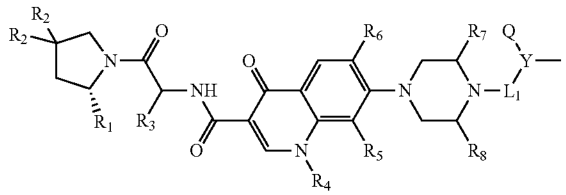

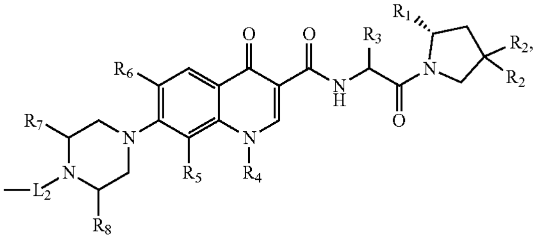

wherein $R_1$ is selected from cyano;

$R_2$ is selected from hydrogen, fluoro or chloro;

$R_3$ is selected from hydrogen or methyl;

$R_4$ is selected from hydrogen, methyl, ethyl, propyl, cyclopropyl or cyclobutyl;

$R_5$ and $R_6$ are independently selected from hydrogen, methyl, fluoro or chloro;

$R_7$ and $R_8$ are independently selected from hydrogen or methyl;

$L_1$ and $L_2$ are independently selected from any one of:

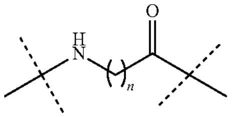

n = 1-20

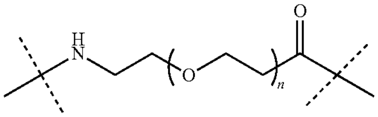

n = 0-10

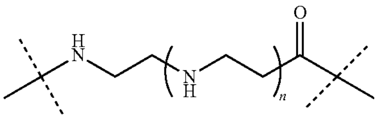

n = 0-10

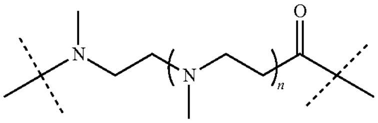

n = 0-10

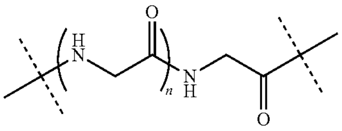

n = 1-10

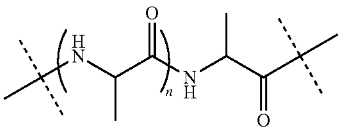

n = 1-10

-continued

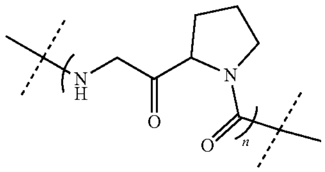

n = 1-10

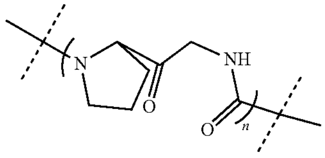

n = 1-10

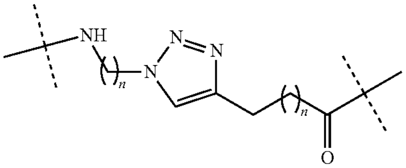

n = 1-10

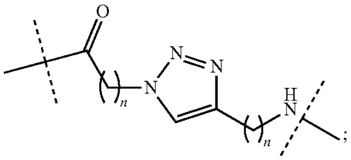

n = 1-10

Y is selected from any one of:

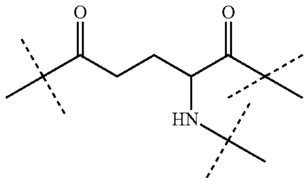

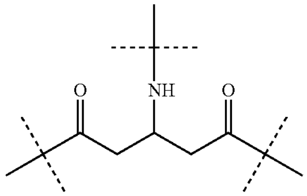

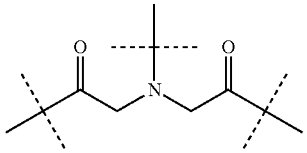

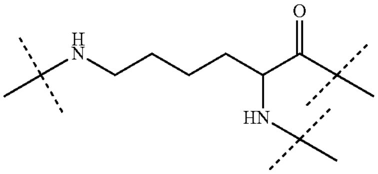

-continued
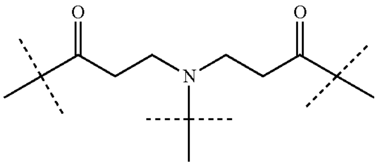
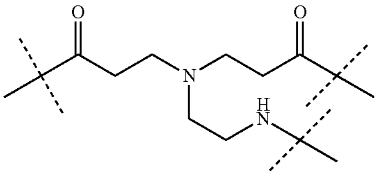
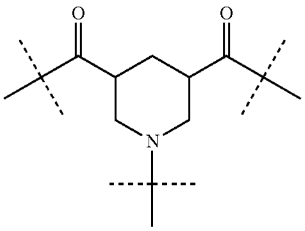
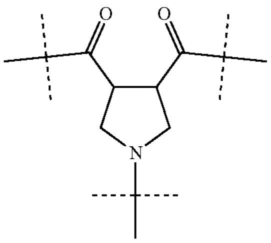
;
Q is a hydrogen atom or is used as a nuclide chelating group moiety, and is selected from any one of:
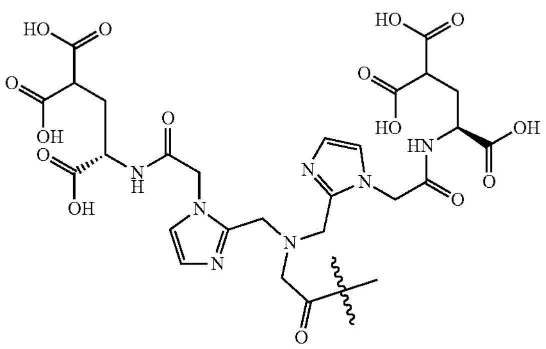
-continued
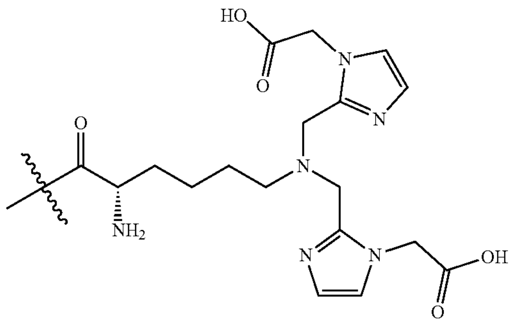
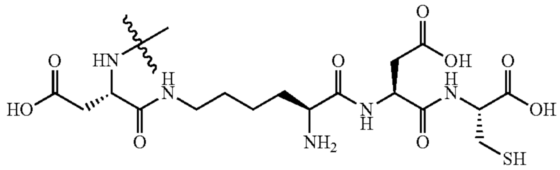
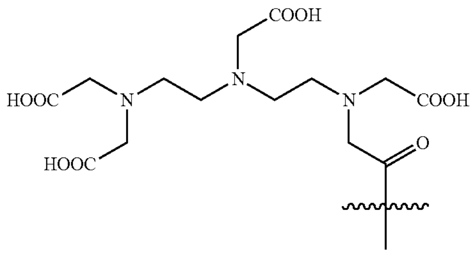
DTPA
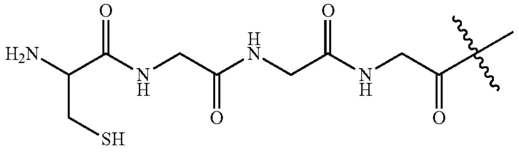
MAG3
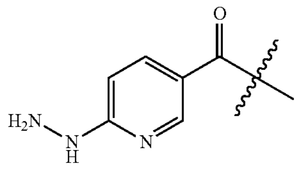
HYNIC
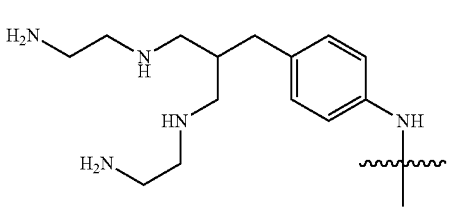
.

2. A dimeric compound targeting FAP and a pharmaceutically acceptable salt thereof, wherein the dimeric compound is selected from any one of:
1
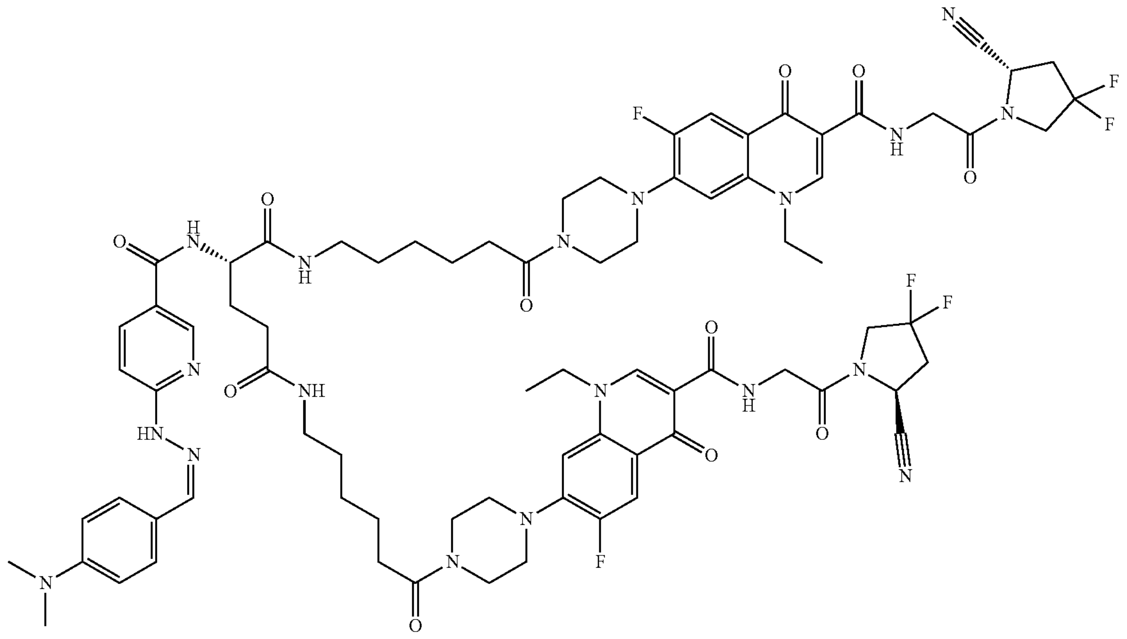
2
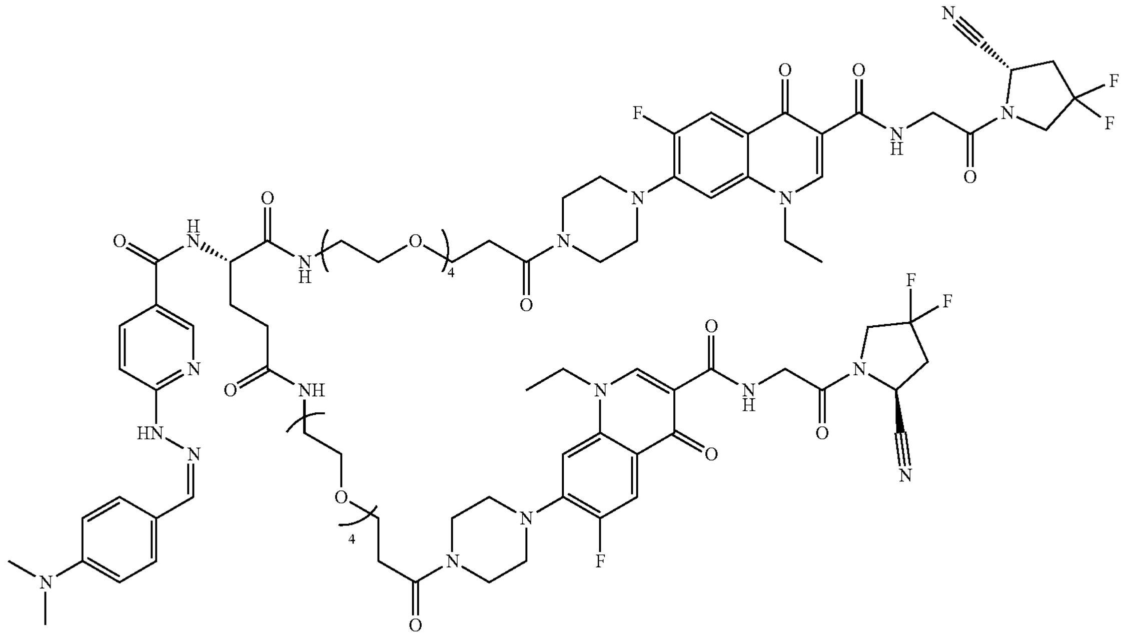

-continued
3
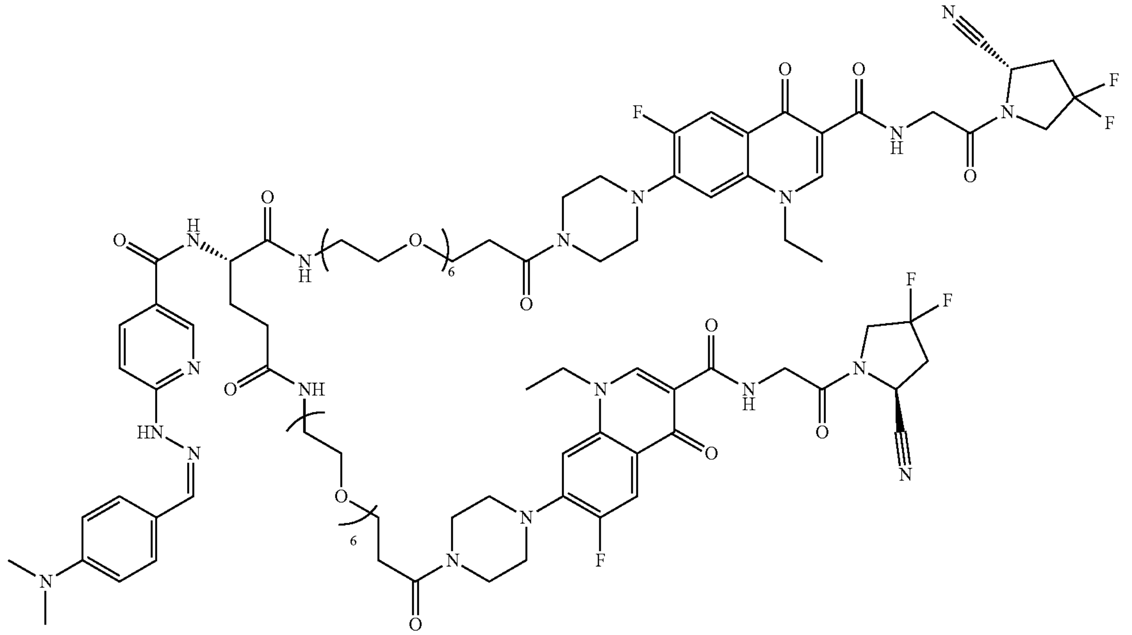
4
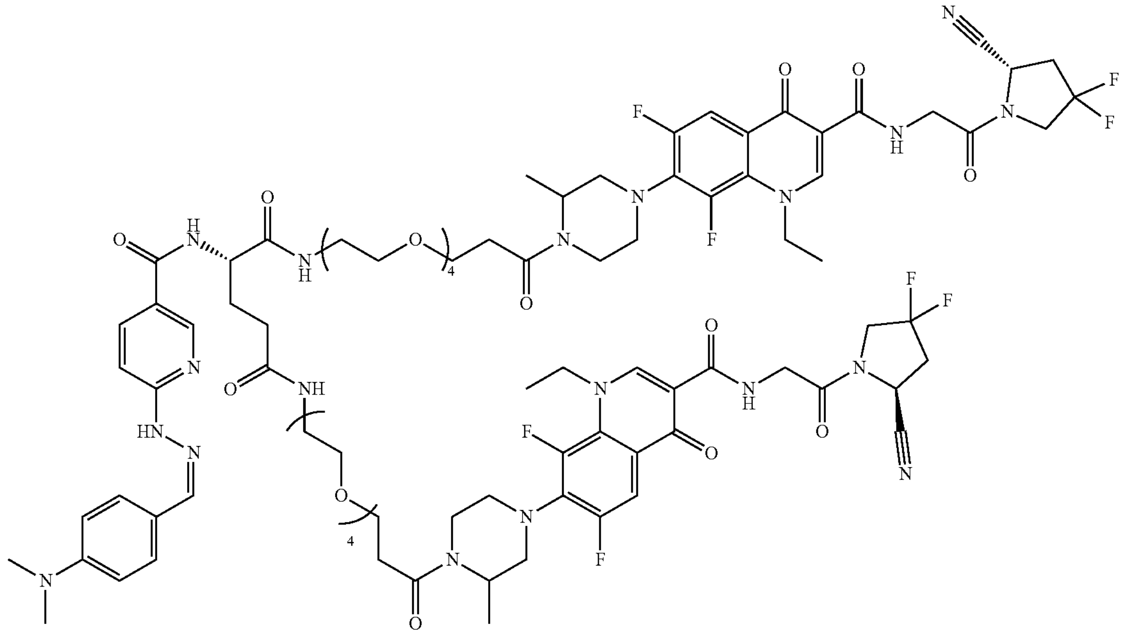

-continued
5
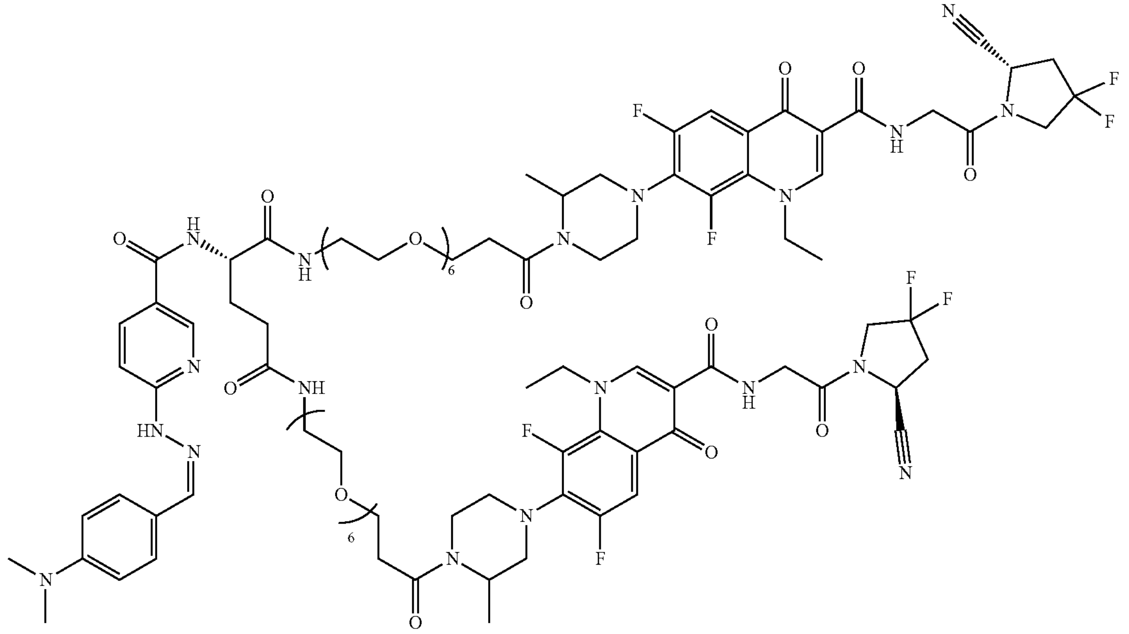
6
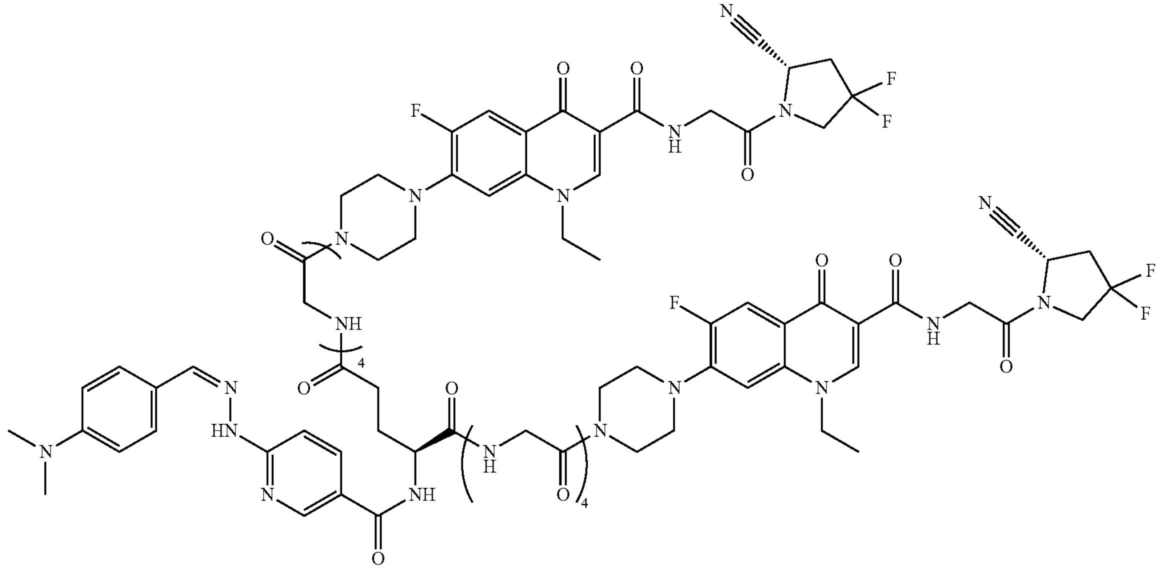

-continued
7
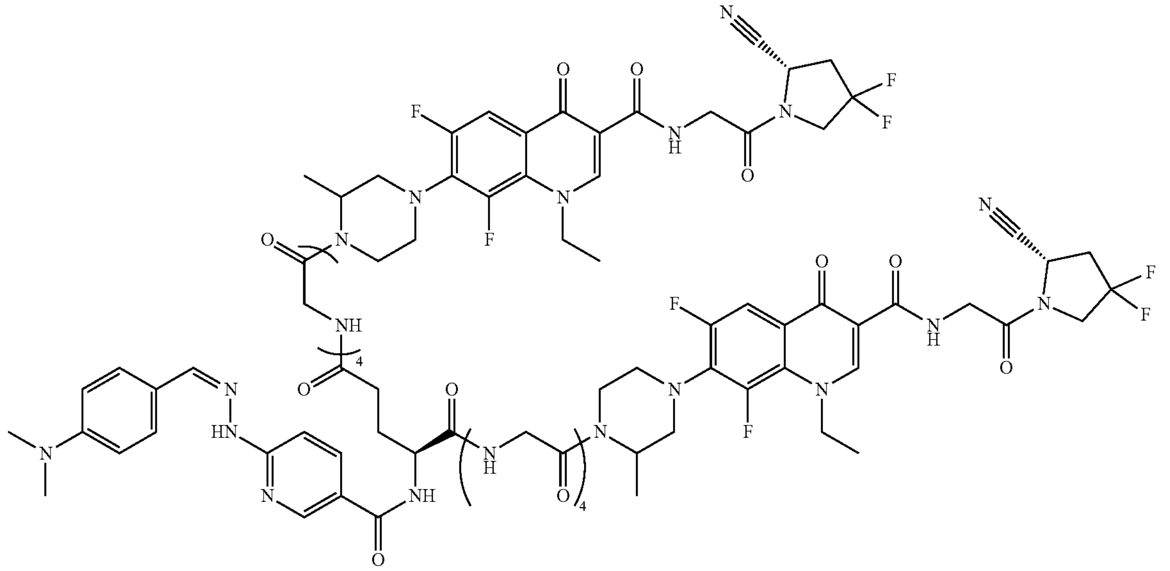
8
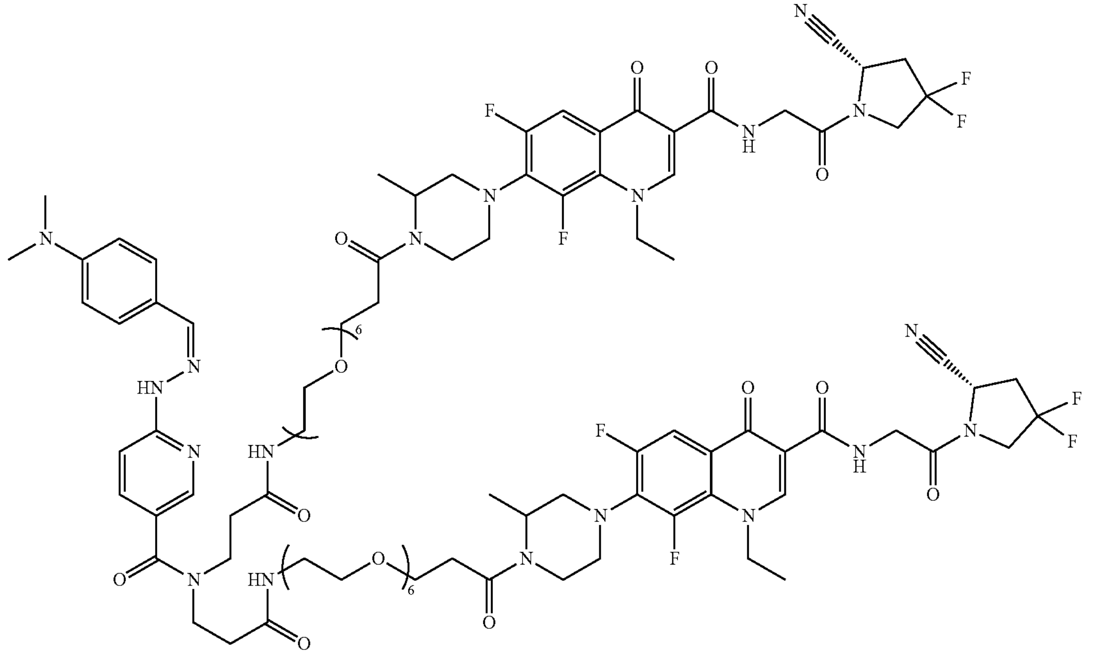

-continued
9
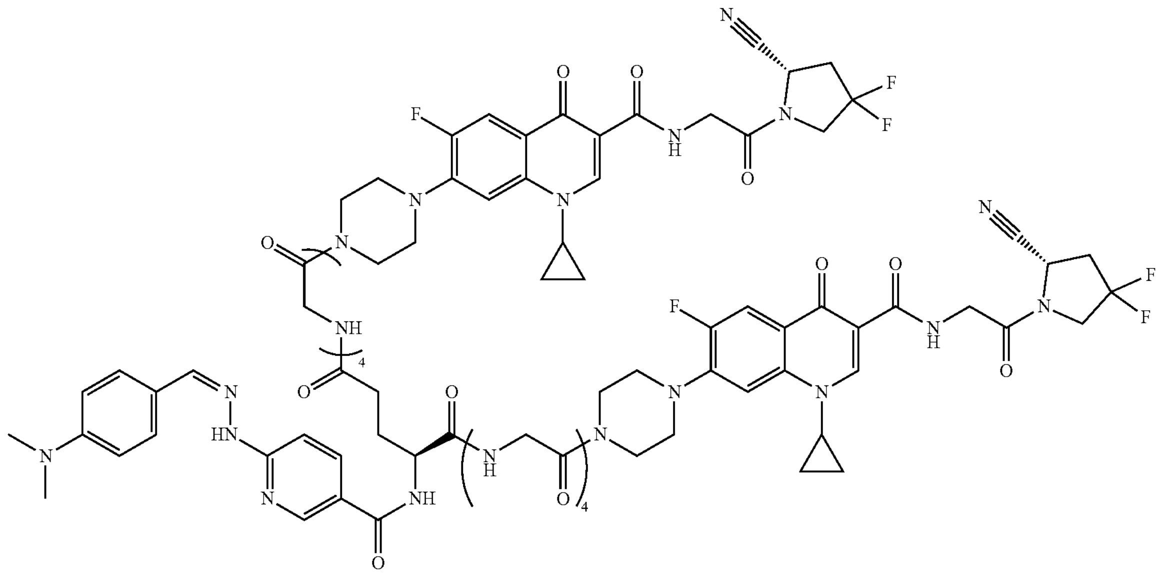
10
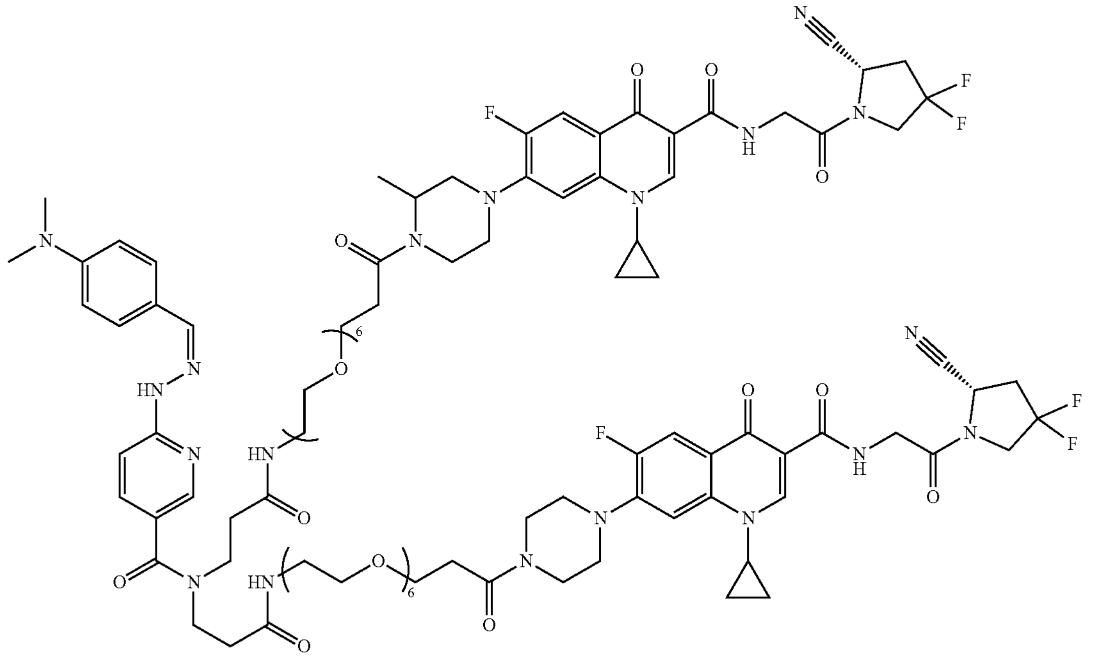

-continued
11
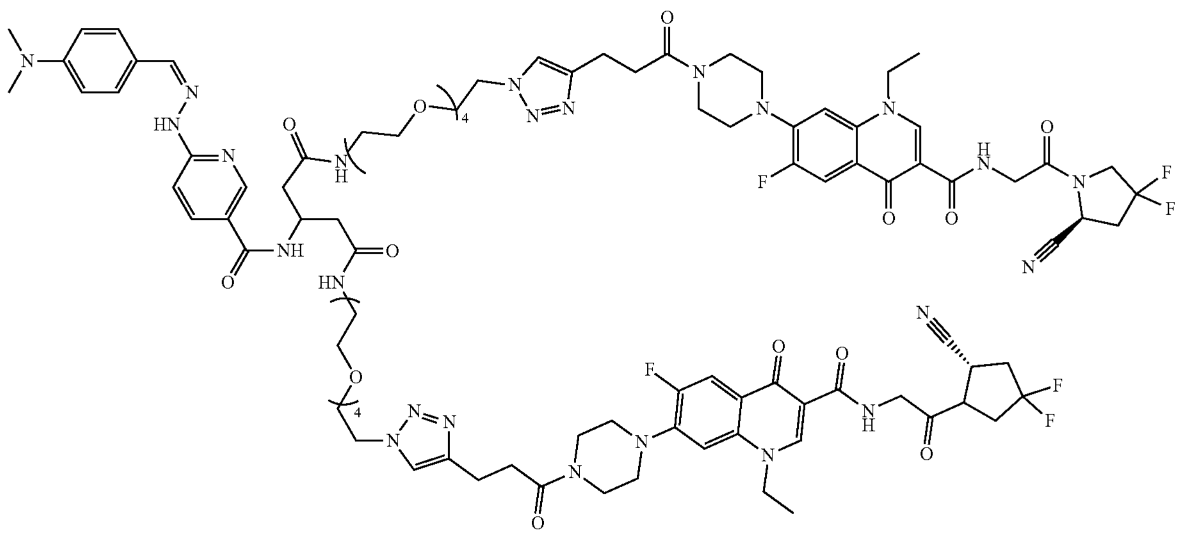
12
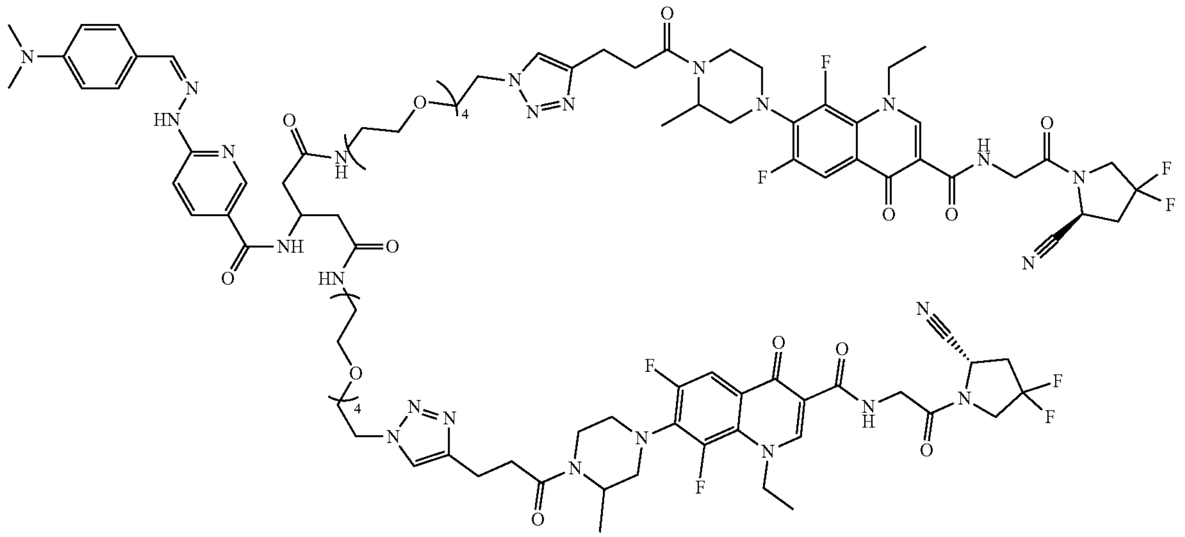
13
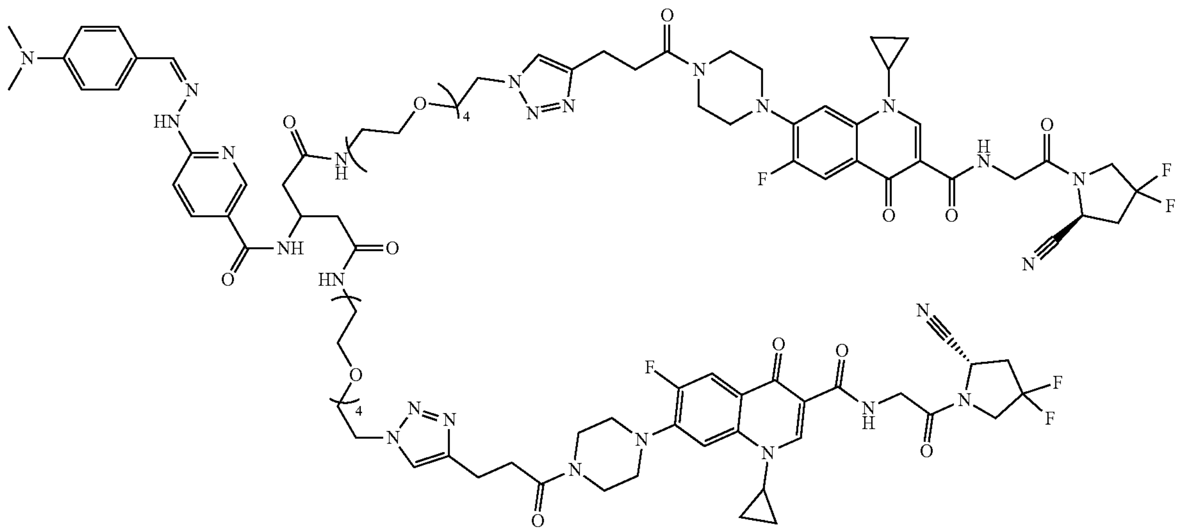

-continued
14
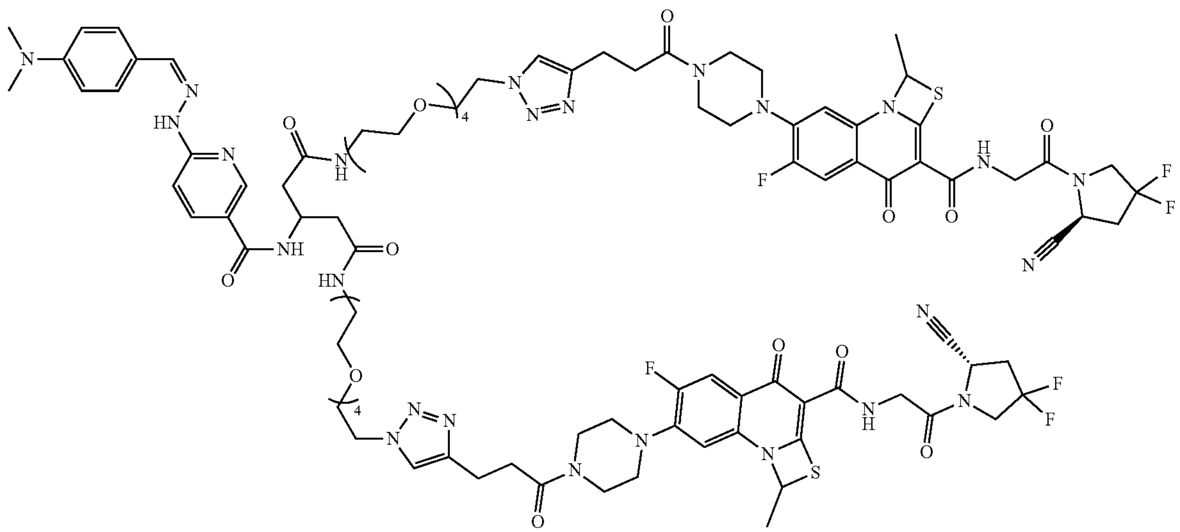
15
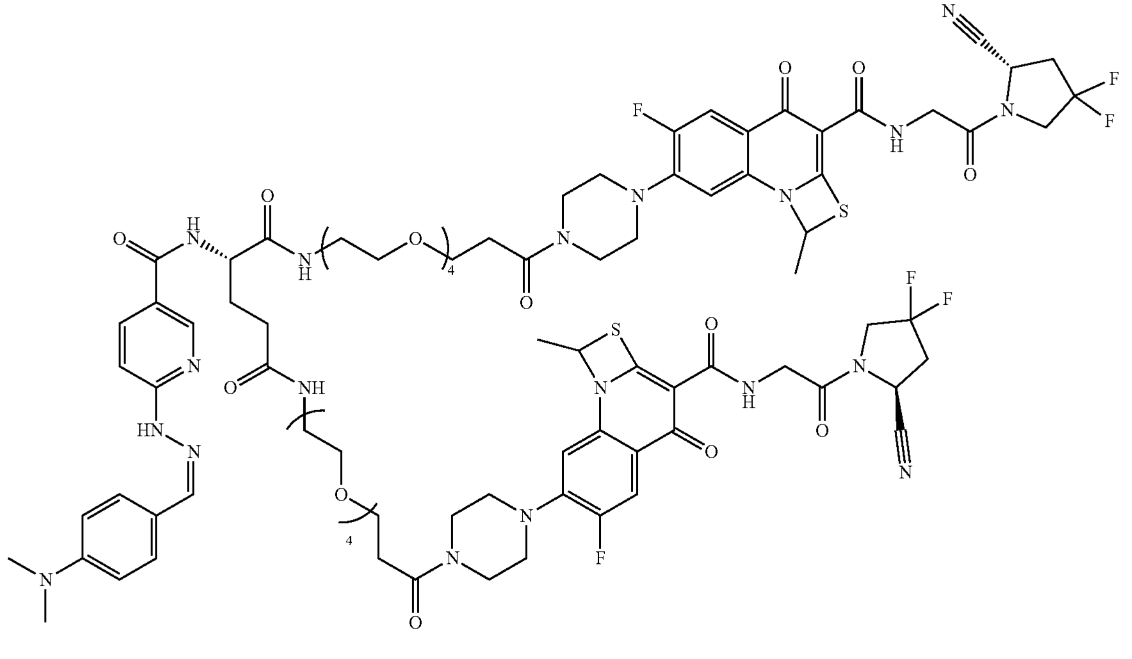

-continued

16

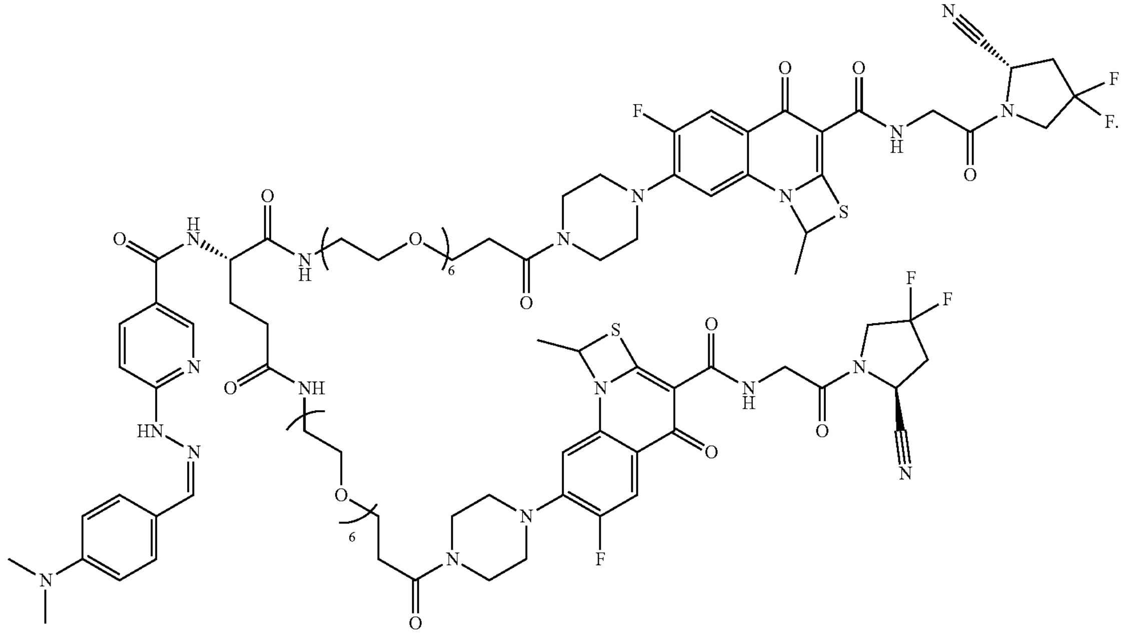

3. The dimeric compound targeting FAP or pharmaceutically acceptable salt thereof according to claim 1, wherein the pharmaceutically acceptable salt is selected from the group consisting of hydrochlorides, sulfates, trifluoroacetates, fumarates, succinates, sulfonates, maleates, acetates, phosphates and citrates.

4. A radionuclide technetium-99m labelled compound targeting fibroblast activation protein, wherein the radionuclide technetium-99m labelled compound targeting fibroblast activation protein is prepared through reaction of the dimeric compound targeting FAP or pharmaceutically acceptable salt thereof according to claim 1 with a compound containing radionuclide technetium-99m according to an existing wet labeling method or a freeze-drying labeling method.

5. A 99m-Tc labelled kit, comprising the dimeric compound targeting FAP or pharmaceutically acceptable salt thereof according to claim 1, a ligand forming coordination with technetium-99m, a reductant, an additive, and a stabilizer.

* * * * *